US012558128B2

(12) United States Patent
Serbousek et al.

(10) Patent No.: US 12,558,128 B2
(45) Date of Patent: Feb. 24, 2026

(54) BONE FUSION DEVICE, SYSTEM AND METHODS

(71) Applicant: TRIQUEUE HOLDINGS, LLC, Winona Lake, IN (US)

(72) Inventors: Jon C. Serbousek, Winona Lake, IN (US); Jeffrey Nycz, Warsaw, IN (US); Richard David Fessler, Winnetka, IL (US); Jill A. Serbousek, Winona Lake, IN (US); Richard G. Fessler, Lake Forest, IL (US)

(73) Assignee: TRIQUEUE HOLDINGS, LLC, Winona Lake, IN (US)

( * ) Notice: Subject to any disclaimer, the term of this patent is extended or adjusted under 35 U.S.C. 154(b) by 63 days.

(21) Appl. No.: 17/456,976

(22) Filed: Nov. 30, 2021

(65) Prior Publication Data

US 2022/0079629 A1     Mar. 17, 2022

Related U.S. Application Data

(63) Continuation of application No. 16/273,567, filed on Feb. 12, 2019, now Pat. No. 11,185,350, which is a
(Continued)

(51) Int. Cl.
*A61B 17/70* (2006.01)
*A61B 17/17* (2006.01)
(Continued)

(52) U.S. Cl.
CPC ...... *A61B 17/7005* (2013.01); *A61B 17/1757* (2013.01); *A61B 17/68* (2013.01);
(Continued)

(58) Field of Classification Search
CPC .............. A61B 7/1728; A61B 17/1717; A61B 17/1721; A61B 17/1757; A61B 17/7067
(Continued)

(56) References Cited

U.S. PATENT DOCUMENTS

| 5,027,793 A | 7/1991 | Engelhardt |
| 5,364,399 A | 11/1994 | Lowery |

(Continued)

FOREIGN PATENT DOCUMENTS

| WO | 2007149426 | 12/2007 |
| WO | 2011155931 | 12/2011 |

(Continued)

OTHER PUBLICATIONS

International Search Report and Written Opinion of the International Searching Authority for PCT Application No. PCT/US2017/047035, Oct. 19, 2017, 7 pages.
(Continued)

*Primary Examiner* — Jan Christopher L Merene

(74) *Attorney, Agent, or Firm* — Heslin Rothenberg Farley & Mesiti P.C.; Jacquelyn A. Graff, Esq.

(57) ABSTRACT

The present disclosure includes implant systems, devices, implants, guides, instruments and methods of use. The insertion guide including a base member having a first opening with a first trajectory and a second opening with a second trajectory, a connecting member having a first end and a second end, wherein the first end is coupled to the base member and a locking block coupled to the second end of the connecting member. The locking block has a first guide hole and a second guide hole. The implant including a body including a first hole at a first end of the body, a second hole at a second end of the body, and a locking opening positioned between the first hole and the second hole. Methods of using the implant systems are also disclosed.

20 Claims, 49 Drawing Sheets

Related U.S. Application Data continuation of application No. PCT/US2017/047035, filed on Aug. 15, 2017.

(60) Provisional application No. 62/375,114, filed on Aug. 15, 2016.

(51) Int. Cl.

| | |
|---|---|
| *A61B 17/68* | (2006.01) |
| *A61B 17/88* | (2006.01) |
| *A61F 2/46* | (2006.01) |
| *A61F 2/44* | (2006.01) |

(52) U.S. Cl.
CPC ...... *A61B 17/7062* (2013.01); *A61B 17/7091* (2013.01); *A61B 17/8888* (2013.01); *A61F 2/4611* (2013.01); *A61B 17/7085* (2013.01); *A61B 17/888* (2013.01); *A61F 2/4455* (2013.01); *A61F 2/4603* (2013.01)

(58) Field of Classification Search
USPC ................................................. 606/248–249
See application file for complete search history.

(56) References Cited

U.S. PATENT DOCUMENTS

| | | | | | |
|---|---|---|---|---|---|
| 5,766,252 | A | 6/1998 | Henry | | |
| 5,980,572 | A | 11/1999 | Kim | | |
| 6,235,059 | B1 | 5/2001 | Benezech | | |
| 6,514,253 | B1 | 2/2003 | Yao | | |
| 6,613,090 | B2 | 9/2003 | Fuss | | |
| 7,537,596 | B2 | 5/2009 | Jensen | | |
| 7,628,816 | B2 * | 12/2009 | Magerl | ................. | A61F 2/4611 606/280 |
| 7,951,178 | B2 | 5/2011 | Jensen | | |
| 7,967,851 | B2 | 6/2011 | Bickley | | |
| 8,025,681 | B2 | 9/2011 | Colleran | | |
| D664,252 | S | 7/2012 | Weiland | | |
| 8,231,627 | B2 | 7/2012 | Huebner | | |
| 8,328,872 | B2 * | 12/2012 | Duffield | ............. | A61B 17/8042 623/17.16 |
| D733,303 | S | 6/2015 | Peterson et al. | | |
| 9,060,808 | B2 | 6/2015 | Overes | | |
| 9,084,618 | B2 | 7/2015 | Serbousek | | |
| D767,133 | S | 9/2016 | Gotfried | | |
| 9,480,507 | B2 | 11/2016 | Overes et al. | | |
| 9,636,154 | B2 | 5/2017 | Overes et al. | | |
| D789,540 | S | 6/2017 | Gyorgy | | |
| D819,209 | S | 5/2018 | DaCosta et al. | | |
| 9,987,024 | B2 | 6/2018 | Frey et al. | | |
| 10,034,760 | B2 | 7/2018 | Jensen et al. | | |
| D847,996 | S | 5/2019 | Surgeon et al. | | |
| D857,201 | S | 8/2019 | Predick et al. | | |
| 2002/0151897 | A1 | 10/2002 | Zirkle, Jr. | | |
| 2002/0188296 | A1 * | 12/2002 | Michelson | ......... | A61B 17/7059 606/71 |
| 2003/0125739 | A1 * | 7/2003 | Bagga | ................... | A61L 27/446 606/907 |
| 2004/0176852 | A1 | 9/2004 | Zubok | | |
| 2004/0230304 | A1 | 11/2004 | Yuan | | |
| 2005/0015093 | A1 * | 1/2005 | Suh | ................... | A61B 17/1757 606/96 |
| 2005/0065607 | A1 * | 3/2005 | Gross | ....................... | A61F 2/28 623/17.11 |
| 2005/0240267 | A1 * | 10/2005 | Randall | ................. | A61F 2/4611 623/17.11 |
| 2005/0251146 | A1 * | 11/2005 | Martz | ................ | A61B 17/1604 606/84 |
| 2005/0261767 | A1 * | 11/2005 | Anderson | ............... | A61L 27/36 623/16.11 |
| 2006/0058796 | A1 | 3/2006 | Hartdegen | | |
| 2006/0189996 | A1 | 8/2006 | Orbay | | |
| 2006/0189997 | A1 | 8/2006 | Guenther | | |
| 2006/0229618 | A1 * | 10/2006 | Dube | ................. | A61B 17/8042 606/295 |
| 2006/0241646 | A1 | 10/2006 | Stihl | | |
| 2008/0177306 | A1 * | 7/2008 | Lamborne | .......... | A61B 17/7062 623/17.11 |
| 2009/0012529 | A1 * | 1/2009 | Blain | ................... | A61B 17/808 606/86 A |
| 2009/0024132 | A1 | 1/2009 | Blain | | |
| 2009/0149861 | A1 | 6/2009 | Brodsky | | |
| 2009/0234455 | A1 * | 9/2009 | Moskowitz | .......... | A61B 17/809 606/301 |
| 2010/0004691 | A1 | 1/2010 | Amato | | |
| 2010/0094345 | A1 | 4/2010 | Saidha | | |
| 2010/0152745 | A1 | 6/2010 | Dudasik | | |
| 2010/0211074 | A1 * | 8/2010 | Hansson | ............ | A61B 17/1721 606/64 |
| 2011/0184470 | A1 | 7/2011 | Gorek | | |
| 2011/0264225 | A1 | 10/2011 | Michelson | | |
| 2011/0282397 | A1 | 11/2011 | Richter | | |
| 2012/0059425 | A1 | 3/2012 | Biedermann | | |
| 2012/0089191 | A1 | 4/2012 | Altarac | | |
| 2012/0136392 | A1 | 5/2012 | Keegan | | |
| 2012/0179259 | A1 | 7/2012 | McDonough | | |
| 2012/0197401 | A1 | 8/2012 | Duncan | | |
| 2012/0226319 | A1 | 9/2012 | Armstrong | | |
| 2012/0271312 | A1 | 10/2012 | Jansen | | |
| 2013/0041375 | A1 | 2/2013 | Fierlbeck | | |
| 2013/0211462 | A1 | 8/2013 | Walker | | |
| 2013/0261673 | A1 | 10/2013 | Hawkins | | |
| 2014/0188223 | A1 | 7/2014 | Jensen et al. | | |
| 2014/0243898 | A1 | 8/2014 | Fessler | | |
| 2014/0249591 | A1 | 9/2014 | Peultier et al. | | |
| 2016/0228257 | A1 | 8/2016 | Predick et al. | | |
| 2016/0235448 | A1 | 8/2016 | Seex | | |
| 2017/0071750 | A1 | 3/2017 | Urban et al. | | |
| 2017/0238980 | A1 | 8/2017 | Lauf | | |
| 2017/0325845 | A1 | 11/2017 | Donner et al. | | |
| 2017/0340358 | A1 | 11/2017 | Bullard | | |
| 2019/0105065 | A1 | 4/2019 | Sharifi-Mehr et al. | | |
| 2021/0113249 | A1 * | 4/2021 | Shoemaker | ............. | A61L 31/06 |

FOREIGN PATENT DOCUMENTS

| | | |
|---|---|---|
| WO | 2013169306 | 11/2013 |
| WO | 2016044845 | 3/2016 |

OTHER PUBLICATIONS

Extended European Search Report issued in European Patent Application No. 17842027.9, Jun. 25, 2020, 14 pages.
First Examination Report issued in Chinese Patent Application No. 201780050349.8, Apr. 26, 2021, 19 pages.
Examination Report No. 1 for Australian Patent Application No. 2017313725, Sep. 6, 2021, 4 pages.

* cited by examiner

100

160

160

160

162   170   178    164

174

172

168   176

160

176   168    174

162     166

172   178   170

140

140

450

452    454

458

462  468  466  464  456

450

452    454

460

456    470

500

500

BONE FUSION DEVICE, SYSTEM AND METHODS

CROSS REFERENCE TO RELATED APPLICATION

This application is a continuation of U.S. application Ser. No. 16/273,567 filed Feb. 12, 2019 and entitled Bone Fusion Device, System and Methods, which issues as U.S. Pat. No. 11,185,350 on Nov. 30, 2021, which is a continuation of International Application No. PCT/US2017/047035 filed on Aug. 15, 2017 and entitled Bone Fusion Device, System and Methods, which claims priority benefit under 35 U.S.C. § 119(e) of U.S. provisional application No. 62/375,114 filed Aug. 15, 2016 and entitled Bone Fusion Device, System and Methods, which are incorporated herein by reference in their entireties.

FIELD OF THE INVENTION

The present invention relates generally to general surgery, orthopaedic and neurosurgical implants used for insertion within a patient's vertebrae. More specifically, but not exclusively, the present invention concerns bone fusion devices, systems, instruments and methods of using the same.

BACKGROUND OF THE INVENTION

Spinal deformities may result from disease, age, or trauma causing destabilization of the spine. To correct destabilization of a patient's spine, fusion devices and systems may be used. Posterior lumbar spinal fusion with pedicle screws is the most common way to fuse a patient's spine. However, the pedicle screw fusion and surgical technique used for these fusions has not changed in the last 30-40 years. Moreover, the large number of necessary parts and pieces involved to complete these fusions increases risk, surgical time, potential for construct failure, and cost.

When a patient presents with a spondylolisthesis or a displacement of a spinal vertebra in relation to the vertebra below, which needs to be fixed prior to inserting stabilization devices, for example, screws. Thus, improved fusion and/or fixation devices, systems and instrumentation are needed.

SUMMARY OF THE INVENTION

Aspects of the present invention provide bone fusion devices, systems, instruments and methods of using the same.

In one aspect, provided herein is an insertion guide including a base member having a first opening with a first trajectory and a second opening with a second trajectory, a connecting member having a first end and a second end, wherein the first end is coupled to the base member and a locking block coupled to the second end of the connecting member. The locking block has a first guide hole and a second guide hole. The implant including a body including a first hole at a first end of the body, a second hole at a second end of the body, and a locking opening positioned between the first hole and the second hole.

In another aspect, provided herein is an insertion guide. The insertion guide including a base member having a first opening with a first trajectory and a second opening with a second trajectory, a connecting member having a first end and a second end, wherein the first end is coupled to the base member, and a locking block coupled to the second end of the connecting member, wherein the locking block has a first guide hole and a second guide hole.

In yet another aspect, provided herein is an implant. The implant including a body with a first hole at a first end of the body, a second hole at a second end of the body, and a locking opening positioned between the first hole and the second hole.

In still another aspect, provided herein is a reduction tool. The reduction tool including a handle member for coupling to the implant, a securement member, a base member coupled to the handle member with the securement member, a coupling member secured to the base member, and a bone contacting member coupled to the coupling member.

In yet another aspect, provided herein is a surgical method for using the implant system.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion.

DETAILED DESCRIPTION FOR CARRYING OUT THE INVENTION

Figure 1:
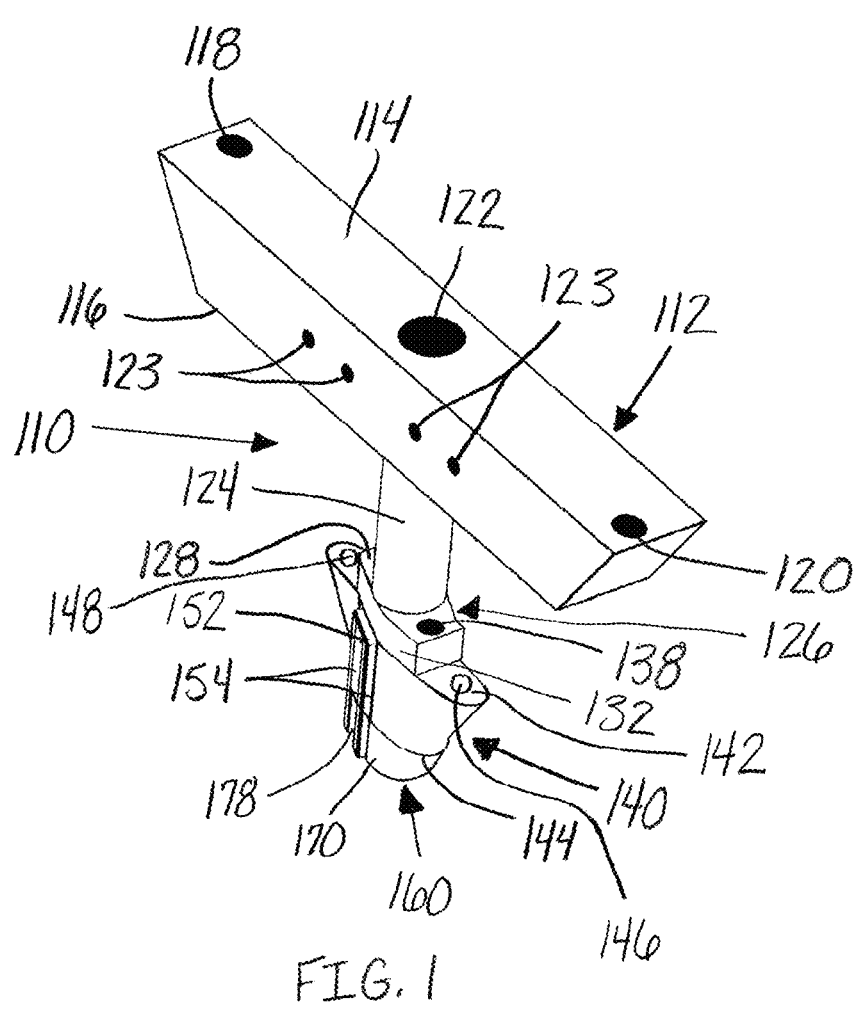
FIG. 1 is a top perspective view of an implant system, in accordance with an aspect of the present invention.
Figure 2:
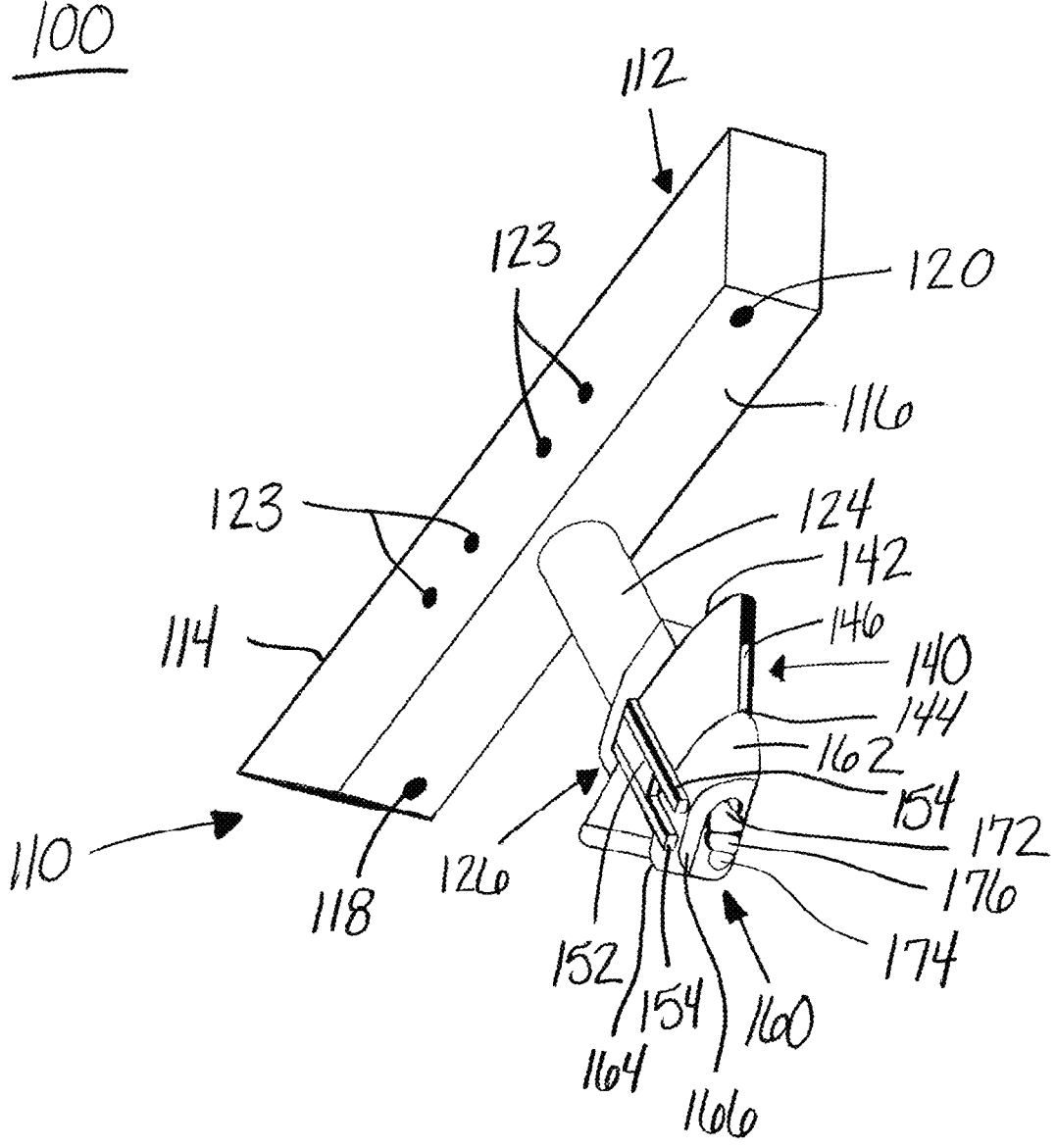
FIG. 2 is a first side, bottom perspective view of the implant system of FIG. 1, in accordance with an aspect of the present invention.
Figures 3, 4:
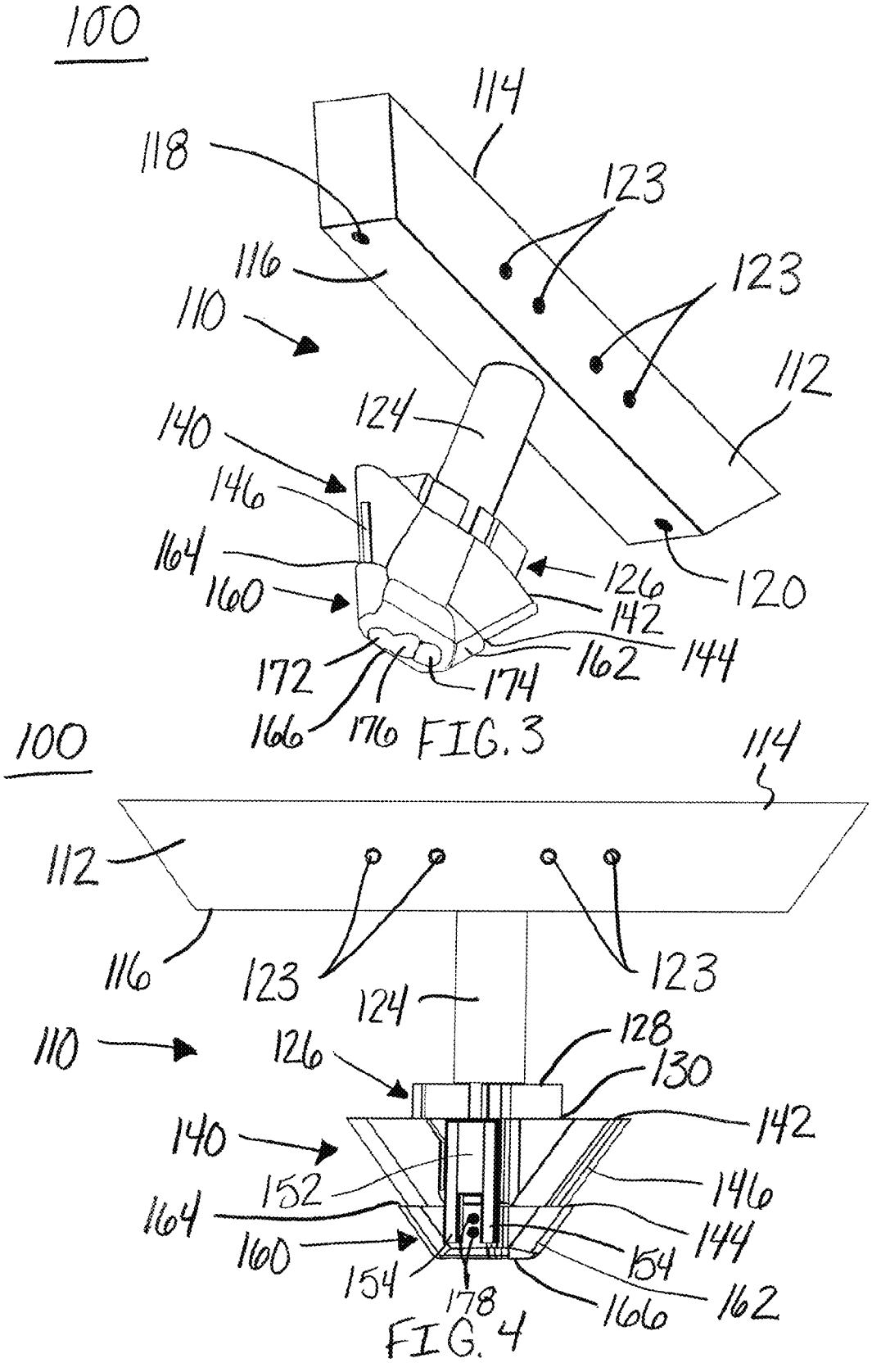
FIG. 3 is a second side, bottom perspective view of the implant system of FIG. 1, in accordance with an aspect of the present invention.
FIG. 4 is a first side view of the implant system of FIG. 1, in accordance with an aspect of the present invention.
Figures 5, 6, 7:
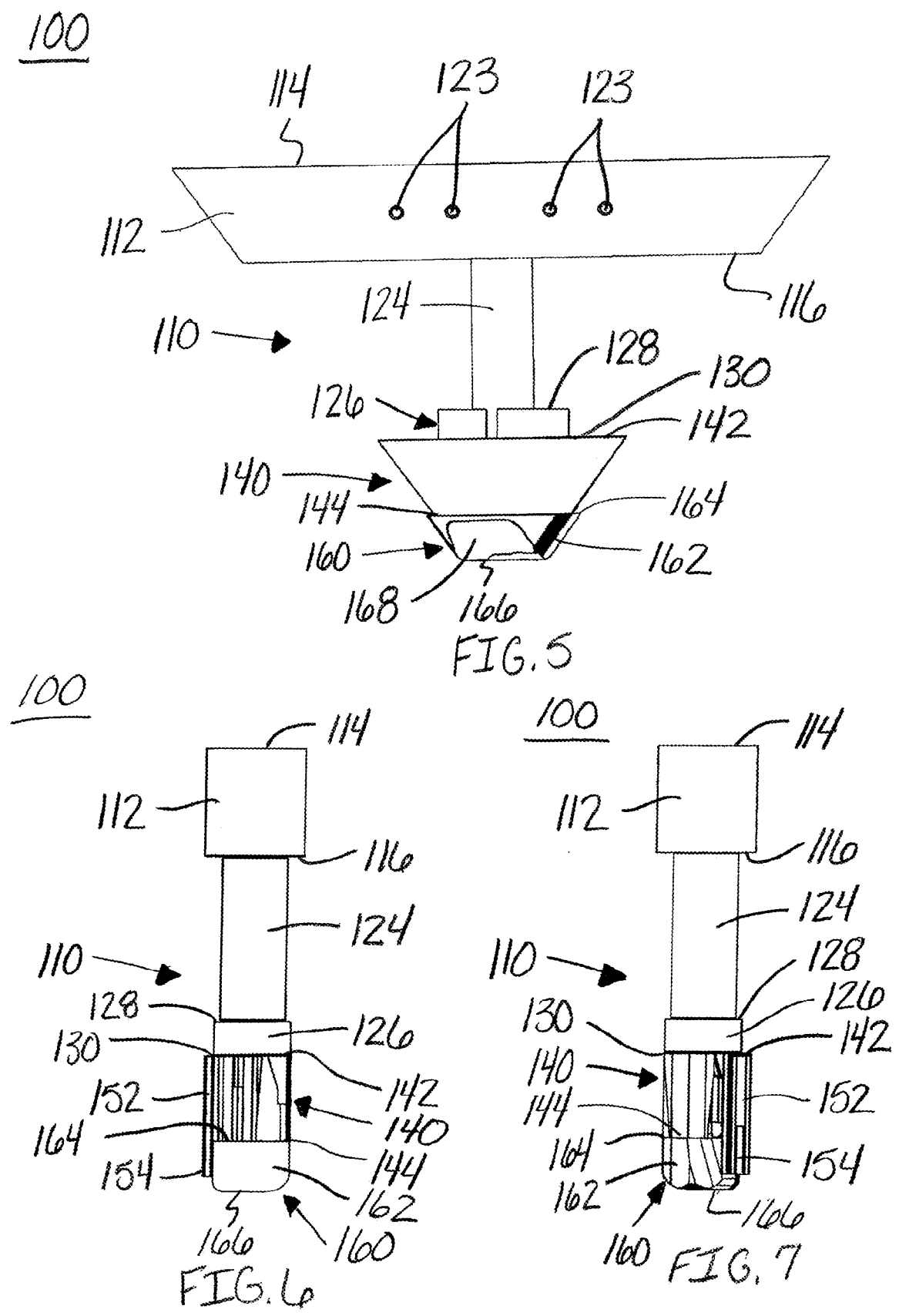
FIG. 5 is a second side view of the implant system of FIG. 1, in accordance with an aspect of the present invention.
FIG. 6 is a first end view of the implant system of FIG. 1, in accordance with an aspect of the present invention.
FIG. 7 is a second end view of the implant system of FIG. 1, in accordance with an aspect of the present invention.
Figure 8:
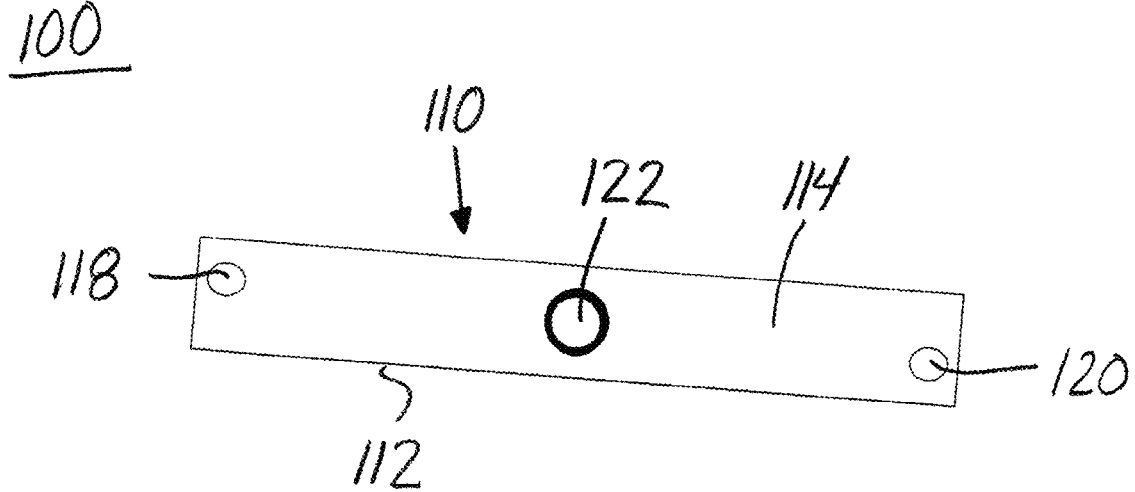
FIG. 8 is a top view of the implant of FIG. 1, in accordance with an aspect of the present invention.
Figure 9:
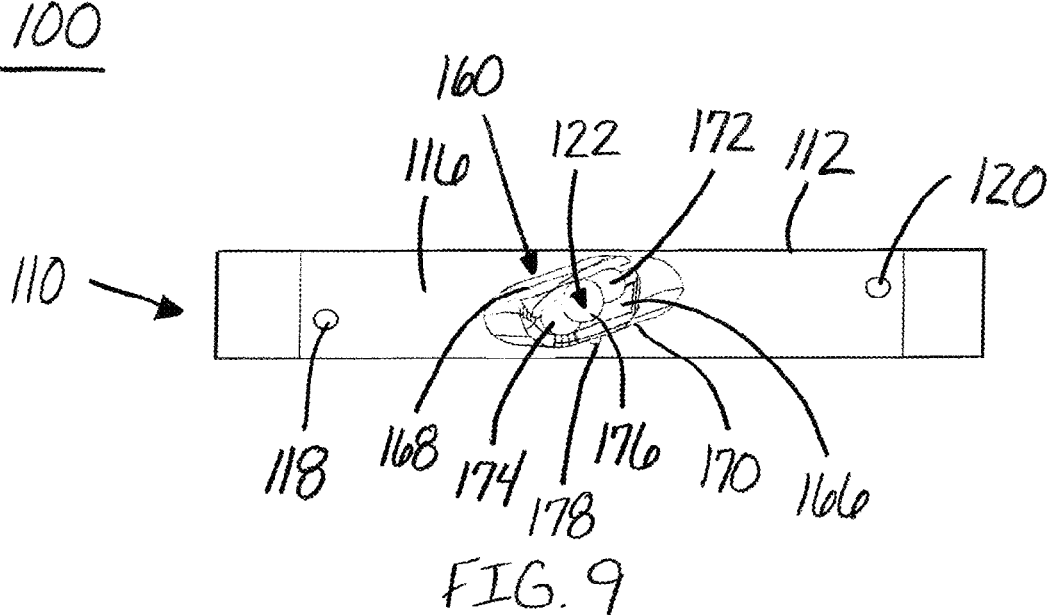
FIG. 9 is a bottom view of the implant of FIG. 1, in accordance with an aspect of the present invention.
Figure 10:
FIG. 10 is a top perspective view of an implant of the implant system of FIG. 1, in accordance with an aspect of the present invention.
Figure 10:
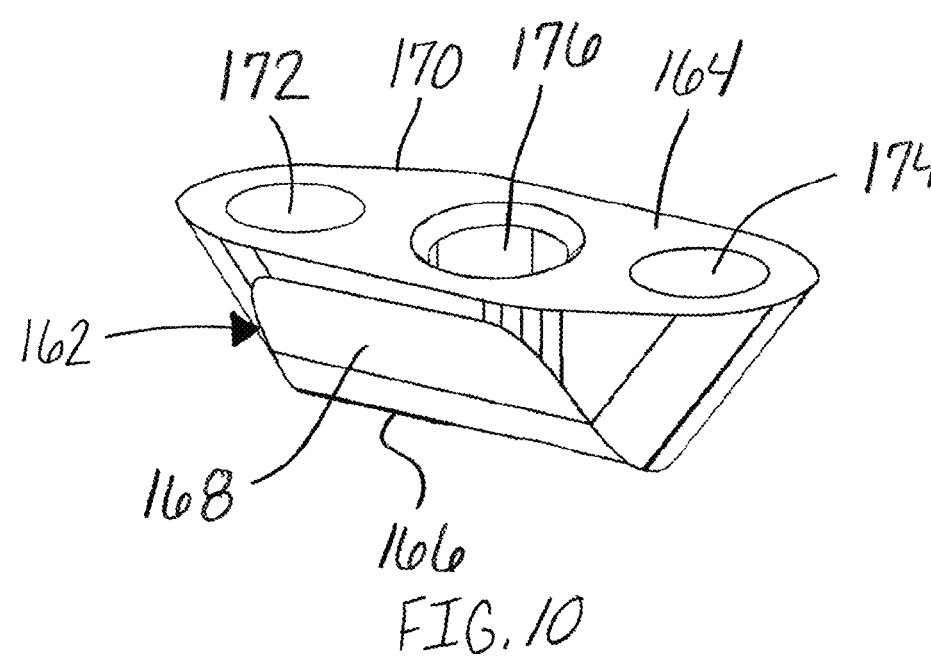
Figure 11:
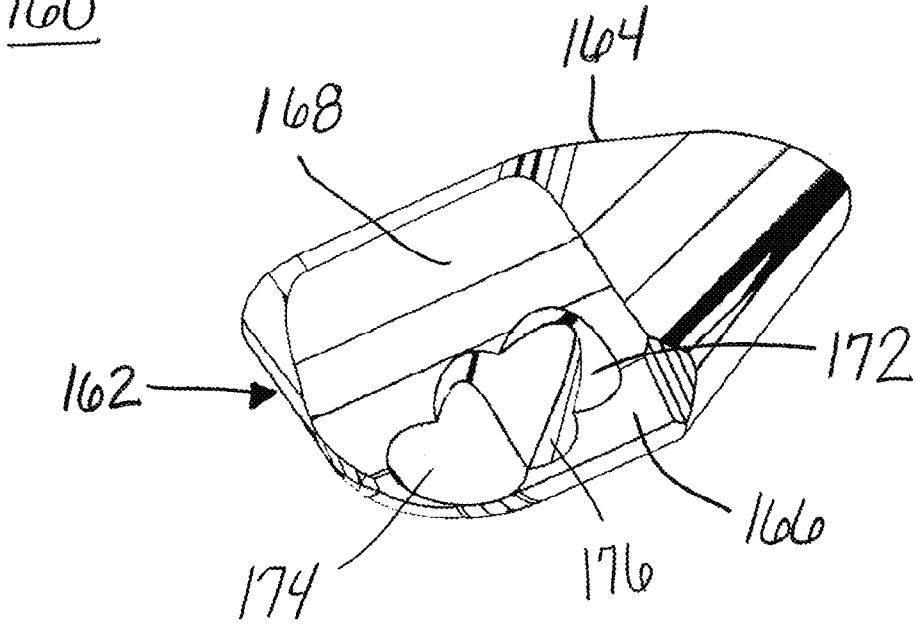
FIG. 11 is a bottom perspective view of the implant of FIG. 10, in accordance with an aspect of the present invention.
Figure 12:
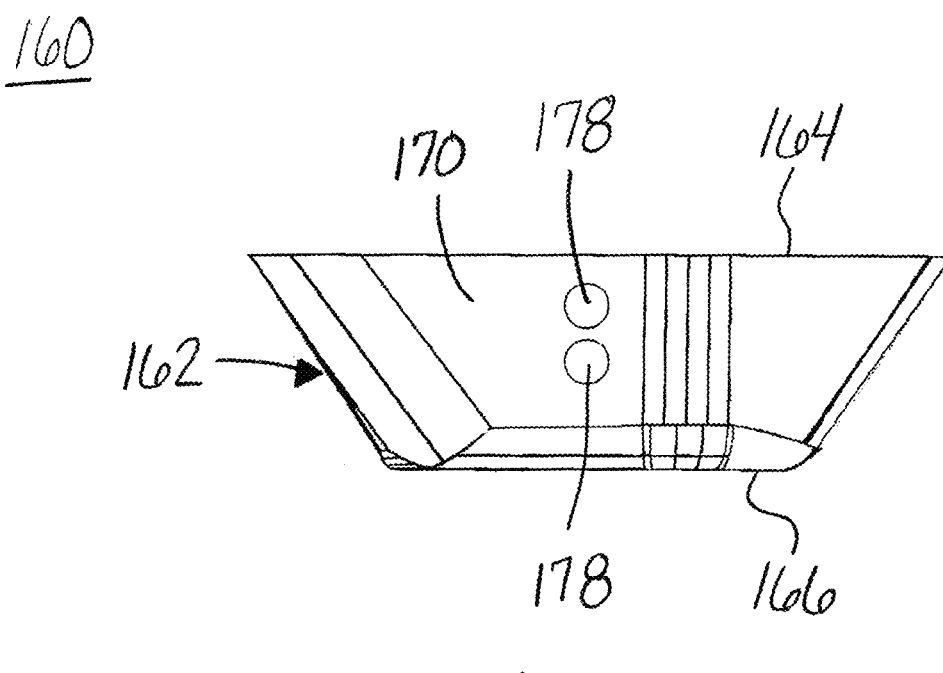
FIG. 12 is a second side view of the implant of FIG. 10, in accordance with an aspect of the present invention.
Figure 13:
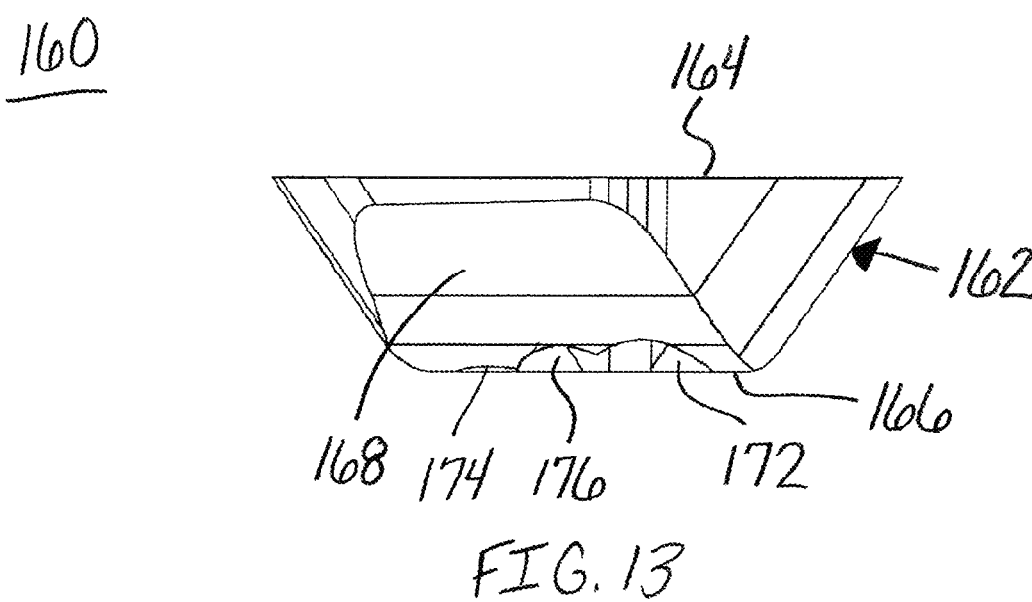
FIG. 13 is a first side view of the implant of FIG. 10, in accordance with an aspect of the present invention.
Figures 14, 15:
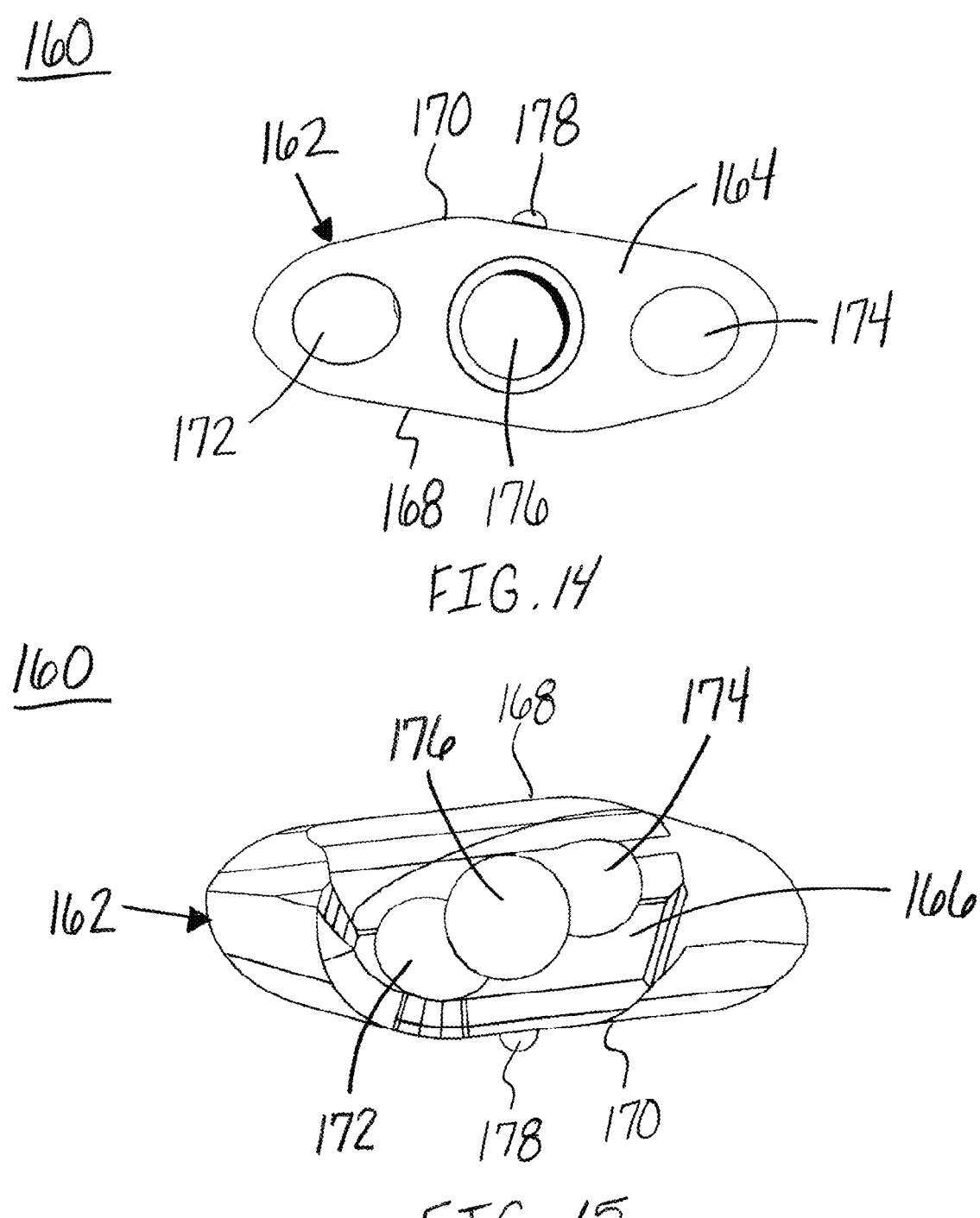
FIG. 14 is a top view of the implant of FIG. 10, in accordance with an aspect of the present invention.
FIG. 15 is a bottom view of the implant of FIG. 10, in accordance with an aspect of the present invention.
Figures 16, 17:
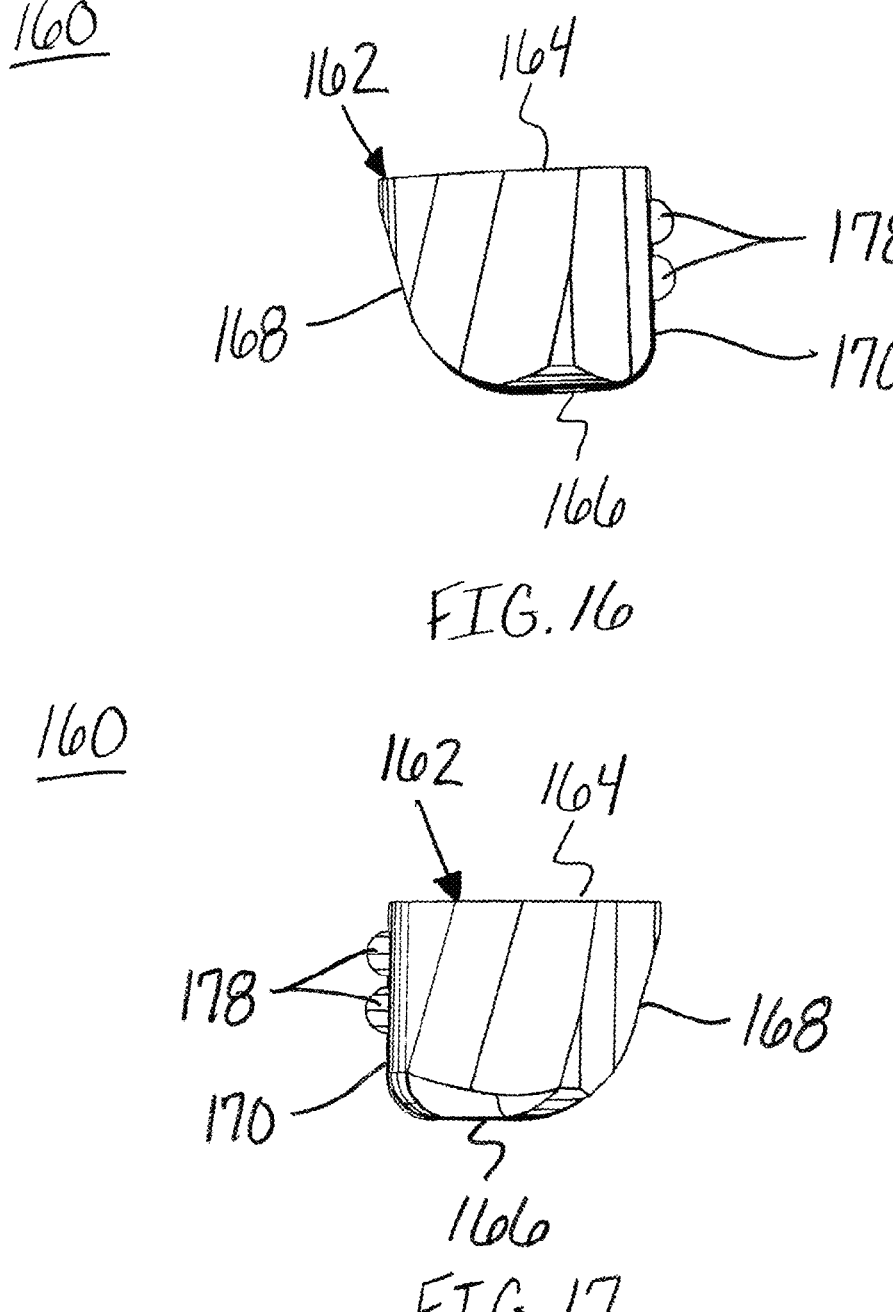
FIG. 16 is a first end view of the implant of FIG. 10, in accordance with an aspect of the present invention.
FIG. 17 is a second end view of the implant of FIG. 10, in accordance with an aspect of the present invention.

Generally stated, disclosed herein are bone fusion systems, implants, devices and instruments. Further, surgical methods for inserting the implants are discussed.

In this detailed description and the following claims, the words proximal, distal, anterior, posterior, medial, lateral, superior, inferior, cephalad and caudally are defined by their standard usage for indicating a particular part of a bone or implant according to the relative disposition of the natural bone or directional terms of reference. For example, "proximal" means the portion of an implant nearest the insertion instrument, while "distal" indicates the portion of the implant farthest from the insertion instrument. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure, "cephalad" means a direction toward the head and "caudally" means a direction toward the inferior part of the body.

Similarly, positions or directions may be used herein with reference to anatomical structures or surfaces. For example, as the current devices and methods are described herein with reference to use with the bones of the spine, the bones of the spine may be used to describe the surfaces, positions, directions or orientations of the devices, instrumentation and methods. Further, the devices and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the device and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the devices and methods, and the aspects, components, features and the like thereof, described herein with respect to a right side of the spine may be mirrored so that they likewise function with a left side of the spine and vice versa.

Referring to the drawings, wherein like reference numerals are used to indicate like or analogous components throughout the several views, and with particular reference to FIGS. 1-36 and 85, there is illustrated an exemplary embodiment of an implant system 100. The implant system 100 may include an insertion guide or cross bar guide tower 110, a locking block 140, and an implant 160, as shown in FIGS. 1-7. The insertion guide 110 may include, for example, a base member or top block 112, a coupling portion 126, and a connecting member 124 coupled to the base member 112 at a first end and the coupling portion 126 at a second end, as shown in FIGS. 1-7, 18-21 and 24-25. The insertion guide 110 and locking block 140 of the implant system 100 may be secured to the implant 160 during a surgical procedure to provide additional screw trajectory guidance from above the surgical incision.

Referring now to FIGS. 1-9 and 18-25, the insertion guide 110 may include a base member or top block 112 with a top surface 114 opposite a bottom surface 116. The base member 112 may also include a first opening 118 at a first end, a second opening 120 at a second end, and a through hole 122 positioned between the first opening 118 and the second opening 120. The first opening 118 may extend through the base member 112 from the top surface 114 to the bottom surface 116. The first opening 118 may have, for example, a first trajectory which may be angled in a first direction. The first opening 118 may also extend, for example, parallel to the angled first end of the base member 112. The second opening 120 may extend through the base member 112 from the top surface 114 to the bottom surface 116. The second opening 120 may have, for example, a second trajectory which may be angled in a second direction. The second direction of the second opening 120 may be opposite the first direction of the first opening 118. The first and second trajectories may be positioned to extend past each other to allow for the insertion of fasteners or screws (not shown) in a crossed or X-shaped arrangement. The second opening 120 may also extend, for example, parallel to the angled second end of the base member 112. The openings or guide wire through holes 118, 120 may be used to aid in alignment of the insertion guide or construct 110. In an alternative embodiment, the base member 112 may include slots or slot features (not shown in FIG. 1-9 or 18-25) extending into the openings 118, 120 in the cross bar guide or insertion guide 110. The slots or slot features (not shown) allow for the insertion guide or tower 110 to be separated from the implant, for example, implant 160, by releasing the guide wire (not shown).

The through hole 122 may extend through the base member 112 from the top surface 114 to the bottom surface 116. The through hole 122 may extend, for example, through the base member 112 perpendicular to the top and bottom surfaces 114, 116. As shown in FIGS. 1-5 and 18-21, the base member 112 may also include at least one hole 123. The at least one hole 123 may extend between the sides of the base member 112, for example, relatively perpendicular to the through hole 122 and relatively parallel to the top and bottom surfaces 114, 116. The at least one hole 123 may provide, for example, a point of reference for the surgeon for the position or location of the openings 145, 148. For example, the lateral holes 123 may align with the top surface or entrance to the openings 145, 148 and the medial holes 123 may align with the bottom surface or exit of the openings 145, 148. Although the at least one hole 123 is shown as through holes, it is also contemplated that the holes 123 may be recesses, grooves, machine markings, and the like to provide a point of reference for the surgeon. Further, the openings 123 may receive a pin to provide additional visual reference point for determining the position of the locking block 140 and implant 160. The top surface 114 may have, for example, a length larger than the length of the bottom surface 116. The base member 112 may have, for example, a generally trapezoidal cross-sectional shape forming, for example, a trapezoidal prism. Alternative polygonal shapes are also contemplated including, for example, at least, rectangles, parallelograms, and the like.

As shown in FIGS. 2-7, 19-21 and 24-25, the connecting member 124 may have a first end and a second end. The first end of the connecting member 124 may be coupled to the base member 112 and aligned with the through hole 122. The second end of the connecting member 124 may be coupled to the coupling portion 126. The through hole 122 continues through the connecting member 124 and the coupling portion 126 and is configured to receive a handle member (not shown). The handle member (not shown) may be similar to the handle member 510, as described in greater detail below with reference to FIGS. 75-81, including a gripping portion and an at least partially threaded rod for engaging an implant 160, 200, 250, 400, 450 for insertion into a patient.

Figures 18, 19:
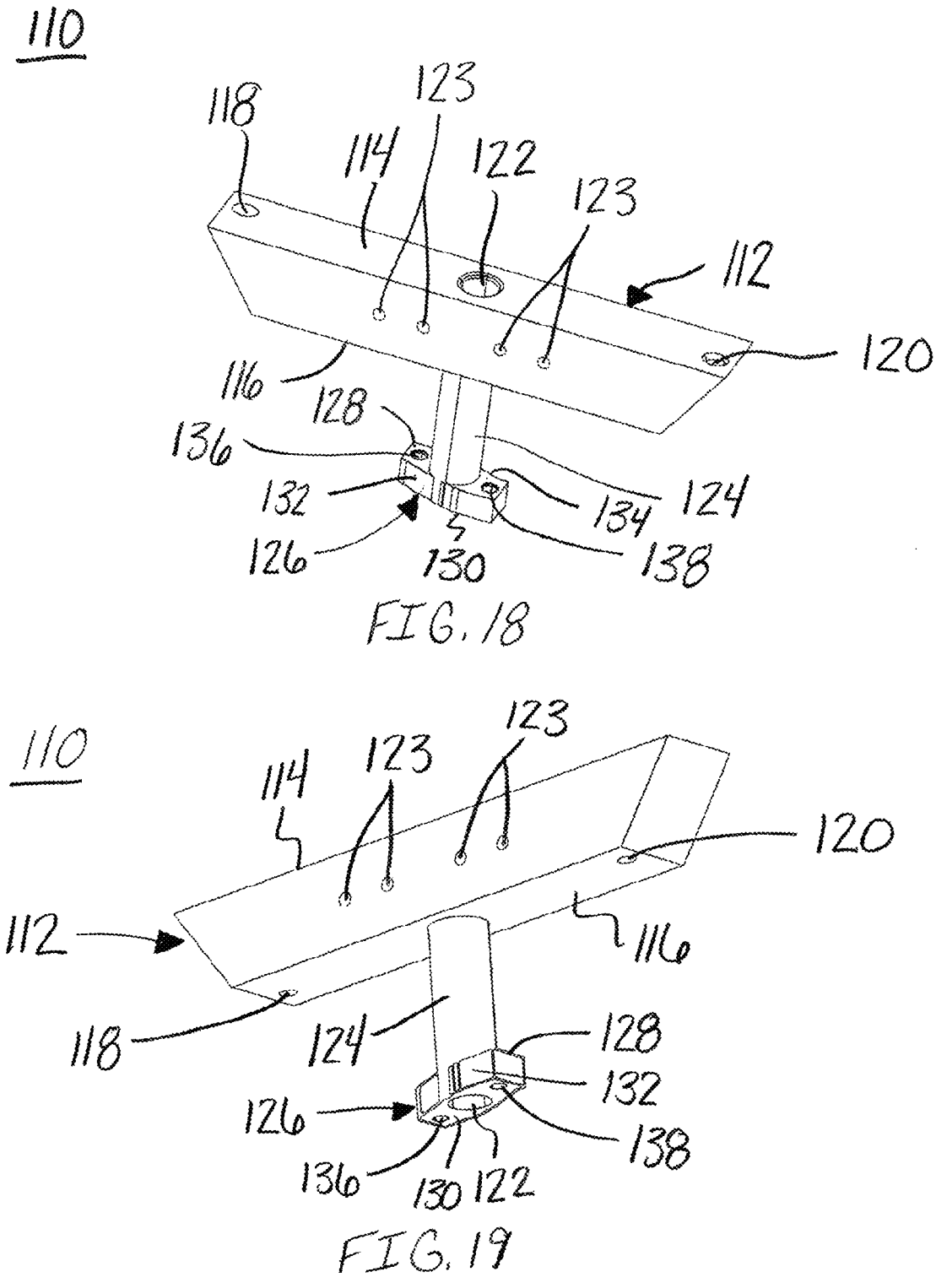
FIG. 18 is a top perspective view of an insertion guide of the implant system of FIG. 1, in accordance with an aspect of the present invention.
FIG. 19 is a side perspective view of the insertion guide of FIG. 18, in accordance with an aspect of the present invention.
Figure 20:
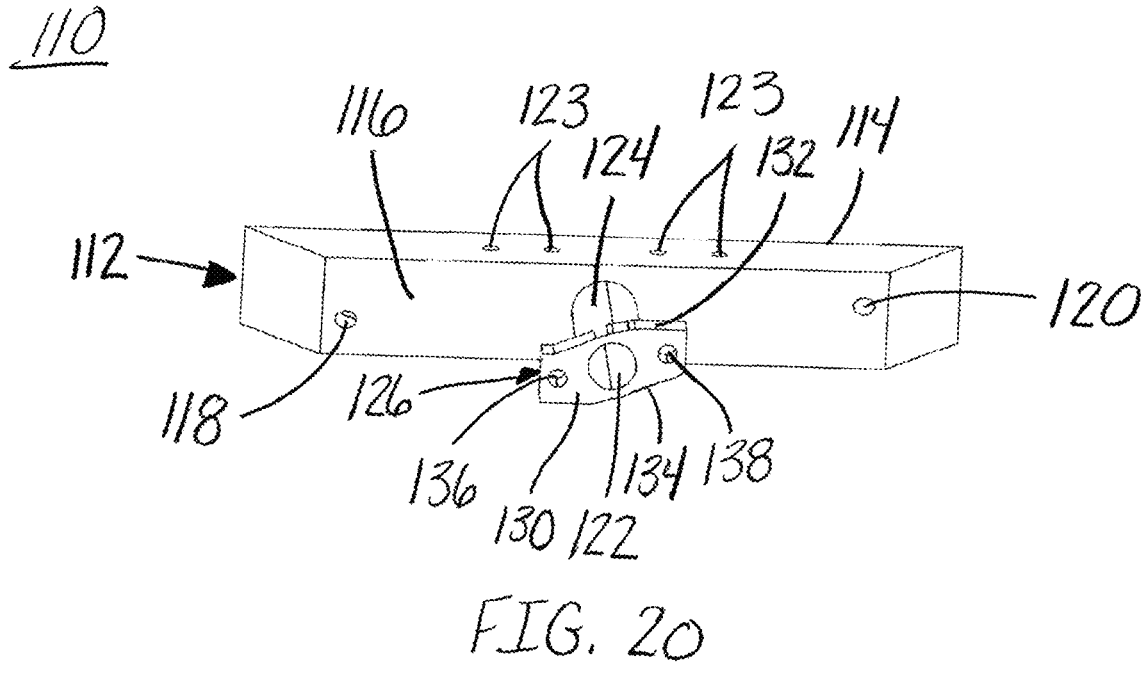
FIG. 20 is a bottom perspective view of the insertion guide of FIG. 18, in accordance with an aspect of the present invention.
Figure 21:
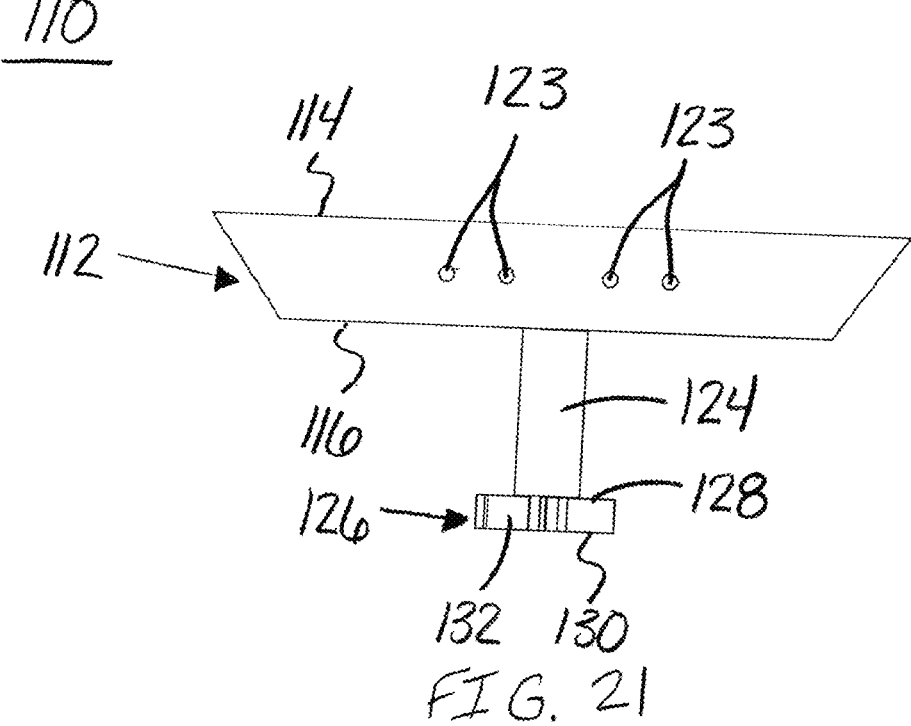
FIG. 21 is a side view of the insertion guide of FIG. 18, in accordance with an aspect of the present invention.
Figure 22:
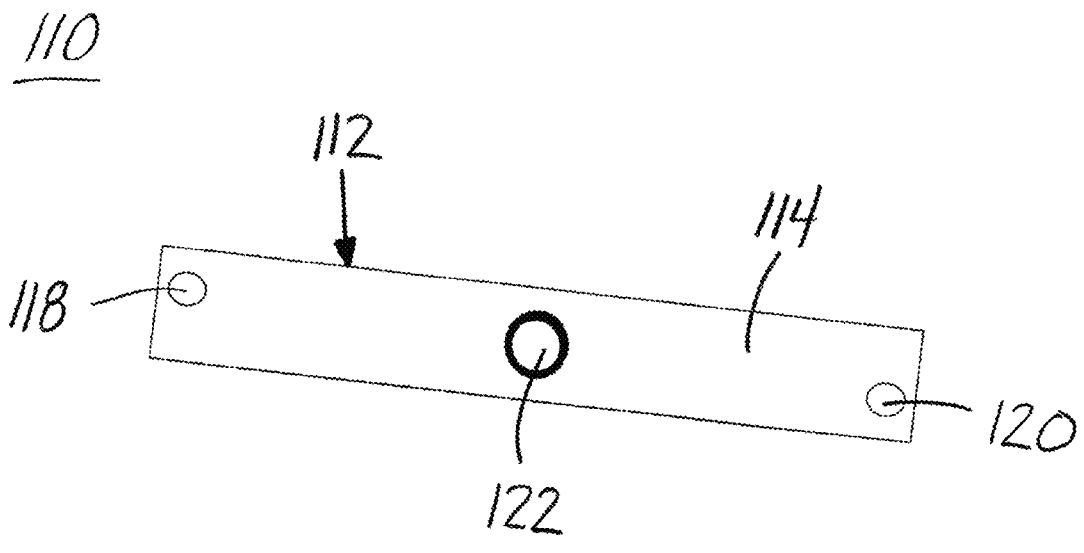
FIG. 22 is a top view of the insertion guide of FIG. 18, in accordance with an aspect of the present invention.
Figure 23:
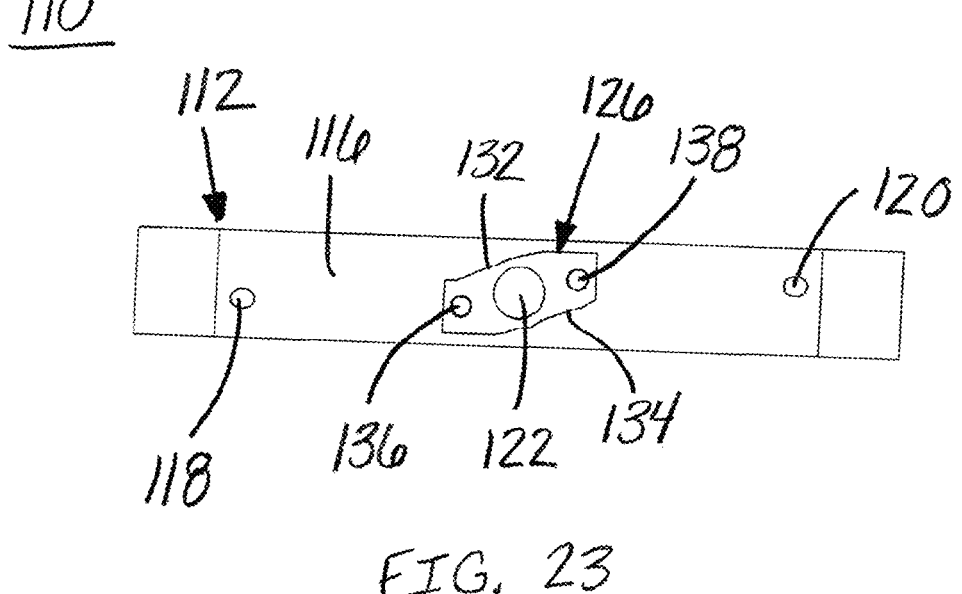
FIG. 23 is a bottom view of the insertion guide of FIG. 18, in accordance with an aspect of the present invention.
Figures 24, 25:
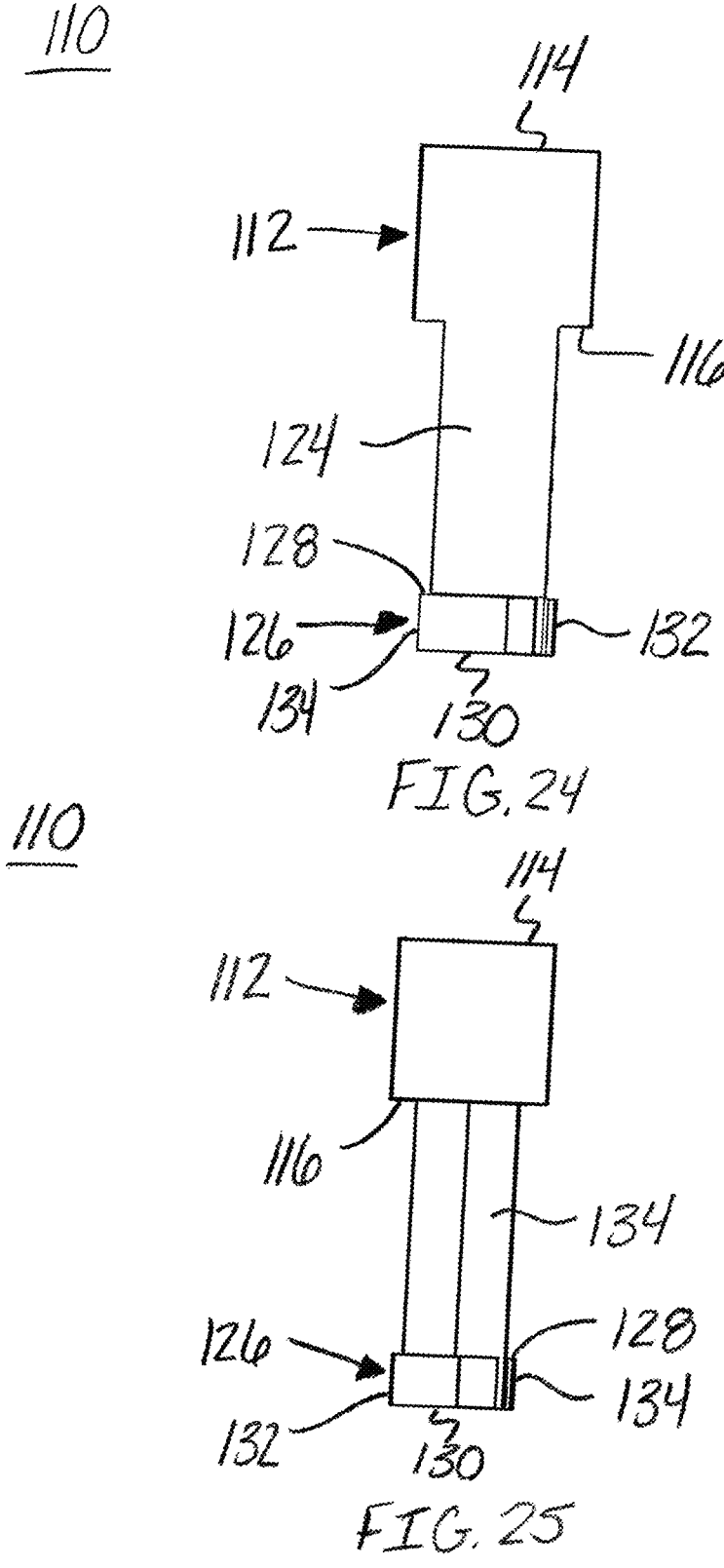
FIG. 24 is a first end view of the insertion guide of FIG. 18, in accordance with an aspect of the present invention.
FIG. 25 is a second end view of the insertion guide of FIG. 18, in accordance with an aspect of the present invention.
Figure 26:
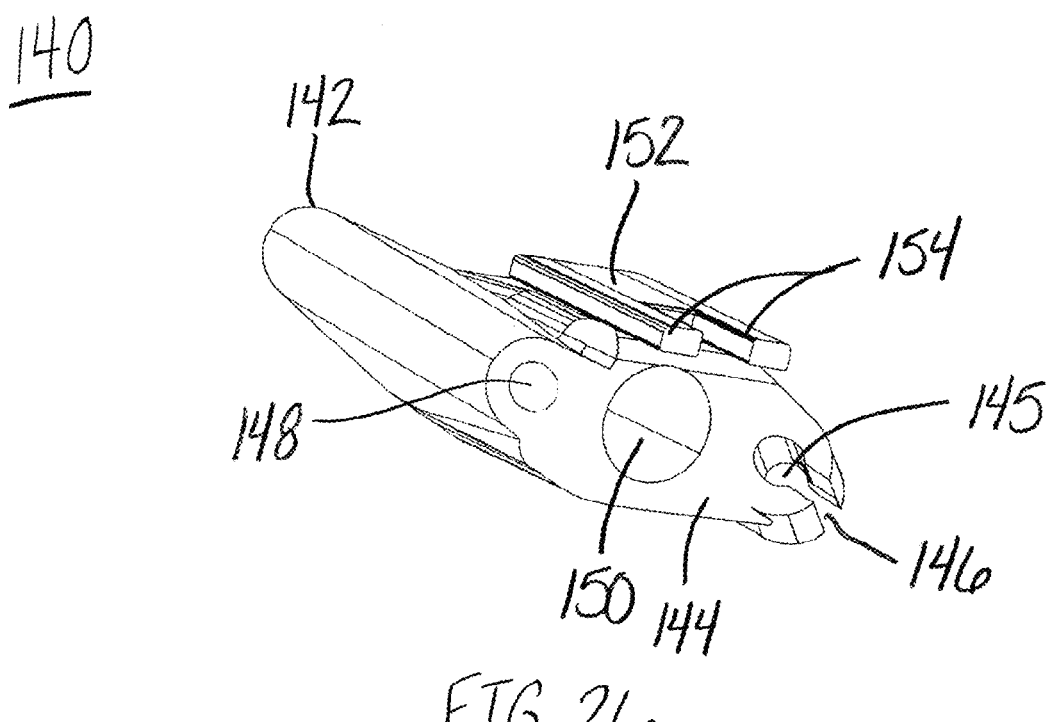
FIG. 26 is a bottom, perspective view of a locking block of the implant system of FIG. 1, in accordance with an aspect of the present invention.

The coupling portion 126 may include a top surface 128 opposite a bottom surface 130 and a first side 132 opposite a second side 134, as shown in at least FIGS. 18-20. The coupling portion 126 may also include a first opening 136 positioned at a first end and a second opening 138 at a second end. The first and second openings 136, 138 may extend between the top surface 128 and the bottom surface 130. The first and second openings 136, 138 may also extend, for example, generally perpendicular to the top and bottom surfaces 128, 130. The first opening 136 may be, for example, offset or angled in a first direction relative to a longitudinal axis of the base member 112, as shown in FIG. 23. The second opening 138 may be, for example, offset or angled in a second direction relative to a longitudinal axis of the base member 112, as also shown in FIG. 23. The first and second openings 136, 138 may be sized and shaped or configured to receive a fastener or fastening mechanism (not shown) to secure the locking block 140 to the coupling portion 126, as shown in FIGS. 1-7. The sides 132, 134 of the coupling portion 126 may be, for example, curved or slightly "S" shaped as shown in FIG. 23. The coupling portion 126 may be, for example, angled relative to the longitudinal axis of the base member 112.

As shown in FIGS. 1-7, 9, and 26-36, the locking block 140 includes a top surface 142 opposite a bottom surface 144. The locking block 140 may include a first opening 145 at a first end and a second opening 148 at a second end. The first and second openings 145, 148 may extend from the top surface 142 to the bottom surface 144. The locking block 140 may also include a slot 146 extending from the exterior surface at the first end into the first opening 145 and from the top surface 142 to the bottom surface 144, as shown in FIGS. 26, 28, 33, 35 and 36. The first opening 145 may also extend, for example, parallel to the angled first end of the locking block 140. The first opening 145 may have, for example, a first trajectory which may be angled in a first direction. The first trajectory of the locking block 140 may, for example, correspond to the first trajectory of the base member 112 to allow for a Jamshidi needle, k-wire, screw, or the like to be inserted through the first opening 118 of the base member 112 and the first opening 145 of the locking block 140. The second opening 148 may also extend, for example, parallel to the angled second end of the locking block 140. The second opening 148 may have, for example, a second trajectory which may be angled in a second direction. The second trajectory of the locking block 140 may, for example, correspond to the second trajectory of the base member 112 to allow for a Jamshidi needle, k-wire, screw, or the like to be inserted through the second opening 148 of the base member 112 and the second opening 148 of the locking block 140. The first and second trajectories may be selected, for example, to correspond to the desired placement in a patient's facet and/or pedicle. In an embodiment, the openings 145, 148 may be, for example, angled approximately 65-85 degrees from a top surface 142 of the locking block 140, however, additional angles are also contemplated to correspond to variations in patient anatomy.

With continued reference to FIGS. 1-7, 9, 26-28, and 35-36, the locking block 140 may also include a center opening or through hole 150. The through hole 150 is configured to allow a handle member (not shown) to pass through the locking block 140 and engage an implant, for example, the implant 160. The through hole 150 may extend, for example, through the locking block 140 generally perpendicular to the top and bottom surfaces 142, 144. The locking block 140 may further include an alignment member 152 positioned on a side of the locking block 140, as shown in FIGS. 26-29, 32 and 34-36. The alignment member 152 may include at least one extension member 154 extending from the alignment member 152 past the bottom surface 144 of the locking block 140, as shown in FIGS. 28-34. The at least one extensions member 154 may be, for example, multiple fork extensions. The at least one extension member 154 may be used to accurately locate the lateral aspect of the insertion guide or device 110.

Figure 27:
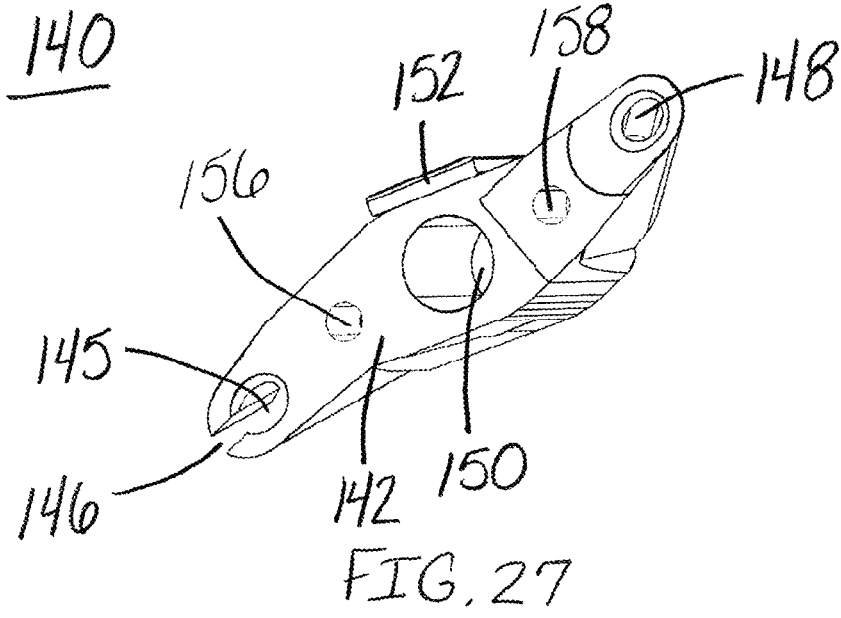
FIG. 27 is a top, perspective view of the locking block of FIG. 26, in accordance with an aspect of the present invention.
Figures 28, 29:
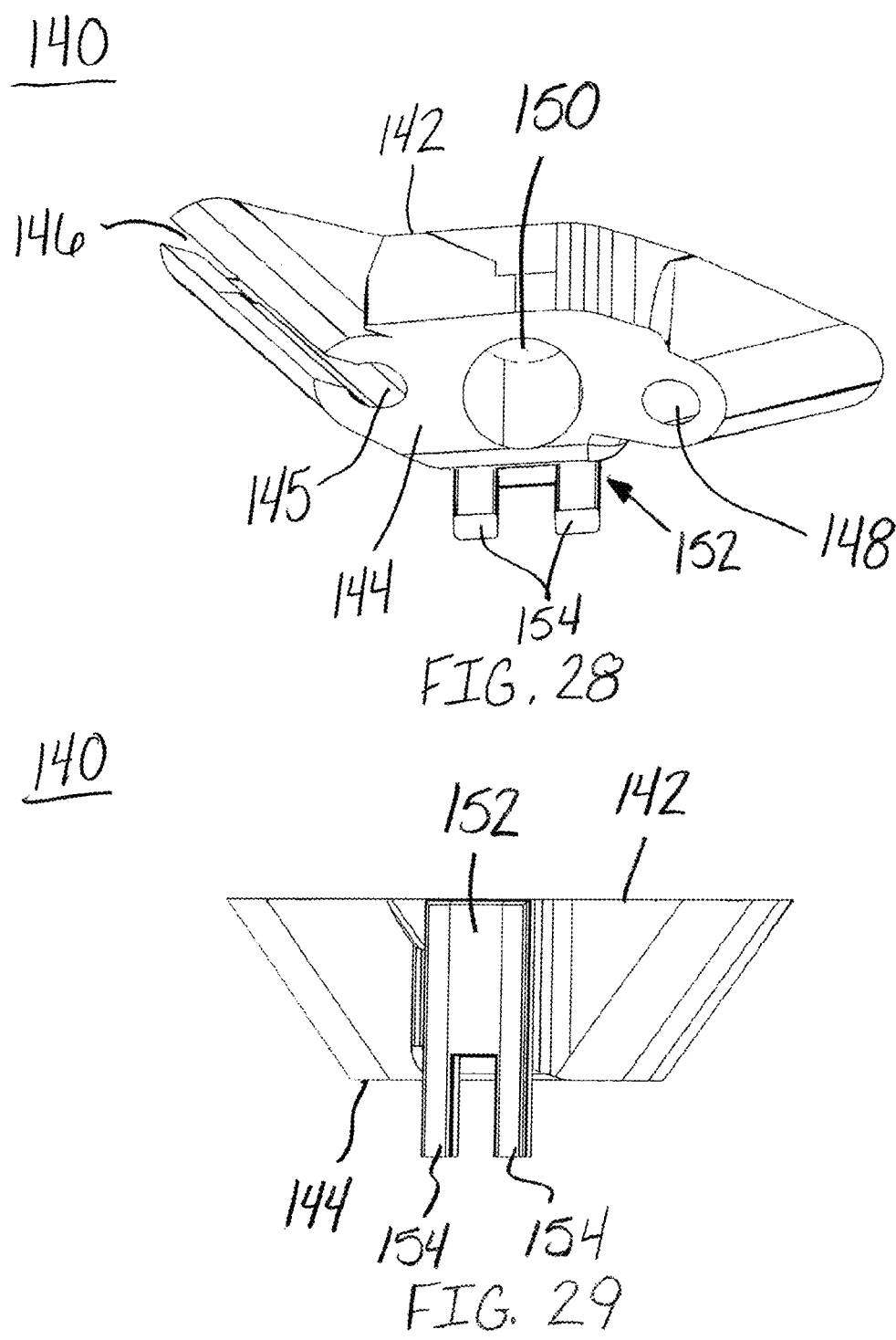
FIG. 28 is a bottom, perspective view of the locking block of FIG. 26, in accordance with an aspect of the present invention.
FIG. 29 is a second side view of the locking block of FIG. 26, in accordance with an aspect of the present invention.
Figure 30:
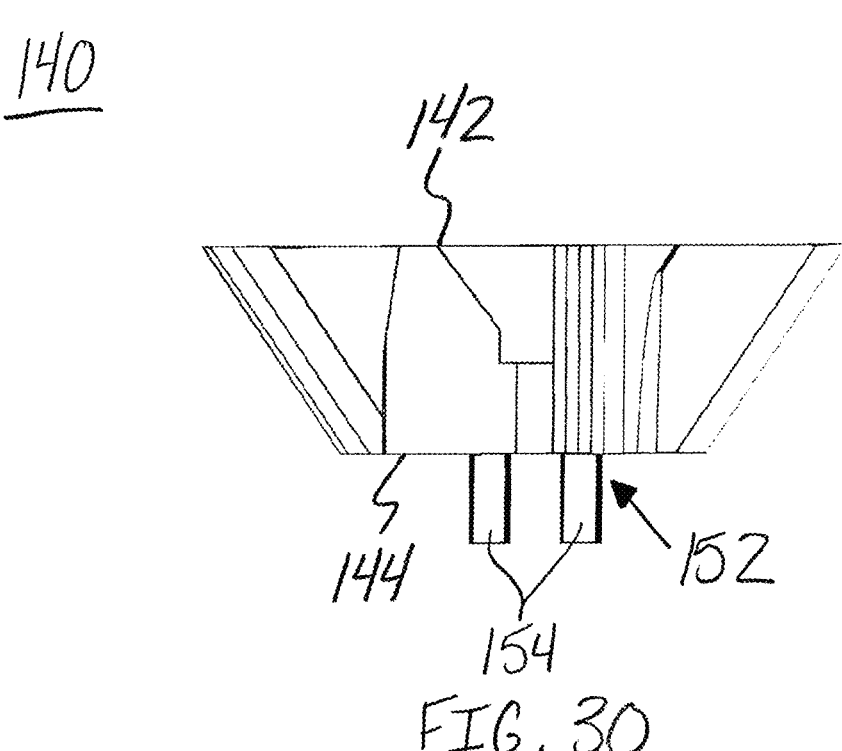
FIG. 30 is a first side view of the locking block of FIG. 26, in accordance with an aspect of the present invention.
Figure 31:
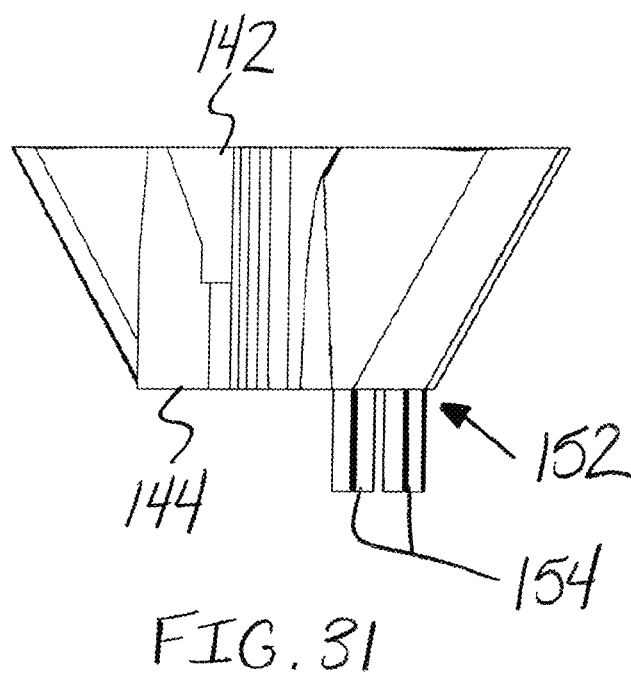
FIG. 31 is a side view of the locking block of FIG. 26, in accordance with an aspect of the present invention.
Figures 32, 33:
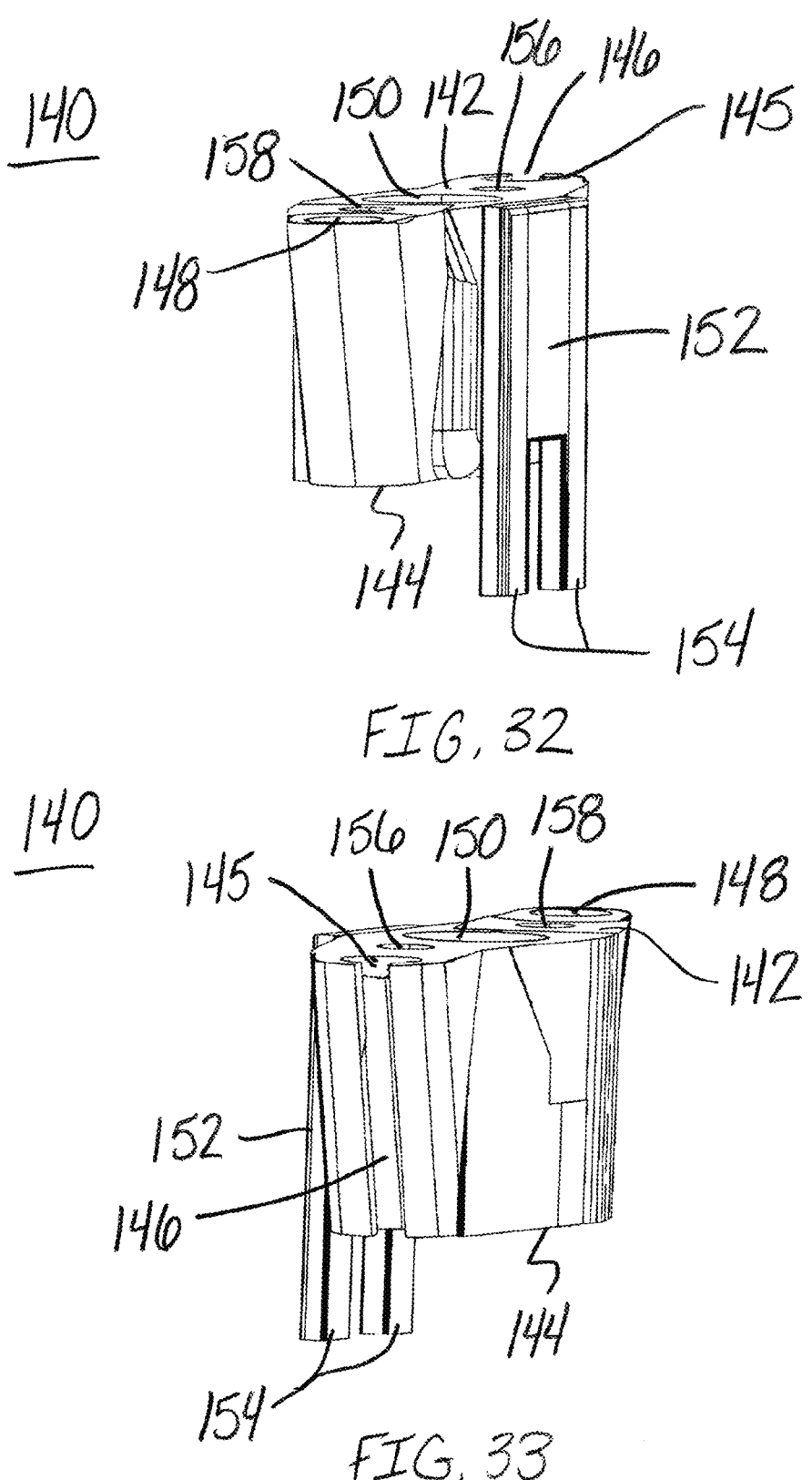
FIG. 32 is a first end view of the locking block of FIG. 26, in accordance with an aspect of the present invention.
FIG. 33 is a first side perspective view of the locking block of FIG. 26, in accordance with an aspect of the present invention.
Figures 34, 35:
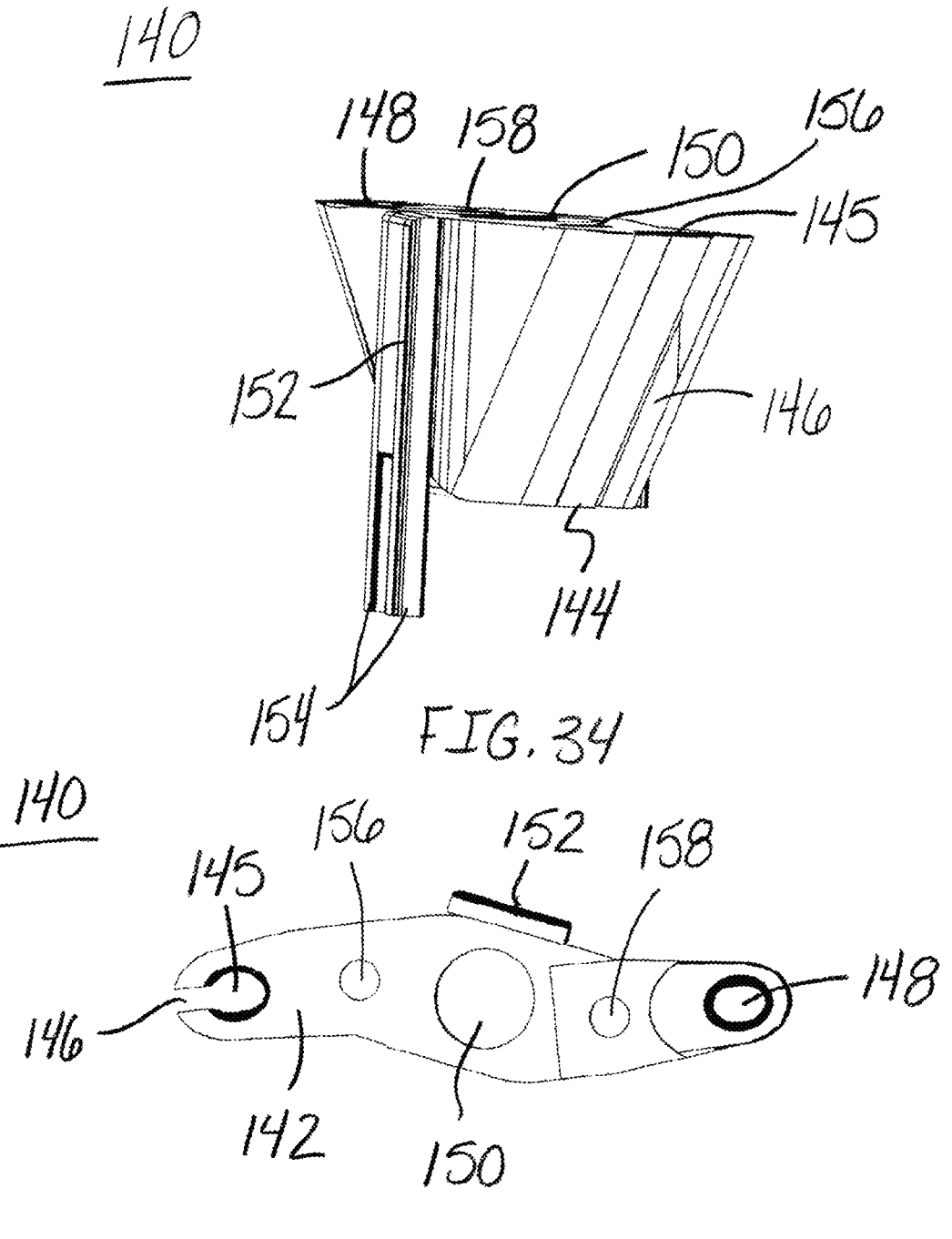
FIG. 34 is a second side perspective view of the locking block of FIG. 26, in accordance with an aspect of the present invention.
FIG. 35 is a top view of the locking block of FIG. 26, in accordance with an aspect of the present invention.
Figures 36, 37:
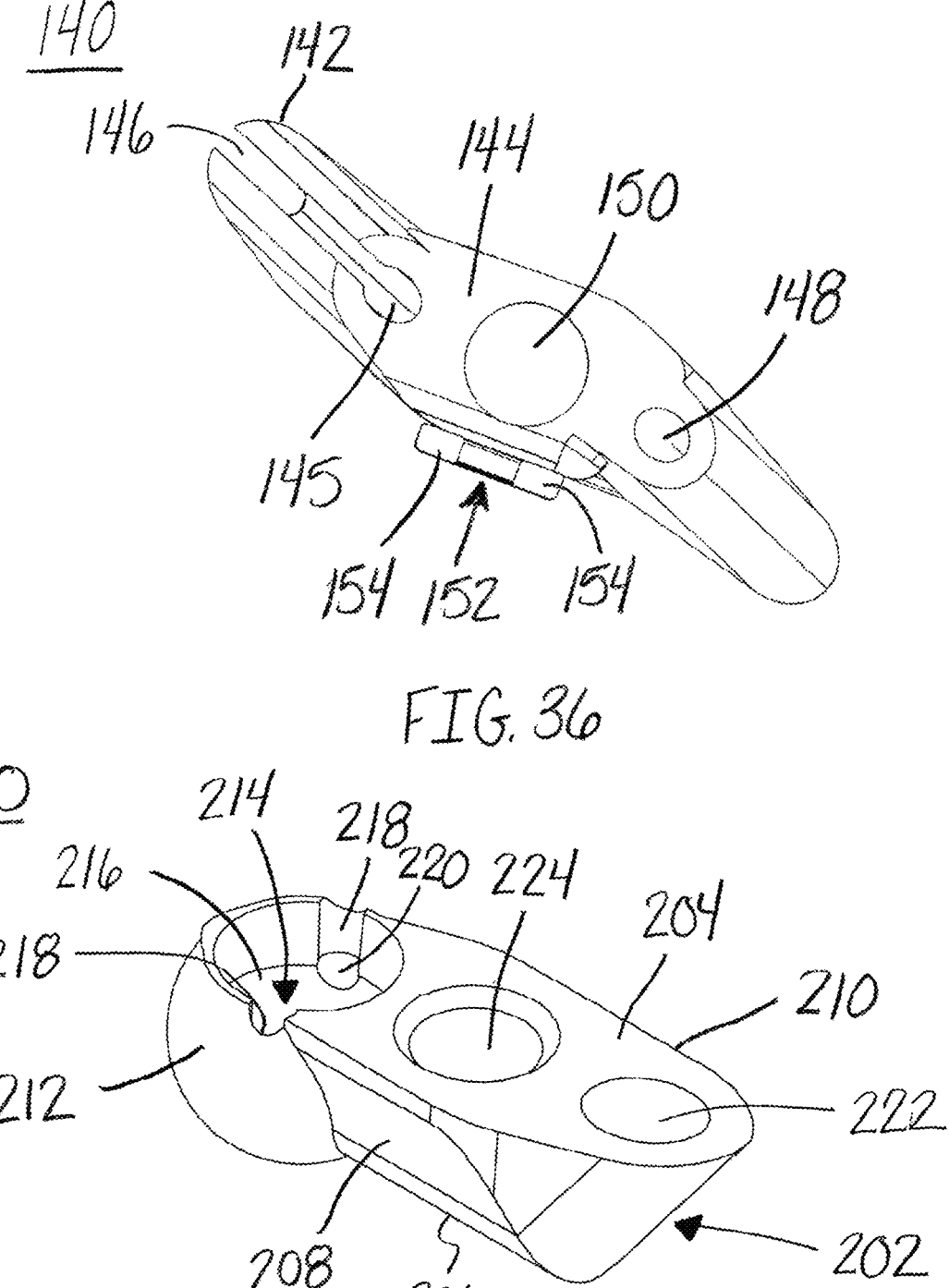
FIG. 36 is a bottom view of the locking block of FIG. 26, in accordance with an aspect of the present invention.
FIG. 37 is a perspective view of a body of another implant, in accordance with an aspect of the present invention.

The locking block 140 may also include at least one securement opening 156, 158 extending into a top surface 142 of the locking block 140, as shown in FIGS. 27 and 35. The at least one securement opening 156, 158 may be, for example, a first securement opening 156 and a second securement opening 158. As shown in FIGS. 27 and 35, the first securement opening 156 may be positioned, for example, between the first opening 145 and the center opening 150. The first securement opening 156 may also be positioned on the locking block 150 to align with the first opening 136 of the coupling portion 126 to receive a fastener or fastener member (not shown) and secure the locking block 140 to the coupling portion 126, as shown in FIGS. 1-7. The second securement opening 158 may be positioned, for example, between the second opening 148 and the center opening 150. The second securement opening 158 may also be positioned on the locking block 150 to align with the second opening 138 of the coupling portion 126 to receive a fastener or fastener member (not shown) and secure the locking block 140 to the coupling portion 126, as shown in FIGS. 1-7.

The cross bar guide tower or insertion guide 110 may couple to the connector device or implant 160 while placing the trajectory devices (not shown) or fixation device insertion instruments (not shown), for example, a Jamshidi needle or k-wires. The top block or base member 112 of the instrument 110 incorporates guide holes or openings 118, 120 to facilitate the insertion of a guide device (not shown) which may be, for example, a Jamshidi needle or similar device to aid in the delivery of a guide wire for subsequent surgical activities including passing the fixation members, bone screws, fasteners, pegs, pins, and/or springs through the locking block 140 to their final position.

Figures 72, 73, 74:
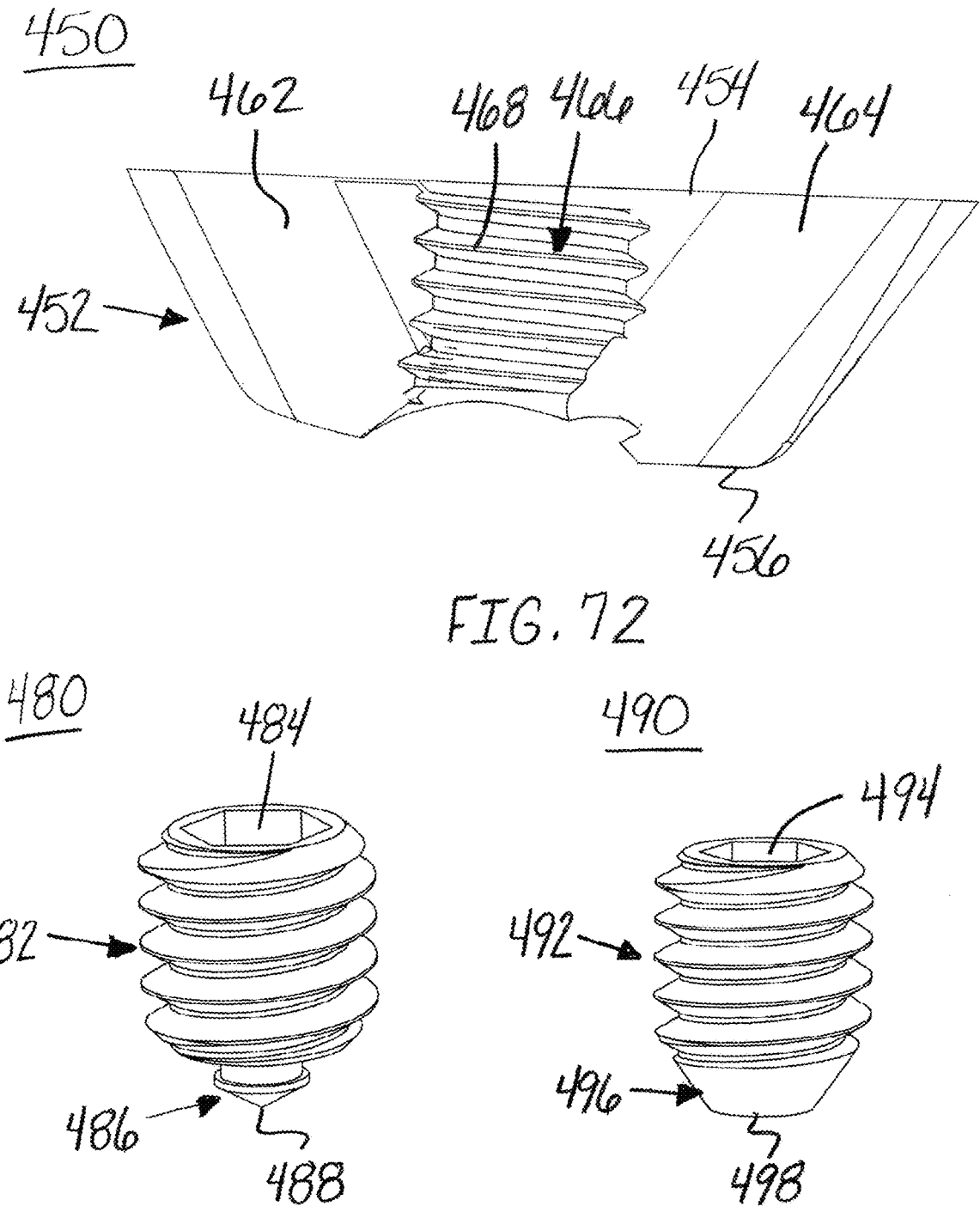
FIG. 72 is a cross sectional view of the implant of FIG. 67 taken along line 72-72 in FIG. 70, in accordance with an aspect of the present invention.
FIG. 73 is a side perspective view of a locking screw, in accordance with an aspect of the present invention.
FIG. 74 is a side perspective view of another locking screw, in accordance with an aspect of the present invention.

A bone fusion device may be, for example, a four piece construct including an implant or connector device 160, as shown in FIGS. 10-17, two cannulated fasteners, fixation screws, bone screws, fixation members, fasteners, pegs, pins, and/or springs (not shown), and a central locking screw 480, 490, as shown in FIGS. 73-74. The two cannulated bone screws and central locking screw 480, 490 are configured or sized and shaped to provide a non-co-planar screw trajectory while allow for or achieving fusion. The implant 160 is sized and shaped or configured to assist with guiding the two screws into a patient's vertebrae. For example, the implant 160 may be used to guide the fixation screws (not shown) into divergent aspects of the vertebrae and to lock the two divergent screws or other fasteners into place. Specifically, the implant 160 may be used to guide a first fastener into a patient's pedicle and a second fastener into the patient's facet/pedicle of a vertebrae, or vice versa.

Referring now to FIGS. 1-7, 9, and 10-17, the implant or connector device 160 includes a body 162 with a top surface 164 opposite a bottom surface 166 and a first side 168 opposite a second side 170. The implant 160 may be, for example, a three-dimensional misshapen parallelogram which may be rounded on the ends, bottom surface and at least one side. The length of the top surface 164 may be, for example, longer than the length of the bottom surface 166 forming tapered ends. The implant 160 may have a radius on the outer diameter of the first or medial side 168 to accommodate the spinous process. In one embodiment, for example, the first side 168 of the implant 160 may have approximately a 15 degree angle transitioning into a 10 mm radius, although other angles and radius dimensions are contemplated. The implant 160 may also be, for example, shaped to have a low profile to avoid bone and tissue impingement. In addition, the implant 160 may be, for example, slightly thicker on the second or lateral outer side 170 and the outer ends (i.e. cephalad end and caudal end). The body 162 of the implant 160 may also have, for example, additional smoothing or rounded edges to accommodate a feature of a patient's anatomy while maintaining the necessary wall thickness in critical areas of the body 162 to maintain strength while reducing the incident of bone or tissue impingement.

As shown in FIGS. 10-11 and 14-15, the implant 160 may also contain a first channel or hole 172 and a second channel or screw hole 174. The first hole 172 may receive, for example, fixation members, fasteners, screws, pegs, pins, springs and the like as known by one of ordinary skill in the art. The fixation members, fasteners, screws, pegs, and pins may be, for example smooth or threaded. The first hole 172 may be, for example, angled at a first trajectory as the hole 172 extends from a top surface 164 to a bottom surface 166. The first hole 172 may be oriented, for example, on the caudal end for guiding a Jamshidi needle, k-wire, screw, or the like into the trajectory for placement in the pedicle. The second hole 174 may receive, for example, fixation members, fasteners, screws, pegs, pins, springs and the like as known by one of ordinary skill in the art. The fixation members, fasteners, screws, pegs, and pins may be, for example smooth or threaded. The second hole 174 may be, for example, angled at a second trajectory as the hole 174 extends from a top surface 164 to a bottom surface 166. The second hole 174 may be oriented, for example, on the cephalad end for guiding a Jamshidi needle, k-wire, screw, or the like into the desired facet/pedicle trajectory. In one embodiment, for example, the facet/pedicle trajectory enters in the cephalad channel 174 and moves in a caudal direction and the pedicle trajectory enters in the caudal channel 172 and moves in a cephalad direction. The implant 160 may also contain a center channel or locking opening 176 positioned, for example, between the first screw hole 172 and the second screw hole 174, as shown in FIGS. 10-11 and 14-15. The center channel 176 may be, for example, sized and shaped or configured to receive a fastener, for example, a set screw 480, 490, as shown in FIGS. 73 and 74. The fastener 480, 490 may be used to place pressure on the screws (not shown) inserted through the holes 172, 174 and into the facet/pedicle and/or pedicle, thereby securing or locking the bone fusion device. In addition, the implant 160 may include at least one lateral side indicator 178, as shown in FIGS. 12 and 14-17. The at least one lateral side indicator 178 may be, for example, at least one protrusion, extension or a like feature extending away from a side of the body 162 or alternatively, a slot, recess, machine marking or a like feature inset into the side of the body 162, to indicate the lateral side of the implant 160. Further, the at least one lateral side indicator 178 may further designate whether the implant 160 is a left or right implant.

Figure 38:
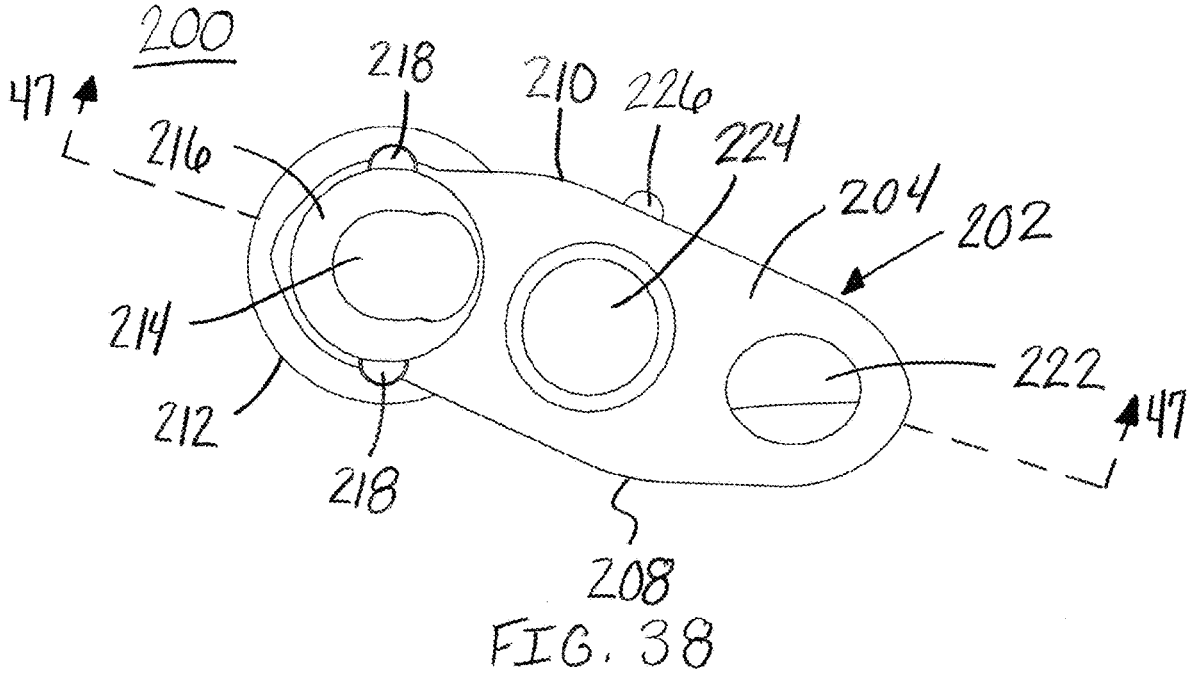
FIG. 38 is a top view of the body of FIG. 37, in accordance with an aspect of the present invention.
Figure 39:
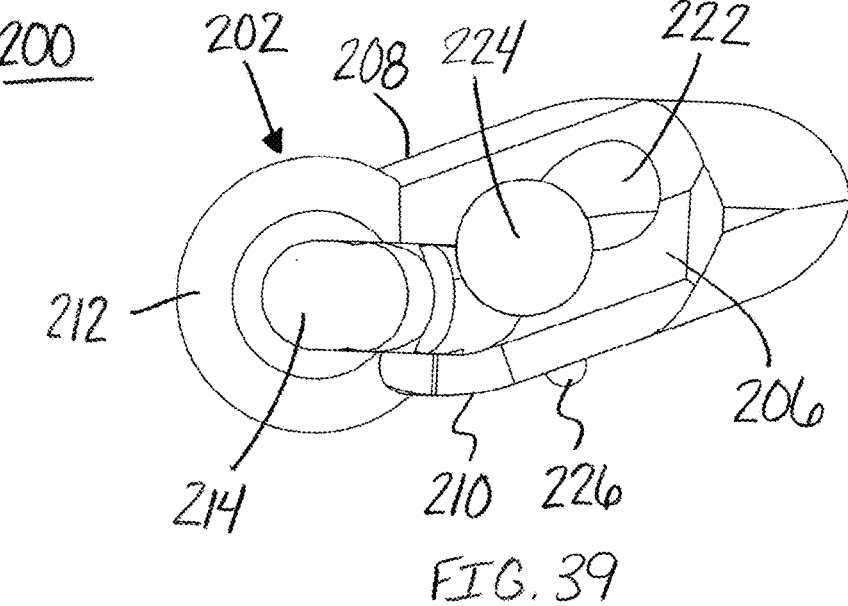
FIG. 39 is a bottom view of the body of FIG. 37, in accordance with an aspect of the present invention.
Figures 40, 41:
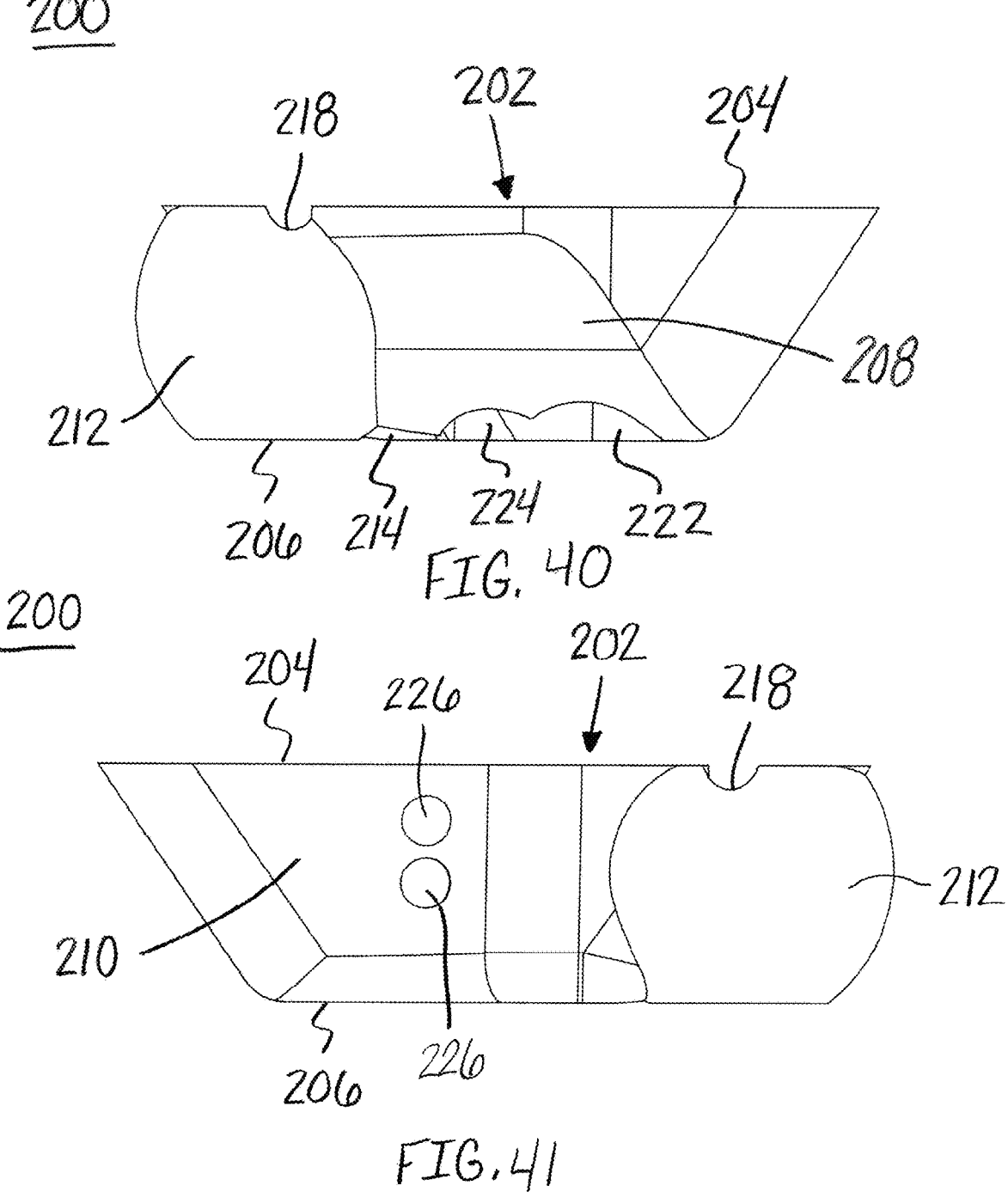
FIG. 40 is a first side view of the implant of FIG. 37, in accordance with an aspect of the present invention.
FIG. 41 is a second side view of the implant of FIG. 37, in accordance with an aspect of the present invention.
Figures 42, 43:
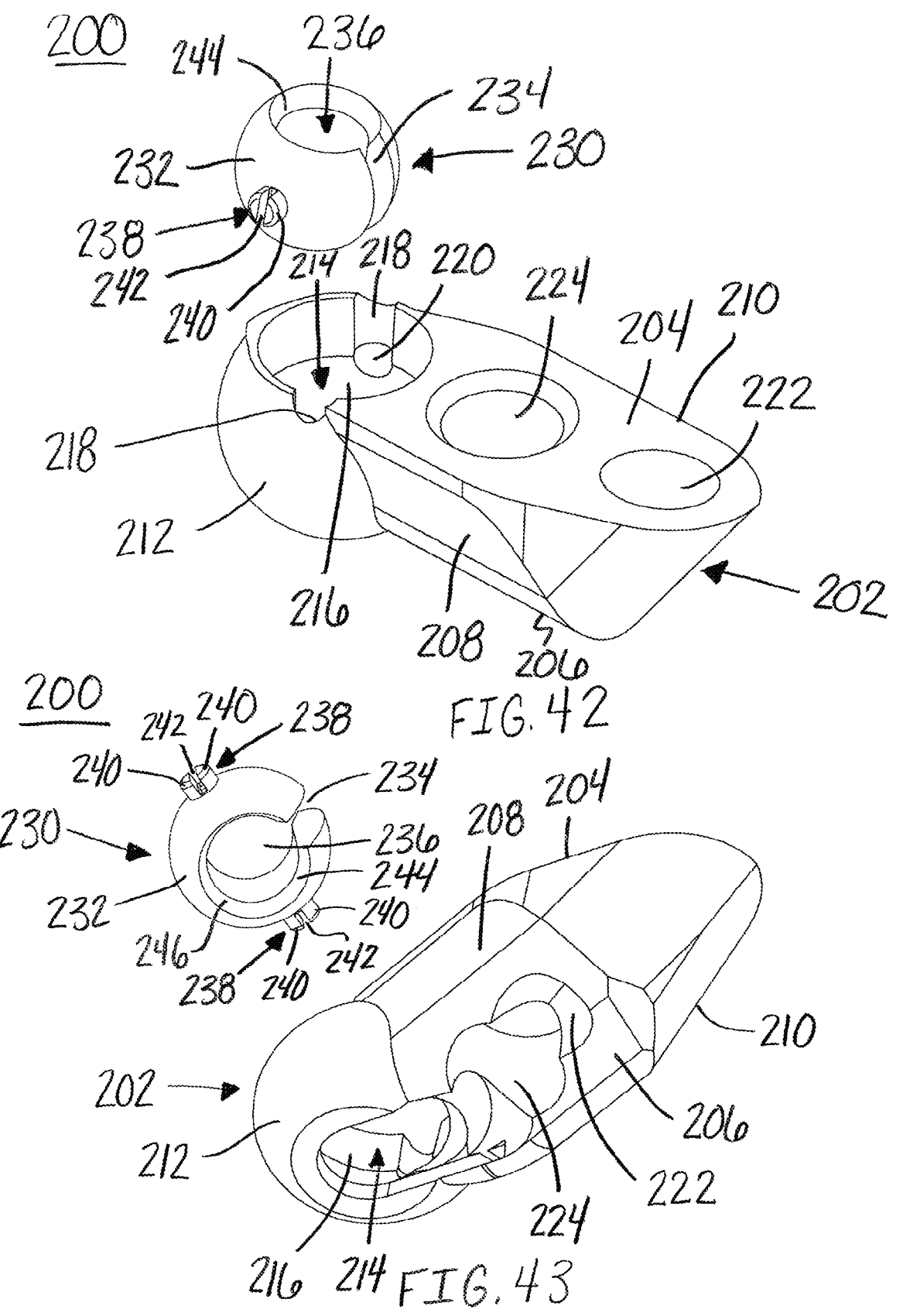
FIG. 42 is an exploded, top perspective view of the implant of FIG. 37, in accordance with an aspect of the present invention.
FIG. 43 is an exploded, bottom perspective view of the implant of FIG. 37, in accordance with an aspect of the present invention.
Figures 46, 47:
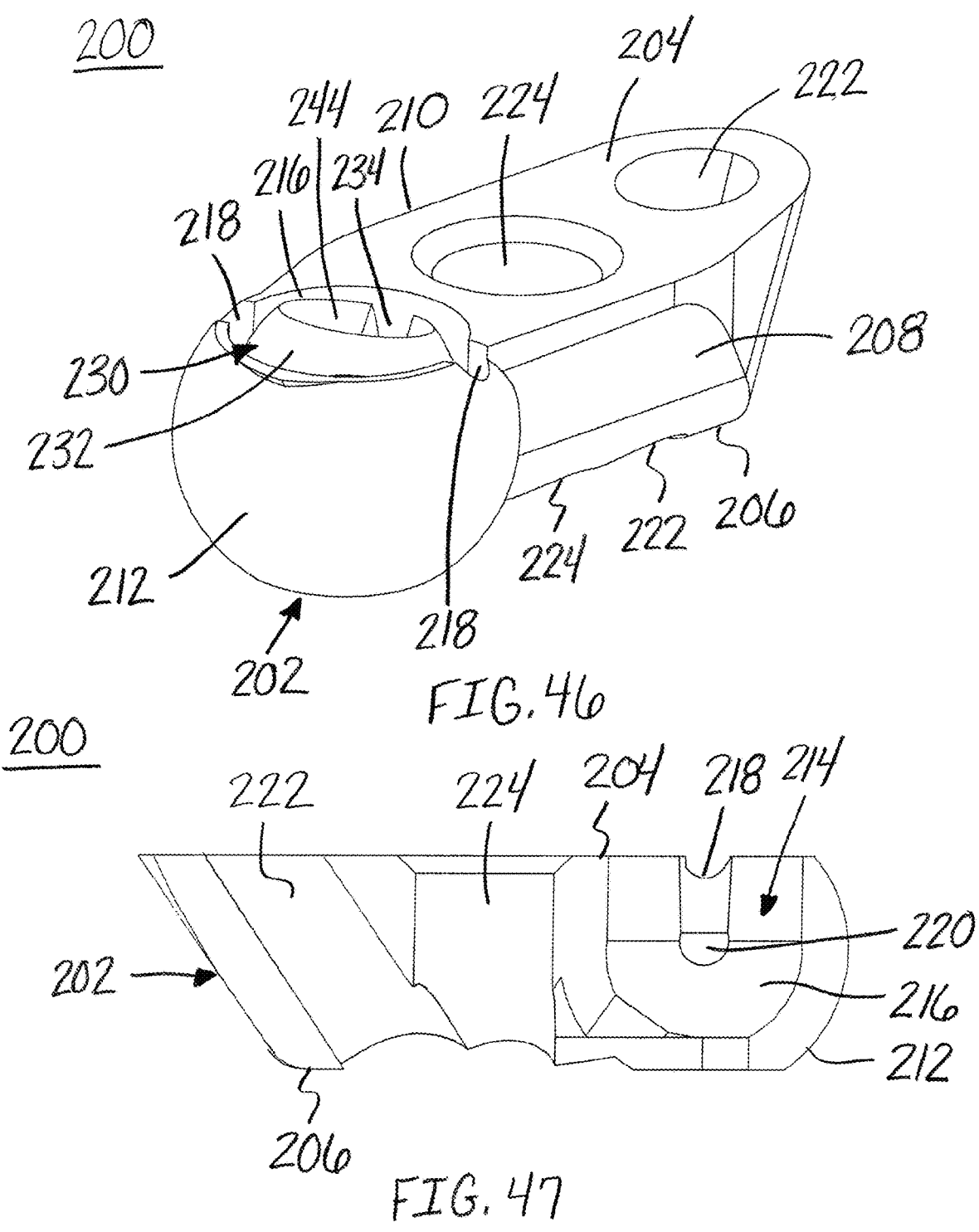
FIG. 46 is an assembled, end perspective view of the implant of FIG. 37, in accordance with an aspect of the present invention.
FIG. 47 is a cross section of the body of FIG. 37 taken along line 47-47 in FIG. 38, in accordance with an aspect of the present invention.

Referring now to FIGS. 37-47, another implant or connector device 200 is shown. The implant 200 may be, for example, a uniaxial implant. The implant 200 may include a body 202 and a movable member, bushing, spherical bushing, rotating member or rotating fastener hole 230, as shown in FIGS. 42-46. The body 202 and bushing 230 provide for angular fastener or screw adjustment along a single axis. The body 202 may include a top surface 204 opposite a bottom surface 206 and a first side 208 opposite a second side 210, as shown in FIGS. 38-46. The body 202 may also include a housing or spherical portion 212 at a first end. The housing 212 may include a through hole 214 extending through the body 202 from a top surface 204 to a bottom surface 206, as shown in FIGS. 38, 39, 42-45 and 47. The housing 212 may also include a spherical surface 216 inside the housing portion 212, as shown in FIGS. 38, 42-44, 46 and 47. The interior spherical surface 216 may be, for example, shaped to correspond to an exterior surface of the bushing 230. The spherical surface 216 of the housing 212 may include at least one slot 218 inset into the interior surface 216, as shown in FIGS. 38, 42 and 47. The at least one slot 218 may extend into the through hole 214 from a top surface 204 toward a bottom surface 206. The bottom of the at least one slot 218 may include a locking portion or bottom portion 220, as shown in FIGS. 42 and 47. The locking portion 220 may be, for example, sized and shaped or configured to secure the bushing 230 within the housing 212. The housing 212 may be, for example, positioned on the caudal end or the cephalad end. As shown, the housing 212 may include, for example, two slots 218 each with a locking portion 220 at the bottom of the slots 218. The diameter of the bottom portion 220 may be, for example, sized to receive a protrusion 238 on the bushing 230. In addition, the slot 218 may extend from the bottom portion 220 at, for example, a 2 degree taper to the top of the slot 218.

As shown in FIGS. 38, 39, and 42-47, the body 202 may also include, for example, a hole or opening 222 at a second end of the body 202. The hole 222 may be, for example, a fixed hole receiving a fixation member, bone screw, fastener, peg, pin, and/or spring. The hole 222 may be, for example, angled at a first trajectory as the hole 222 extends from a top surface 204 to a bottom surface 206. The hole 222 may be oriented, for example, for guiding a Jamshidi needle, k-wire, screw, or the like into the trajectory for placement in the pedicle or the facet/pedicle. The hole 222 may be, for example, positioned on the caudal end or the cephalad end. In one embodiment, for example, the facet/pedicle trajectory may enter the hole 222, such as a cephalad channel, and move in a caudal direction and the pedicle trajectory may enter in the caudal opening 214 and move in a cephalad direction. Although not shown, it is also contemplated that the second end of the body 202 could include another housing 212 for receiving a second bushing 230 to allow for angular screw or fastener adjustment at both ends of the body 202.

The body 202 may further include a locking opening or through hole 224, as shown in FIGS. 38, 39, and 42-47. The locking opening 224 may be positioned, for example, between the through hole 214 and the hole 222. The locking opening 224 may be sized and shaped or configured to allow an end of a handle member (not shown) to couple to the implant 160 for insertion into a patient. The locking opening 224 may also be, for example, sized and shaped or configured to receive a fastener, for example, a set screw 480, 490, as shown in FIGS. 73 and 74. The fasteners 480, 490 may be used to place pressure on the fasteners or screws (not shown) inserted through the through hole 214 and the hole 222 and into the facet/pedicle, to secure or lock the bone fusion device. The implant 200 may further include at least one lateral side indicator 226, as shown in FIGS. 38, 39, 41, 44 and 45. The at least one lateral side indicator 226 may be, for example, at least one protrusion, extension or a like feature extending away from a side of the body 202 or alternatively, a slot, recess, machine marking or a like feature inset into the side of the body 202, to designate the lateral side of the implant 200. In the depicted embodiment, the at least one lateral side indicator 226 is two alignment members 226. Further, the at least one lateral side indicator 226 may further designate whether the implant 200 is a left or right implant.

Figures 44, 45:
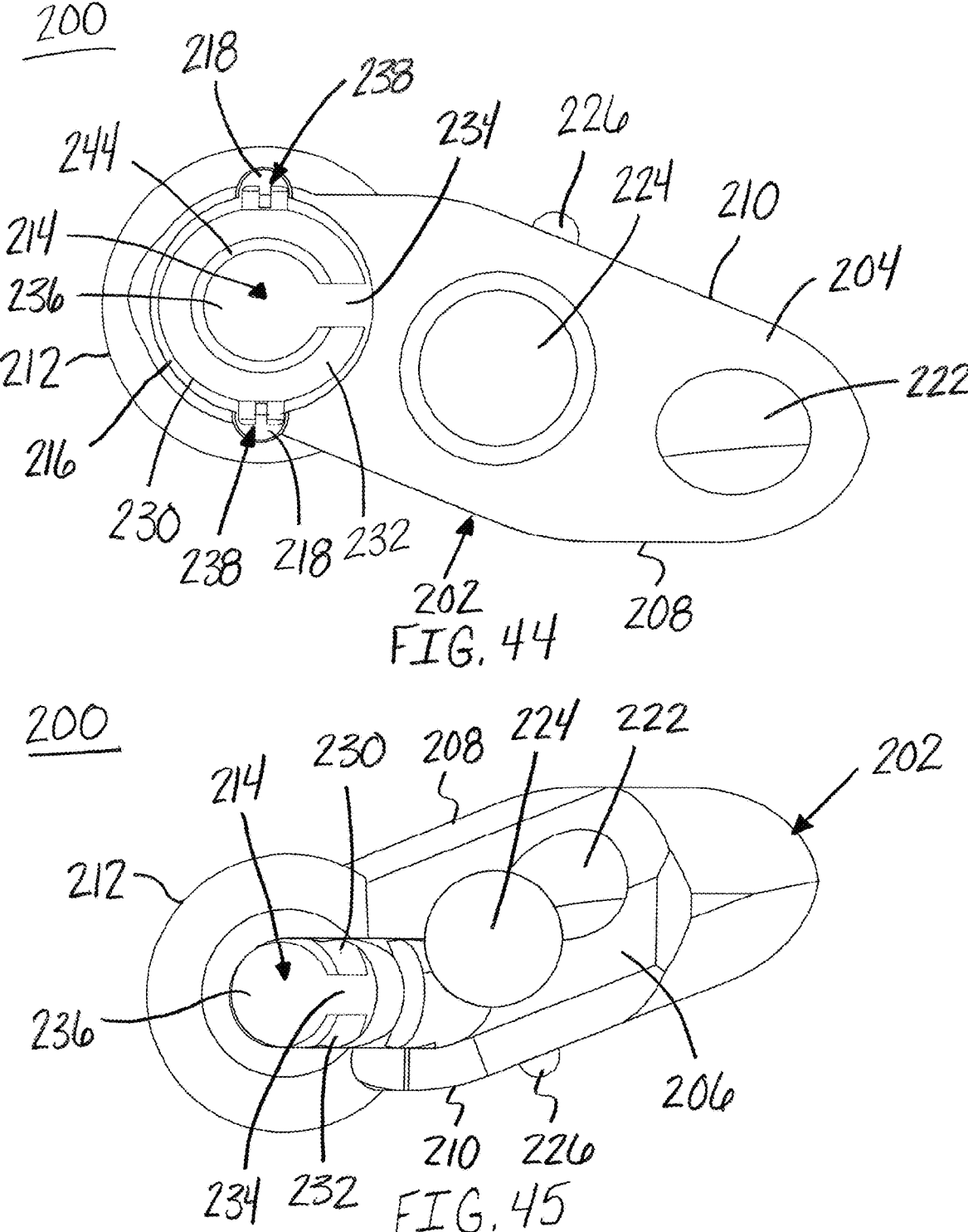
FIG. 44 is an assembled, top view of the implant of FIG. 37, in accordance with an aspect of the present invention.
FIG. 45 is an assembled, bottom view of the implant of FIG. 37, in accordance with an aspect of the present invention.

As shown in FIGS. 42-46, the bushing 230 may include a body 232 with a through hole 236 extending through the bushing 230. The bushing 230 may also include a slot 234 extending from an exterior surface into the through hole 236, as shown in FIGS. 42-46. The bushing 230 may further include at least one ear, locking portion, slotted axel, or protrusion 238, as shown in FIGS. 42-44. The at least one locking portion 238 may include tabs 240 with a slot 242 extending between the tabs 240. In the depicted embodiment, the bushing 230 includes two protrusions. The spherical bushing 230 may provide, for example, infinite angles of delivery of the bone fastener (not shown). The bushing 230 may also include an upper rim 244 positioned on a top surface of the bushing 230, as shown in FIG. 42, and a lower rim 246 positioned on a bottom surface, as shown in FIG. 43. The rims 244, 246 may be tapered at each opening of the through hole 236.

The implant 200 may be assembled by inserting the bushing 230 into the housing 212 of the body 202. The bushing 230 may have, for example, a diameter that may correspond to the spherical interior surface or bore 216 in one end of the implant 200. The bore 216 may have, for example, a spherical shape. The implant 200 may be, for example, factory assembled. During factory assembly, the bushing 230 may be compressed via the slot 234 in the bushing 230 and inserted into the bore 216 of the body 202. The bushing 230 will then expand in the bore 216, securely locking the bushing 230 within the body 202. The bushing 230 may provide a 360 degree range of motion to address changes in patient anatomy. The tapers 244, 246 on the opening 214 of the bushing 230 match the tapers of the fastener or bone screw (not shown). Once the fastener (not shown) is implanted in a bone and the taper under the head of the fastener makes contact with the taper 244, 246 of the bushing, the taper of the fastener (not shown) will expand the bushing 230 and lock the entire construct. The fastener may be, for example, a fixation member, bone screw, peg, pin, and/or spring. The taper under the head of the screw will correspond to or match the taper of the bushing 230.

The housing 212 of the implant 200 may allow for an angular adjustment of one of the screw fixation elements, bone screws, or fasteners (not shown). For example, a first fastener or screw (not shown) may be inserted through the hole 222 and into a patient's vertebrae. Then, a second fastener or screw (not shown) may be inserted through the through hole 214 and the direction of the fastener may be altered by the bushing 230 to accommodate the specific patient anatomy. In addition, the instrumentation, for example, the insertion guide 110 and locking block 140 may be configured or sized and shaped to allow for the angular adjustment positioning of the second fastener or fixation screw (not shown).

The implant 200 may be a part of a bone fusion device which may also include, for example, two cannulated fasteners, fixation screws or bone screws (not shown), and a central locking screw 480, 490, as shown in FIGS. 73-74. The two cannulated bone screws and central locking screw 480, 490 are configured or sized and shaped to provide a non-co-planar screw trajectory while allow for or achieving fusion. The implant 200 may be sized and shaped or configured to assist with guiding the two fasteners or screws into a patient's vertebrae. For example, the implant 200 may be used to guide the fixation screws (not shown) into divergent aspects of the vertebrae and to lock the two divergent fasteners or screws into place. Specifically, the implant 200 may be used to guide a first fastener or screw into a patient's pedicle and a second fastener or screw into the patient's facet/pedicle of a vertebrae.

Figures 48, 49:
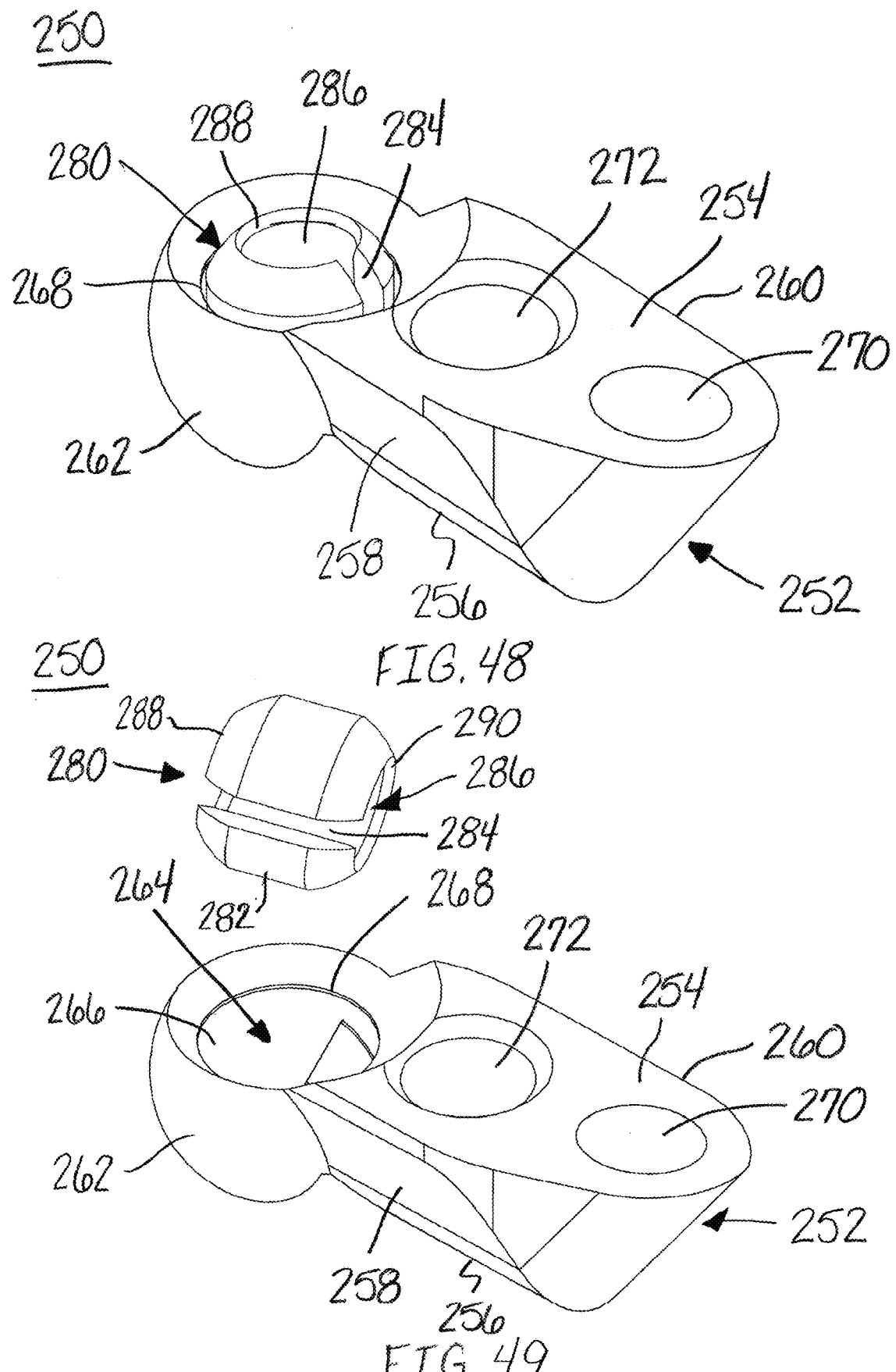
FIG. 48 is a top perspective view of another implant, in accordance with an aspect of the present invention.
FIG. 49 is an exploded, top perspective view of the implant of FIG. 48, in accordance with an aspect of the present invention.
Figures 50, 51:
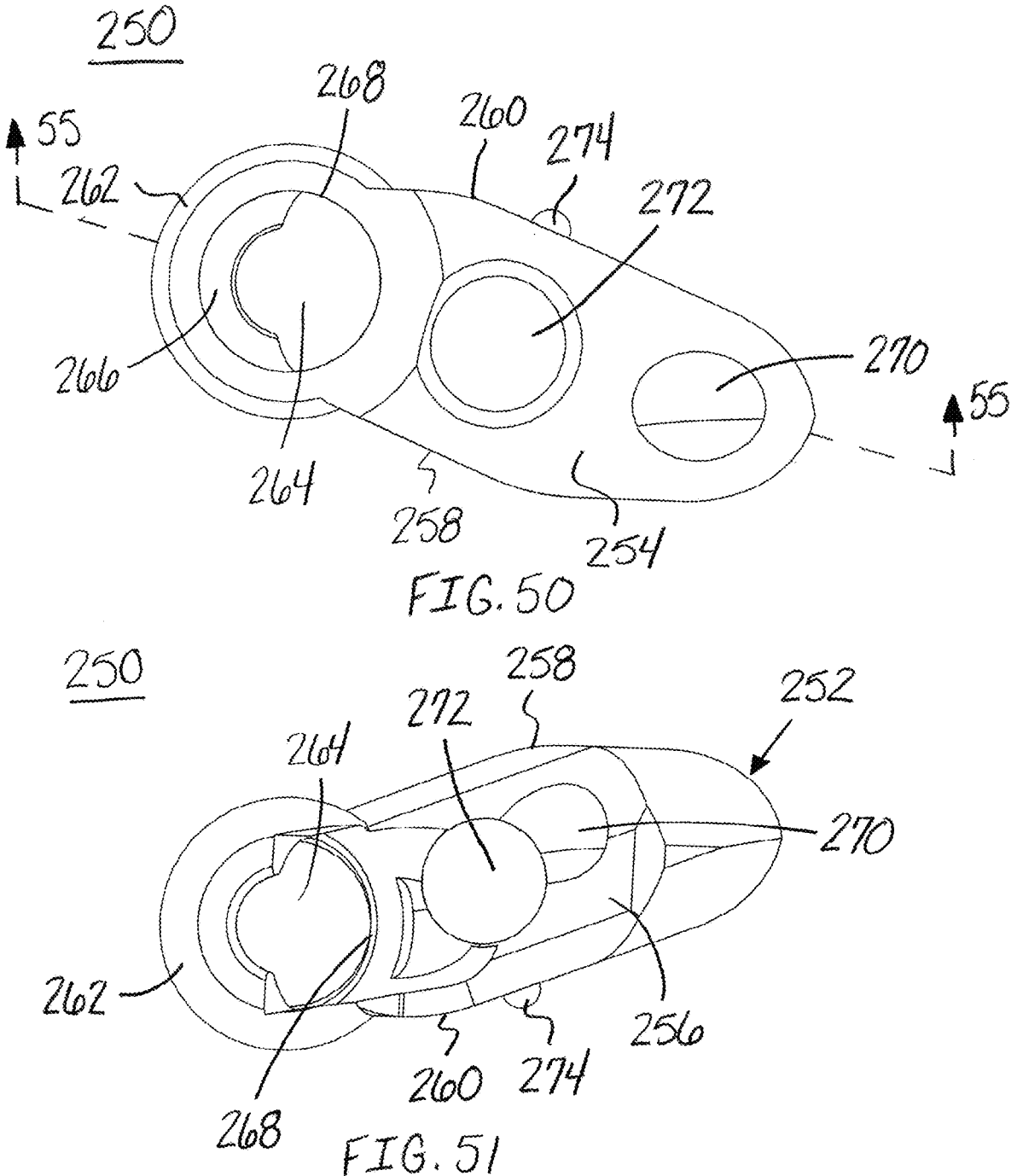
FIG. 50 is a top view of a body of the implant of FIG. 48, in accordance with an aspect of the present invention.
FIG. 51 is a bottom view of the body of FIG. 50, in accordance with an aspect of the present invention.
Figures 54, 55:
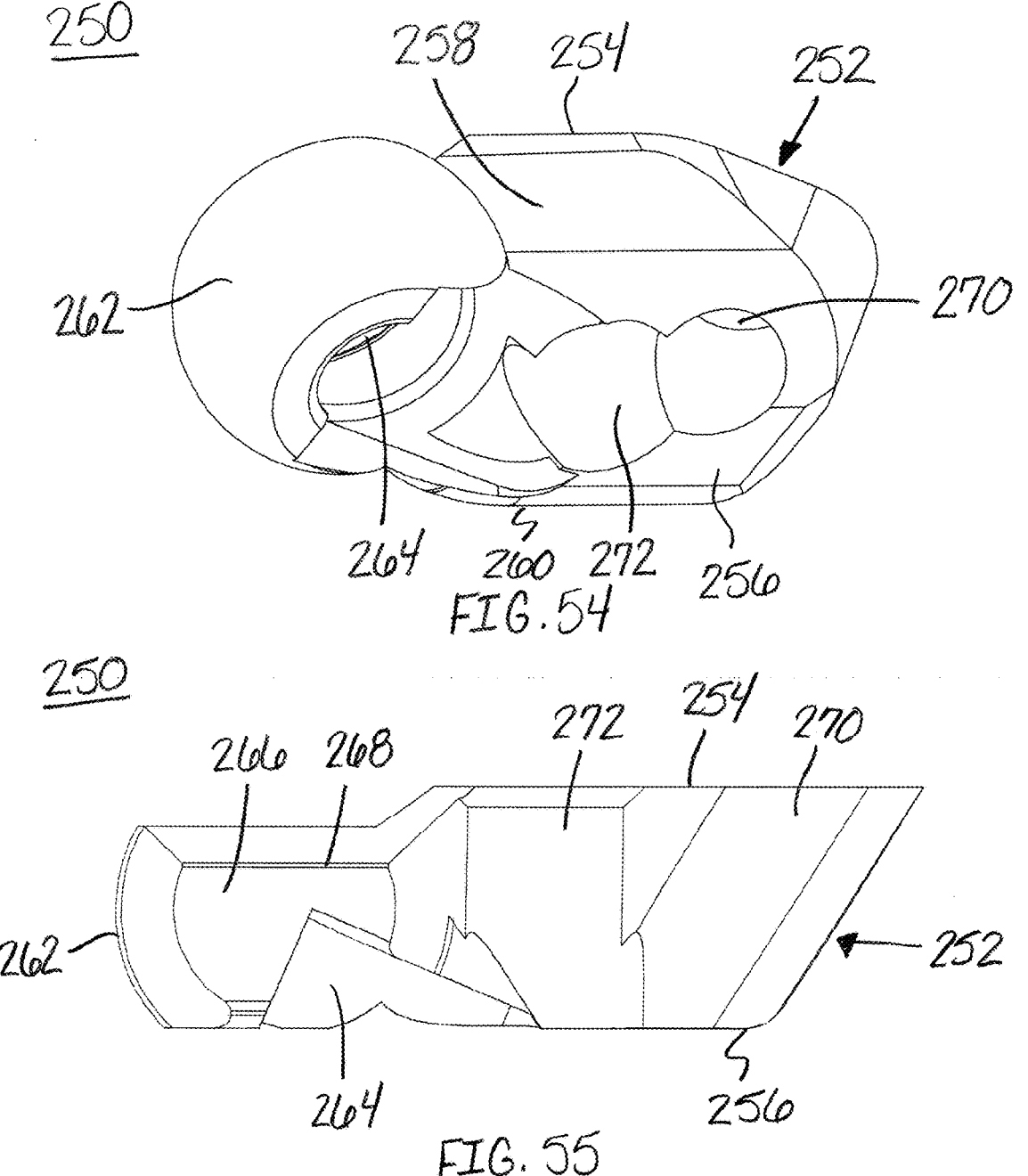
FIG. 54 is a bottom perspective view of the body of FIG. 50, in accordance with an aspect of the present invention.
FIG. 55 is a cross section of the body taken along line 55-55 of FIG. 50, in accordance with an aspect of the present invention.

Referring now to FIGS. 48-55, another implant, connector device or polyaxial implant 250 is shown. The implant 250 may be, for example, a polyaxial implant. The implant 250 may include a body 252 and a bushing, spherical bushing, rotating member or rotating fastener hole 280, as shown in FIGS. 48 and 49. The body 252 and bushing 280 provide for angular fastener or screw adjustment along multiple axes. The body 252 may include a top surface 254 opposite a bottom surface 256 and a first side 258 opposite a second side 260, as shown in at least FIGS. 48 and 49. The body 252 may also include a housing or spherical portion 262 at a first end. The housing 262 may include a through hole 264 extending through the body 252 from the top surface 254 to the bottom surface 256, as shown in FIGS. 49-51, 54 and 55. The housing 262 may also include an interior surface or spherical surface 266 inside the housing portion 262, as shown in FIGS. 49, 50 and 55. The interior surface 266 may be, for example, shaped to correspond to an exterior surface of the bushing 280. The interior surface 266 of the housing 262 may include a rim 268 surrounding the interior surface 266 near the top surface 254. The housing 262 may also include a tapered portion from the rim 268 to the top surface 254. The housing 262 may be, for example, positioned on the caudal end or the cephalad end.

As shown in FIGS. 48-51, 54 and 55, the body 252 may also include, for example, a hole 270 at a second end of the body 252. The hole 270 may be, for example, a fixed hole for receiving a fixation member, bone screw, fastener, peg, pin, and/or spring. The hole 270 may be, for example, angled at a first trajectory as the hole 270 extends from the top surface 254 to a bottom surface 256. The hole 270 may be oriented, for example, for guiding a Jamshidi needle, k-wire, screw, or the like into the trajectory for placement in the pedicle or the facet/pedicle. The hole 270 may be, for example, positioned on the caudal end or the cephalad end. In one embodiment, for example, the facet/pedicle trajectory may enter the hole 270, such as a cephalad channel, and move in a caudal direction and the pedicle trajectory may enter in the caudal opening 264 and move in a cephalad direction. Although not shown, it is also contemplated that the second end of the body 252 could include another housing 262 for receiving a second bushing 280 to allow for angular screw or fastener adjustment at both ends of the body 252.

Figures 52, 53:
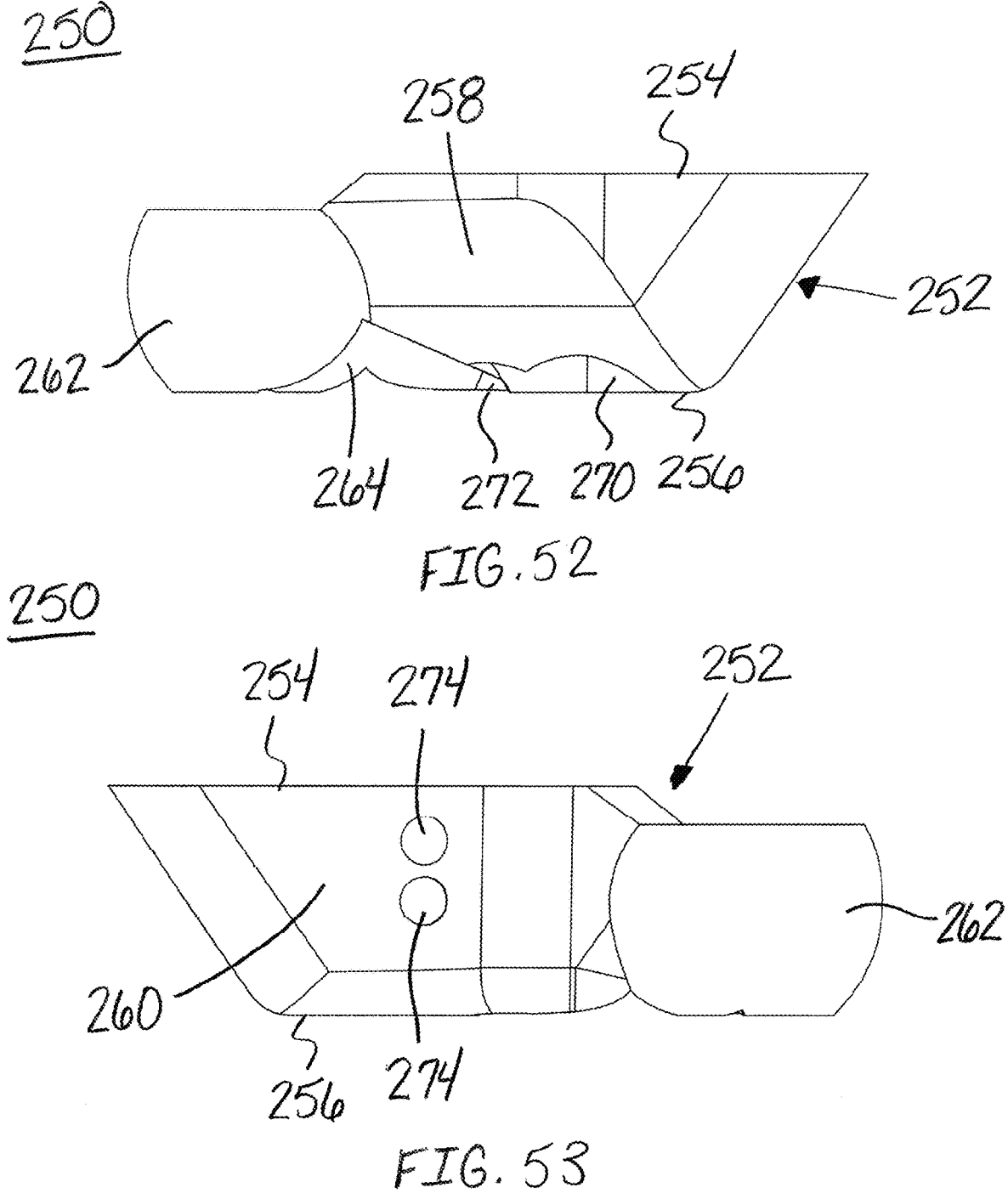
FIG. 52 is a first side view of the body of FIG. 50, in accordance with an aspect of the present invention.
FIG. 53 is a second side view of the body of FIG. 50, in accordance with an aspect of the present invention.

The body 252 may further include a locking opening or through hole 272, as shown in FIGS. 48-51, 54 and 55. The locking opening 272 may be positioned, for example, between the through hole 264 and the hole 270. The locking opening 272 may be sized and shaped or configured to allow an end of a handle member (not shown) to couple to the implant 250 for insertion into a patient. The locking opening 272 may also be, for example, sized and shaped or configured to receive a fastener, for example, a set screw 480, 490, as shown in FIGS. 73 and 74. The fasteners 480, 490 may be used to place pressure on the fasteners or screws (not shown) inserted through the through hole 264 and the hole 270 and into the facet/pedicle and pedicle, to secure or lock the bone fusion device. The implant 250 may further include at least one lateral side indicator 274, as shown in FIGS. 50, 51 and 53. The at least one lateral side indicator 274 may be, for example, at least one protrusion, extension or a like feature extending away from a side of the body 252 or alternatively, a slot, recess, machine marking or a like feature inset into the side of the body 252, to designate the lateral side of the implant 250. In the depicted embodiment, the at least one lateral side indicator 274 is two alignment members 274. Further, the at least one lateral side indicator 274 may further designate whether the implant 250 is a left or right implant.

As shown in FIGS. 48-49, the bushing 280 may include a body 282 with a through hole 286 extending through the bushing 280. The bushing 280 may also include a slot 284 extending from an exterior surface into the through hole 286, as shown in FIG. 49. The bushing 280 may further include an upper rim 288. The upper rim 288 may include, for example, a taper from the largest diameter of the exterior surface to a first end of the bushing 280. The bushing 280 may also include a lower rim 290. The lower rim 290 may include, for example, a taper from the largest diameter of the exterior surface to a second end of the bushing 280. The spherical bushing 280 may provide, for example, infinite angles of delivery of the fastener or bone screw (not shown).

The implant 250 may be assembled by inserting the bushing 280 into the housing 262 of the body 252. The body 282 may have, for example, a diameter that is smaller than the rim 268 for insertion of the movable member 280 within the body 252. The implant 250 may be, for example, factory assembled. During factory assembly, the bushing 280 may be positioned to align the through hole 286 to be parallel with the top surface 254 of the implant 250 and the bushing 280 is then inserted into the bore 264 of the body 252. The bushing 280 may then be rotated and the rim 268 of the body 252 will securely lock rims 288, 290 of the bushing 280 within the body 252. The bushing 280 may provide 360 degrees range of articulation to address changes in patient anatomy. Once the fastener or screw (not shown) is implanted in a bone and the fastener contacts the bushing 280 to lock the entire construct.

The housing 262 of the implant 250 may allow for an angular adjustment of one of the screw fixation elements, bone screws, or fasteners (not shown). For example, a first fastener or screw (not shown) may be inserted through the hole 270 and into a patient's vertebrae. Then, a second fastener or screw (not shown) may be inserted through the through hole 286 and the direction of the fastener or screw may be altered by the bushing 280 to accommodate the specific patient anatomy. In addition, the instrumentation, for example, the insertion guide 110 and locking block 140 may be configured or sized and shaped to allow for the angular adjustment positioning of the second fixation screw (not shown).

The implant 250 may be a piece of a bone fusion device which may also include, for example, two cannulated fasteners, fixation screws or bone screws (not shown), and a central locking screw 480, 490, as shown in FIGS. 73-74. The two cannulated bone screws and central locking screw 480, 490 are configured or sized and shaped to provide a non-co-planar screw trajectory while allow for or achieving fusion. The implant 250 may be sized and shaped or configured to assist with guiding the two fasteners or screws into a patient's vertebrae. For example, the implant 250 may be used to guide the fixation screws (not shown) into divergent aspects of the vertebrae and to lock the two divergent fasteners or screws into place. Specifically, the implant 250 may be used to guide a first fastener or screw into a patient's pedicle and a second fastener or screw into the patient's facet/pedicle of a vertebrae.

Referring now to FIGS. 56-59, another insertion guide or cross bar guide tower 300 is shown. The insertion guide 300 may include a base member or top block 302 with a top surface 304 opposite a bottom surface 306. The base member 302 may also include a first slot 308 forming an opening at a first end, a second slot 310 forming an opening at a second end, and a through hole 312 positioned between the first slot 308 and the second slot 310. The first slot 308 may extend through the base member 302 from the top surface 304 to the bottom surface 306. The first slot 308 may have, for example, a first trajectory which may be angled in a first direction. The first slot 308 may also extend, for example, parallel to the angled first end of the base member 302. The second slot 310 may extend through the base member 302 from the top surface 304 to the bottom surface 306. The second slot 310 may have, for example, a second trajectory which may be angled in a second direction. The second direction of the second slot 310 may be opposite the first direction of the first slot 308. The first and second trajectories may be positioned to extend past each other to allow for insertion of fasteners or screws (not shown) in a crossed, X-shaped or V-shaped arrangement. The second slot 310 may also extend, for example, parallel to the angled second end of the base member 302. The slots 308, 310 may be, for example, angled approximately 65-85 degrees from a top surface 304 of the base member 302, however, additional angles are also contemplated to correspond to variations in patient anatomy. The slots or guide wire through holes 308, 310 may be used to aid in alignment of the insertion guide or construct 300. The slots or slot features 308, 310 allow for the insertion guide or tower 300 to be separated from the implant, for example, implant 160, 200, 250, by releasing the guide wire (not shown). Although guide tower 300 is shown with a first and second slot 308, 310, it is also contemplated that the guide tower 300 may include either the first slot 308 or the second slot 310 and a through hole (not shown).

Figure 56:
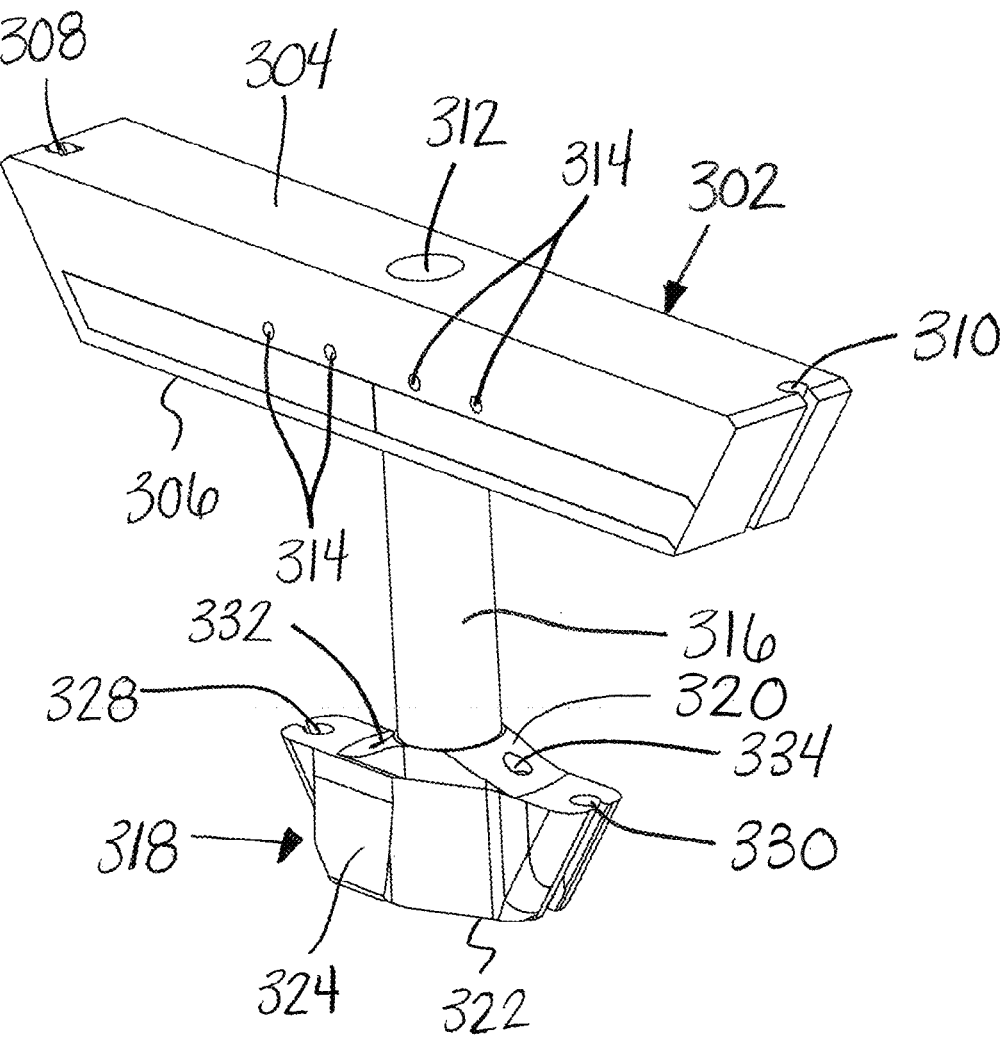
FIG. 56 is a top, perspective view of another insertion guide, in accordance with an aspect of the present invention.
Figure 57:
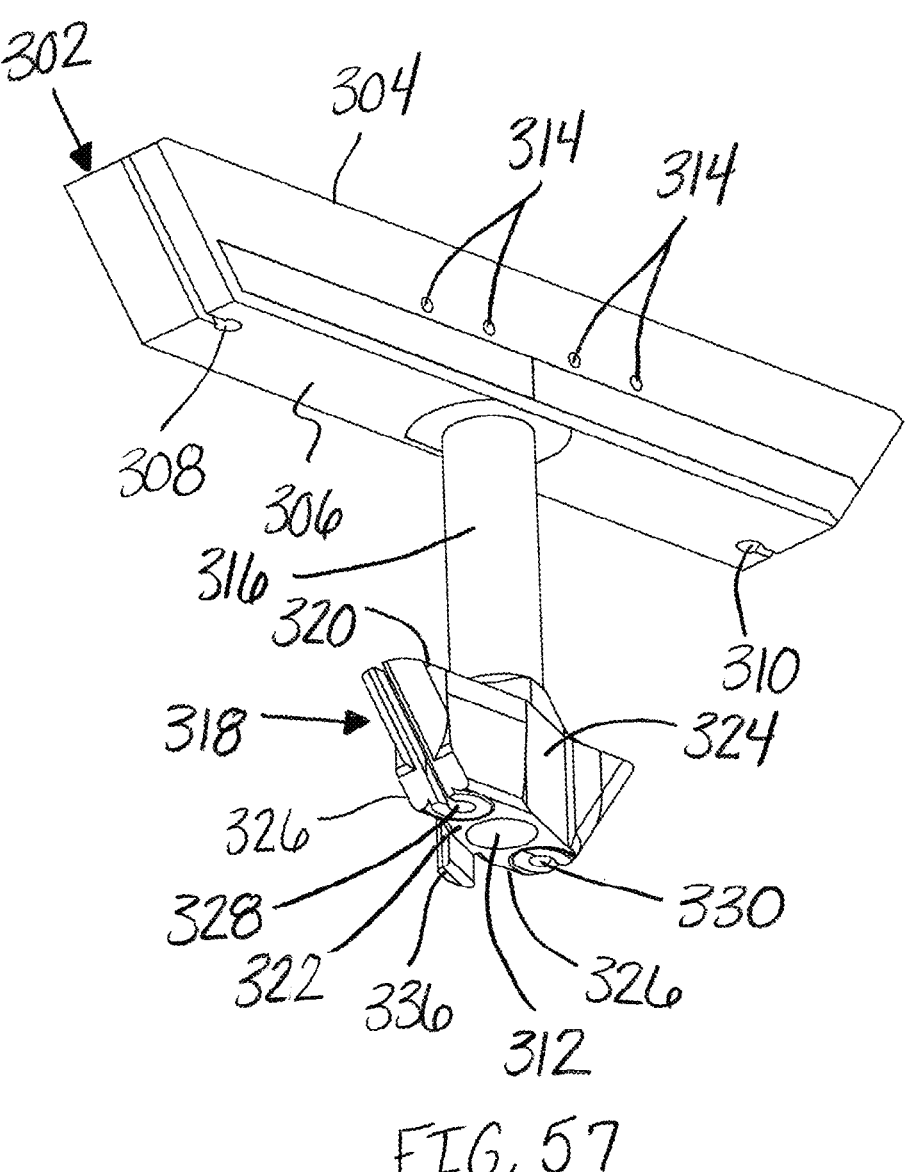
FIG. 57 is a bottom, perspective view of the insertion guide of FIG. 56, in accordance with an aspect of the present invention.

The through hole 312 may extend through the base member 302 from the top surface 304 to the bottom surface 306. The through hole 312 may extend, for example, through the base member 302 perpendicular to the top and bottom surfaces 304, 306. As shown in FIGS. 56 and 57, the base member 302 may also include at least one hole 314. The at least one hole 314 may extend between the sides of the base member 302, for example, relatively perpendicular to the through hole 312 and relatively parallel to the top and bottom surfaces 304, 306. The at least one hole 314 may provide, for example, a point of reference for the surgeon for the position or location of the slots 328, 330. For example, the lateral holes 314 may align with the top surface or entrance to the slots 328, 330 and the medial holes 314 may align with the bottom surface or exit of the slots 328, 330. Although the at least one hole 314 is shown as through holes, it is also contemplated that the holes 314 may be recesses, grooves, machine markings, and the like to provide a point of reference for the surgeon. Further, the openings 314 may receive a pin to provide additional visual reference point for determining the position of the locking block 318 and a coupled implant during insertion into a patient. The top surface 304 may be, for example, longer than the bottom surface 306. The base member 302 may have, for example, a generally trapezoidal cross-sectional shape forming, for example, a trapezoidal prism. Alternative polygonal shapes are also contemplated including, for example, at least, rectangles, parallelograms, and the like.

As shown in FIGS. 56-59, the connecting member 316 may have a first end and a second end. The first end of the connecting member 316 may be coupled to the base member 302 and aligned with the through hole 312. The second end of the connecting member 316 may be coupled to the implant coupling portion or locking block 318. The through hole 312 continues through the locking block 318 and is configured to receive a handle member (not shown). The handle member (not shown) may be similar to the handle member 510, as described in greater detail below with reference to FIGS. 75-81, including a gripping portion and an at least partially threaded rod for engaging an implant 160, 200, 250, 400, 450 for insertion into a patient.

Figure 59:
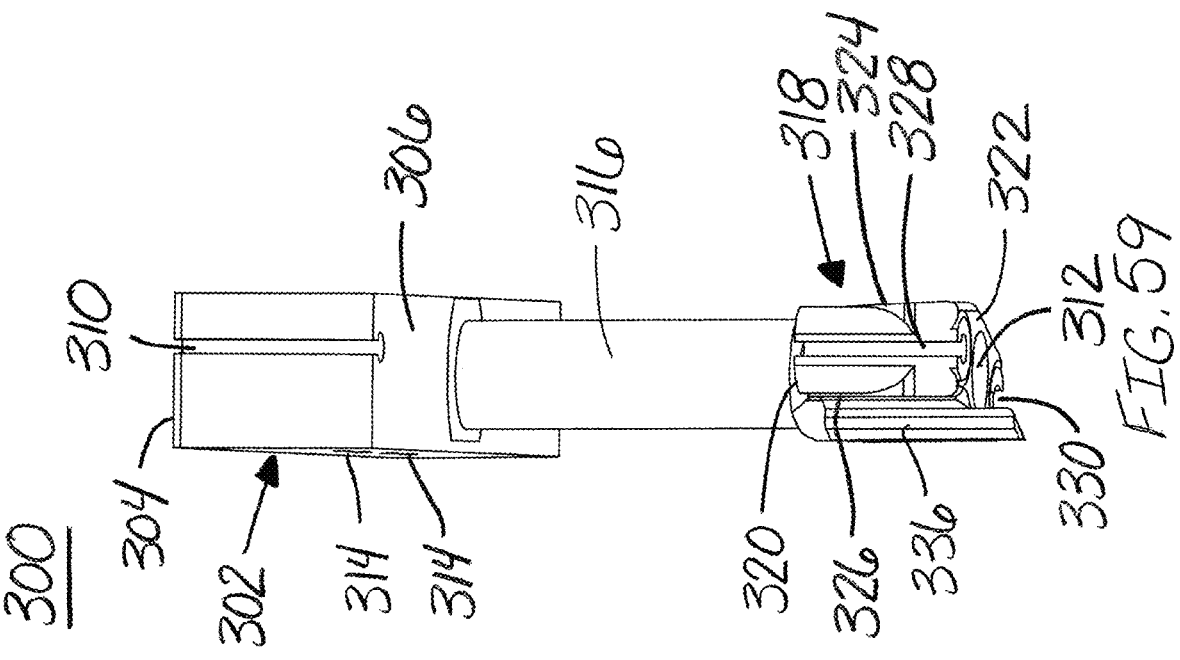
FIG. 59 is a second side, perspective view of the insertion guide of FIG. 56, in accordance with an aspect of the present invention.
Figure 58:
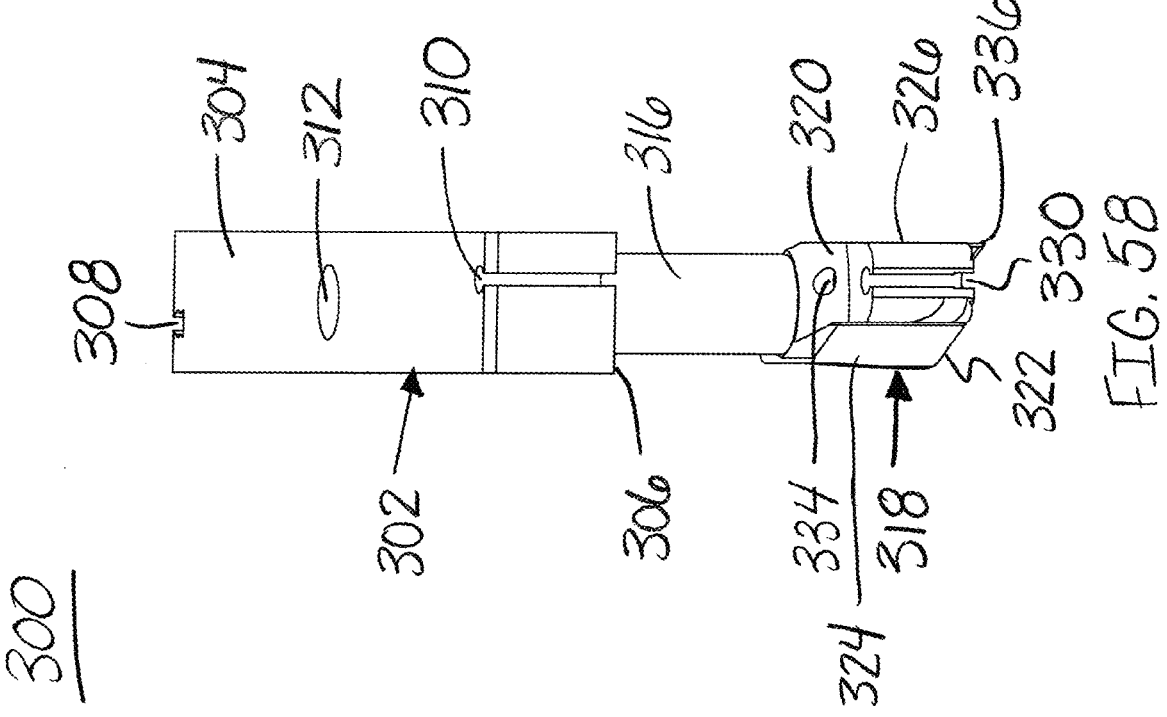
FIG. 58 is a first side, perspective view of the insertion guide of FIG. 56, in accordance with an aspect of the present invention.
Figures 60, 61:
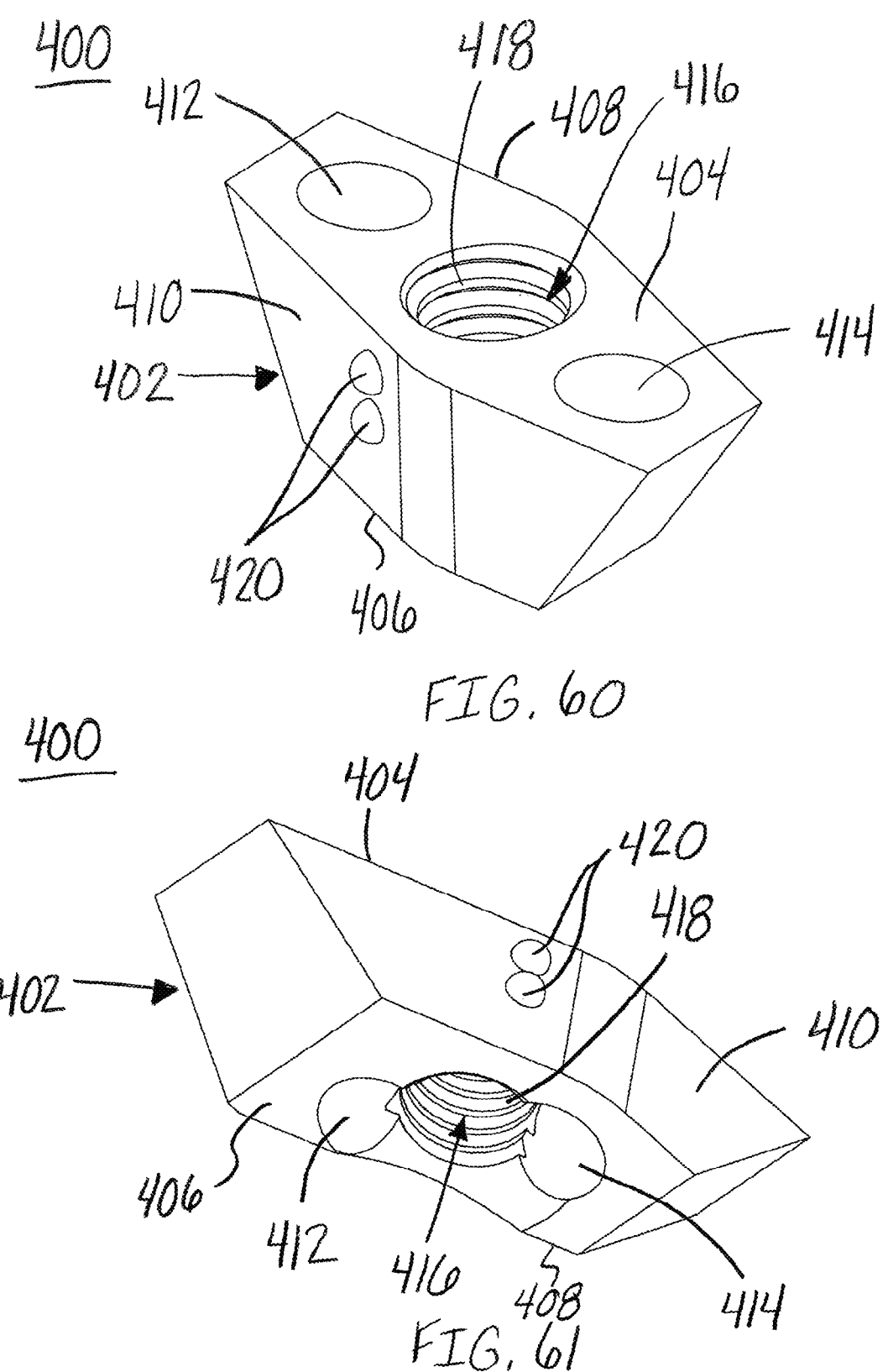
FIG. 60 is a top perspective view of another implant, in accordance with an aspect of the present invention.
FIG. 61 is a bottom perspective view of the implant of FIG. 60, in accordance with an aspect of the present invention.

As shown in FIGS. 56-59, the locking block 318 includes a top surface 320 opposite a bottom surface 322 and a first side 324 opposite a second side 326. The locking block 318 may also include a first slot 328 at a first end and a second slot 330 at a second end. The first and second slots 328, 330 may extend from the top surface 304 to the bottom surface 306. The first slot 328 may also extend from the exterior surface at the first end into the base member 302 to form a first opening and from the top surface 304 to the bottom surface 306, as shown in FIGS. 57 and 59. The second slot 330 may also extend from the exterior surface at the second end into the base member 302 to form a second opening and from the top surface 304 to the bottom surface 306, as shown in FIGS. 56 and 58. The first opening formed by the first slot 328 may also extend, for example, parallel to the angled first end of the locking block 318. The first slot 328 may have, for example, a first trajectory which may be angled in a first direction. The first trajectory of the locking block 318 may, for example, correspond to the first trajectory of the base member 302 to allow for a Jamshidi needle, k-wire, screw, or the like to be inserted and removed through the first 308 of the base member 302 and the first slot 328 of the locking block 318. The second slot 330 may also extend, for example, parallel to the angled second end of the locking block 318. The second slot 330 may have, for example, a second trajectory which may be angled in a second direction. The second trajectory of the locking block 318 may, for example, correspond to the second trajectory of the base member 302 to allow for a Jamshidi needle, k-wire, screw, or the like to be inserted and removed through the second slot 310 of the base member 302 and the second slot 330 of the locking block 318. The first and second trajectories may be selected, for example, to correspond to the desired placement in a patient's facet/pedicle and pedicle. The first and second slots 328, 330 may be, for example, angled approximately 65-85 degrees from a top surface 320 of the locking block 318, however, additional angles are also contemplated to correspond to variations in patient anatomy.

With continued reference to FIGS. 57 and 59, the locking block 318 may also include a center opening or through hole 312. The through hole 312 is configured to allow a handle member (not shown) to pass through the locking block 318 and engage an implant, for example, the implant 160, 200, 250. The through hole 312 may extend, for example, through the locking block 318 generally perpendicular to at least the bottom surface 322 of the locking block 318. The locking block 318 may further include an alignment member 336 positioned on a side of the locking block 318, as shown in FIGS. 57 and 59. The alignment member 336 may include at least one extension member 336 extending past the bottom surface 322 of the locking block 318. The at least one extension member may be, for example, multiple fork extensions 336. The at least one extension member of the alignment member 336 may be used to accurately locate the lateral aspect of an implant 160, 200, 250.

The cross bar guide tower or insertion guide 300 may couple to the connector device or implant 160, 200, 250 while placing the trajectory devices (not shown) or fixation device insertion instruments (not shown), for example, a Jamshidi needle or k-wires. The top block or base member 302 of the instrument 300 incorporates guide holes or slots 308, 310 to facilitate the insertion of a guide device (not shown) which may be, for example, a Jamshidi needle or similar device to aid in the delivery of a guide wire for subsequent surgical activities including passing the fixation screws through the locking block 300 to their final position.

Figures 62, 63:
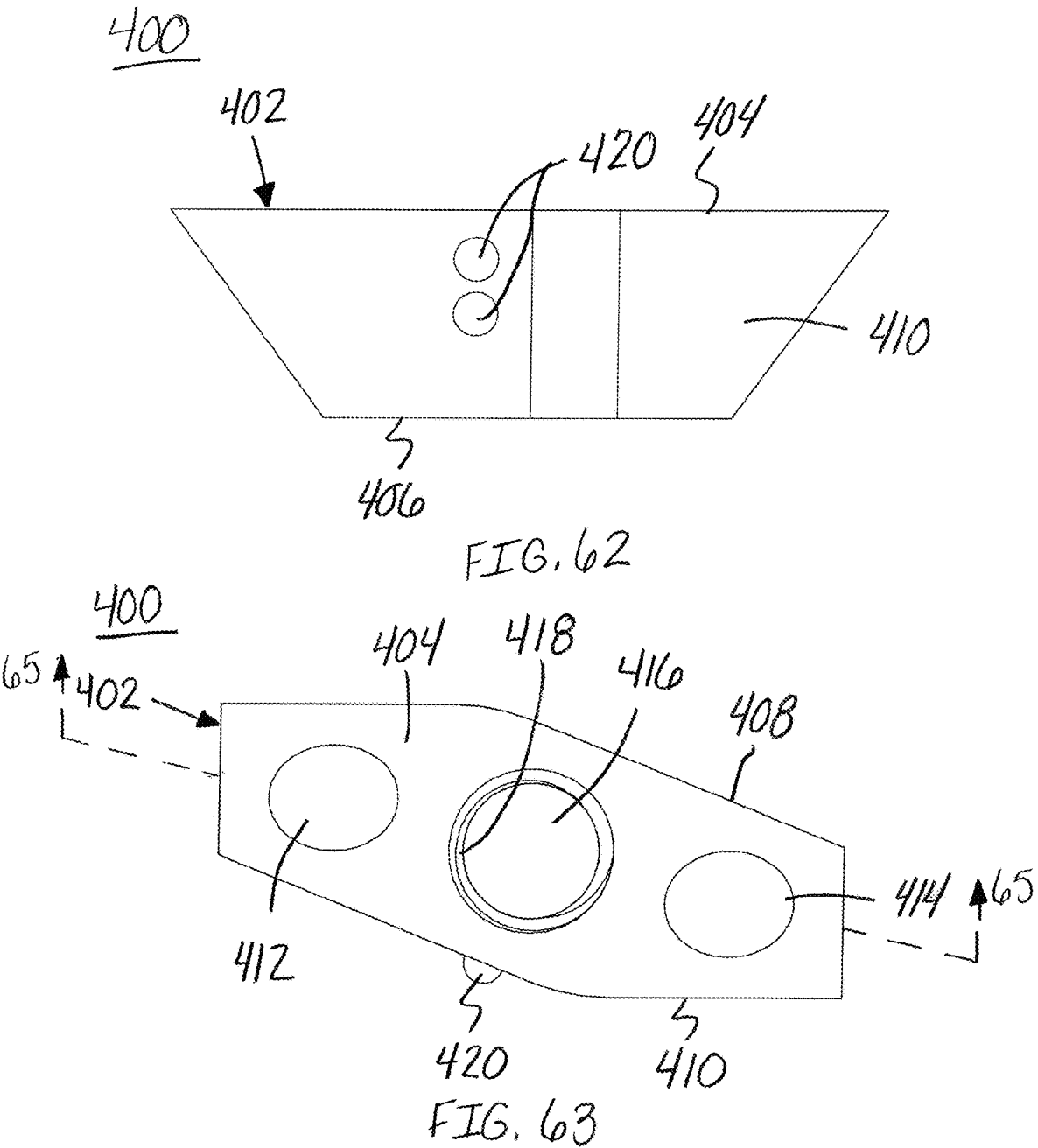
FIG. 62 is a side view of the implant of FIG. 60, in accordance with an aspect of the present invention.
FIG. 63 is a top view of the implant of FIG. 60, in accordance with an aspect of the present invention.
Figures 64, 65:
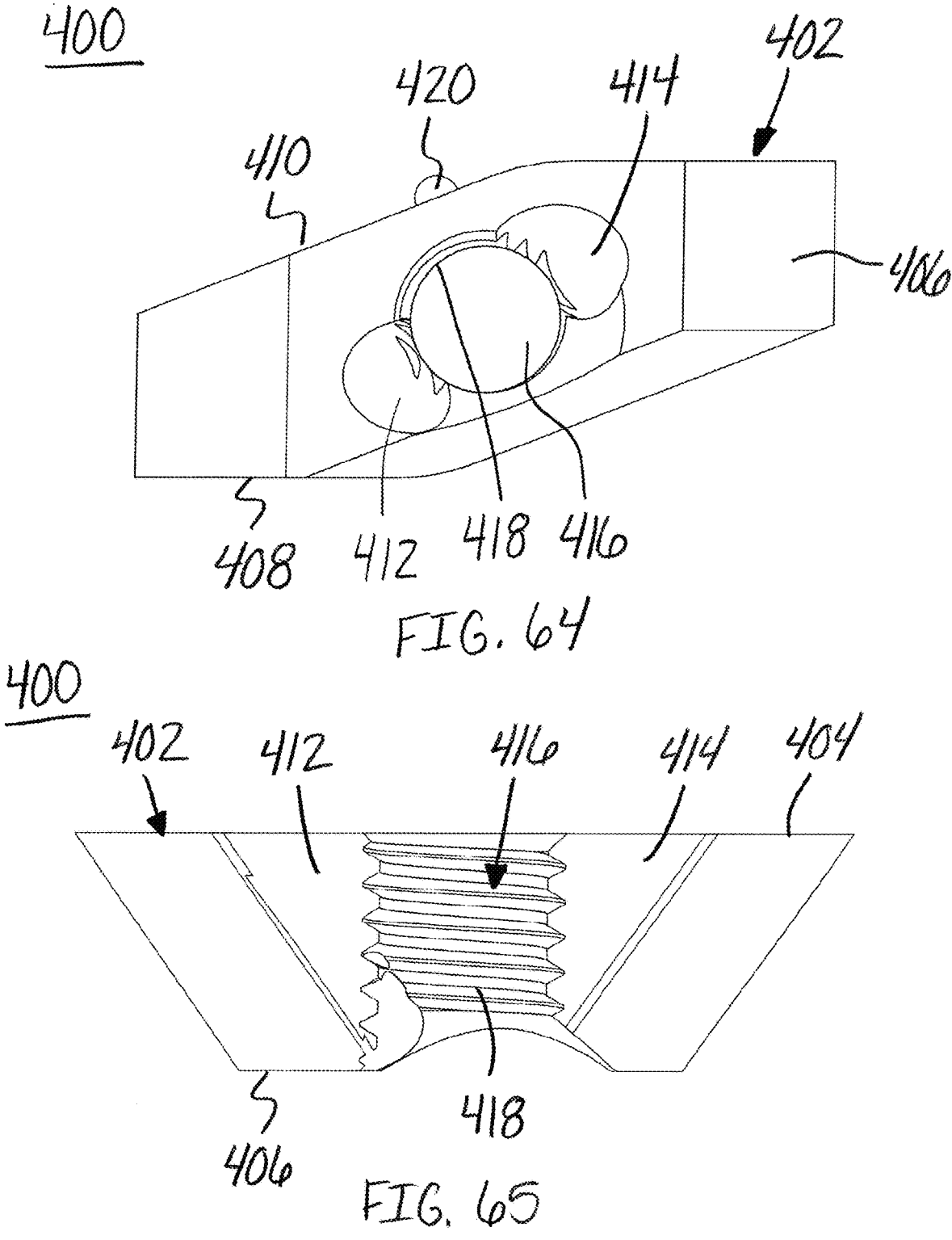
FIG. 64 is a bottom view of the implant of FIG. 60, in accordance with an aspect of the present invention.
FIG. 65 is a cross section of the implant of FIG. 60 taken along line 65-65 in FIG. 63, in accordance with an aspect of the present invention.
Figures 66, 67:
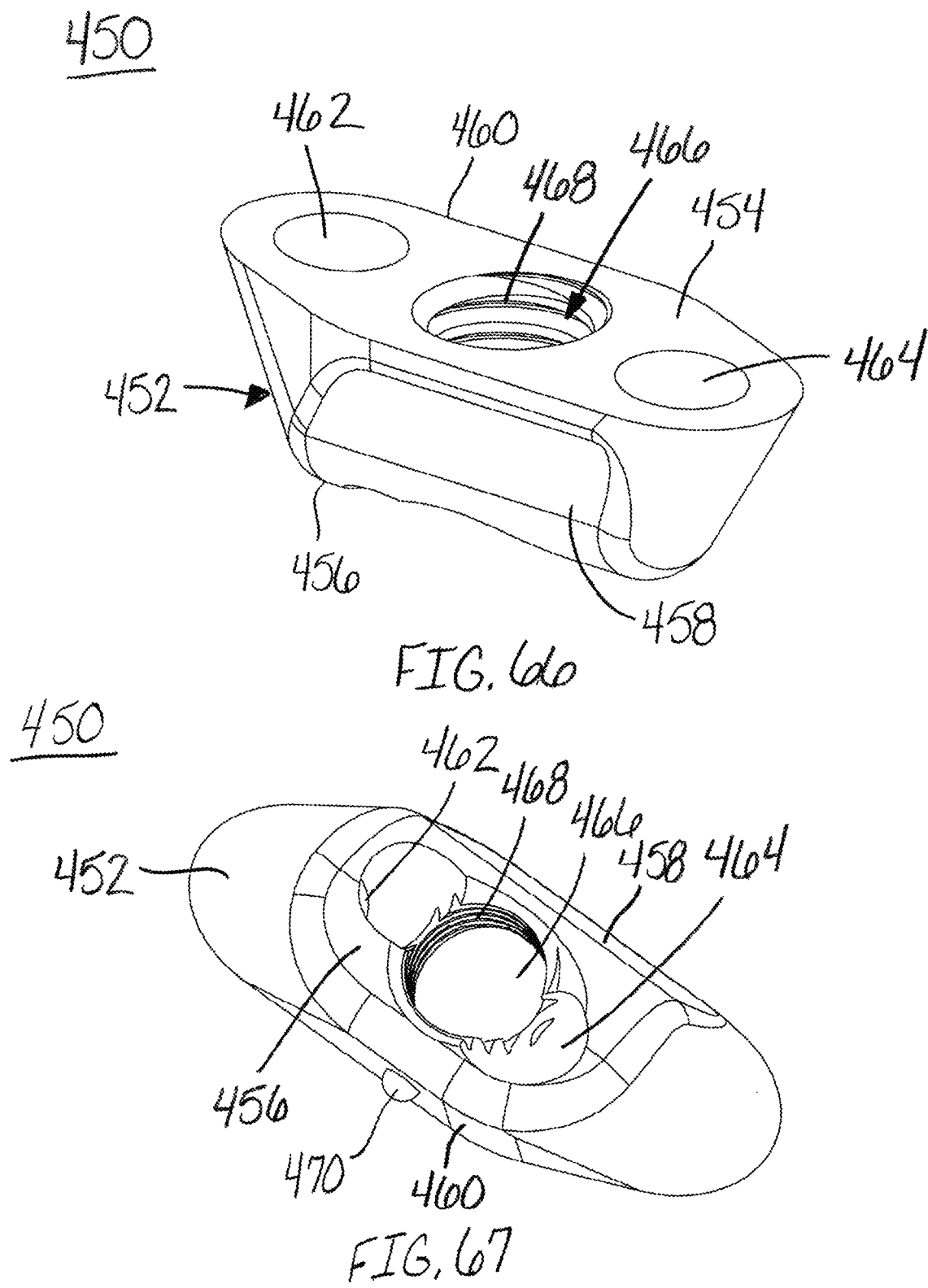
FIG. 66 is a top perspective view of another implant, in accordance with an aspect of the present invention.
FIG. 67 is a bottom perspective view of the implant of FIG. 67, in accordance with an aspect of the present invention.
Figures 68, 69:
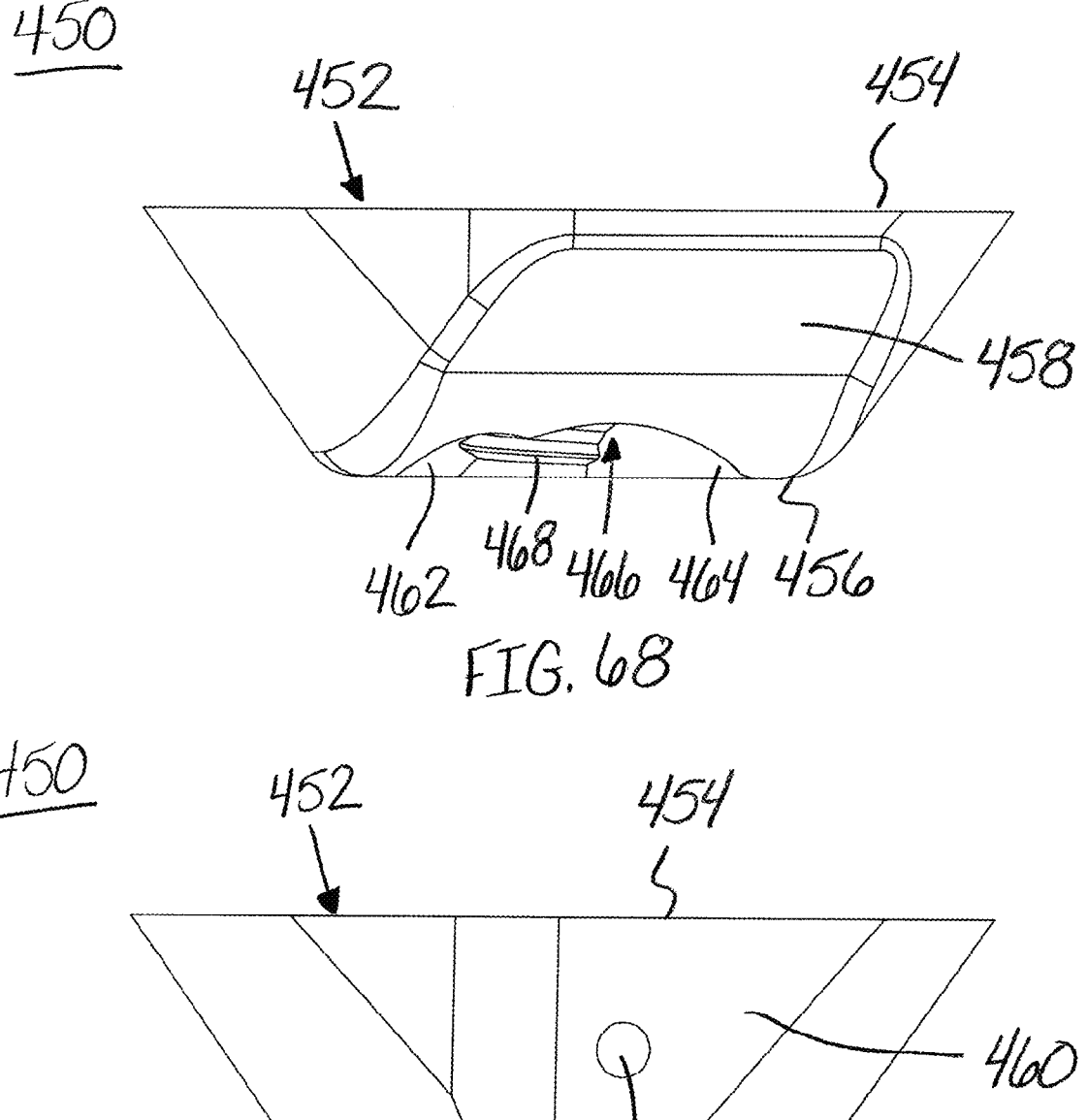
FIG. 68 is a first side view of the implant of FIG. 67, in accordance with an aspect of the present invention.
FIG. 69 is a second side view of the implant of FIG. 67, in accordance with an aspect of the present invention.
Figures 70, 71:
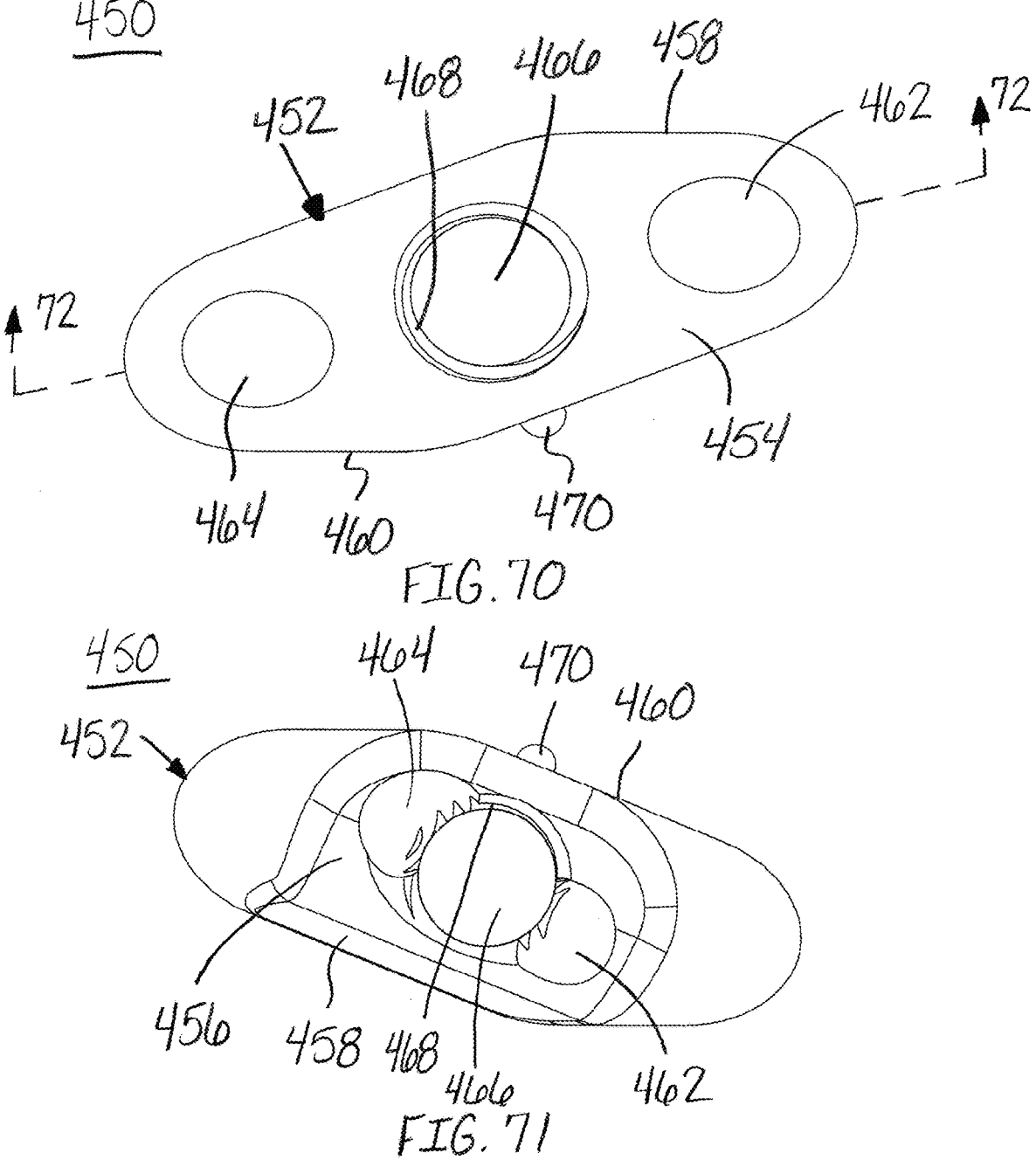
FIG. 70 is a top view of the implant of FIG. 67, in accordance with an aspect of the present invention.
FIG. 71 is a bottom view of the implant of FIG. 67, in accordance with an aspect of the present invention.

Referring now to FIGS. 60-65, another implant or connector device 400 is shown. The implant or connector device 400 includes a body 402 with a top surface 404 opposite a bottom surface 406 and a first side 408 opposite a second side 410. The implant 400 may be, for example, a three-dimensional misshapen parallelogram which may be angled on the ends, bottom surface and at least one side. The length of the top surface 404 may be, for example, longer than the length of the bottom surface 406 forming tapered ends, as shown in FIG. 62. The implant 400 may also be, for example, shaped to have a low profile to avoid bone and tissue impingement. In addition, the body 402 of the implant 400 may also have, for example, additional smoothing or rounded edges to accommodate a feature of a patient's anatomy while maintaining the necessary wall thickness in critical areas of the body 402 to maintain strength while reducing the incident of bone or tissue impingement.

As shown in FIGS. 60-65, the implant 400 may also contain a first channel or screw hole 412 and a second channel or screw hole 414. The first hole 412 may be, for example, angled at a first trajectory as the hole 412 extends from a top surface 404 to a bottom surface 406. The first hole 412 may be oriented, for example, on the caudal end for guiding a Jamshidi needle, k-wire, screw, or the like into the trajectory for placement in the pedicle. The second hole 414 may be, for example, angled at a second trajectory as the hole 414 extends from a top surface 404 to a bottom surface 406. The second hole 414 may be oriented, for example, on the cephalad end for guiding a Jamshidi needle, k-wire, screw, or the like into the desired facet/pedicle trajectory. In one embodiment, for example, the facet/pedicle trajectory enters in the cephalad channel 414 and moves in a caudal direction and the pedicle trajectory enters in the caudal channel 412 and moves in a cephalad direction. The first and second trajectories may be positioned to extend past each other to allow for insertion of fasteners or screws (not shown) in a crossed, X-shaped or V-shaped arrangement. The first and second holes 412, 414 may be, for example, angled approximately 65-85 degrees from a top surface 454 of the implant 400, however, additional angles are also contemplated to correspond to variations in patient anatomy.

The implant 400 may also contain a center channel or locking opening 416 positioned, for example, between the first screw hole 412 and the second screw hole 414, as shown in FIGS. 60, 61 and 63-65. The center channel 416 may be, for example, sized and shaped or configured to receive a fastener, for example, a set screw 480, 490, as shown in FIGS. 73 and 74. The fastener 480, 490 may be used to place pressure on the screws (not shown) inserted through the holes 412, 414 and into the facet and/or pedicle, thereby securing or locking the bone fusion device. The center channel 416 may include, for example, threads 418. In addition, the implant 400 may include at least one lateral side indicator 420, as shown in FIGS. 60-64. The at least one lateral side indicator 420 may be, for example, at least one protrusion, extension or a like feature extending away from a side of the body 402 or alternatively, a slot, recess, machine marking or a like feature inset into the side of the body 402, to designate the lateral side of the implant 400. Further, the at least one lateral side indicator 420 may further designate whether the implant 400 is a left or right implant.

Referring now to FIGS. 66-72, another implant or connector device 450 is shown. The implant or connector device 450 includes a body 452 with a top surface 454 opposite a bottom surface 456 and a first side 458 opposite a second side 460. The implant 450 may be, for example, a three-dimensional misshapen parallelogram which may be rounded on the ends, bottom surface and at least one side. The length of the top surface 454 may be, for example, longer than the length of the bottom surface 456 forming tapered ends. The implant 450 may have a radius on the outer diameter of the first or medial side 458 to accommodate the spinous process. In one embodiment, for example, the first side 458 of the implant 450 may have approximately a 15 degree angle transitioning into a 10 mm radius, although other angles and radius sizes are contemplated. The implant 450 may also be, for example, shaped to have a low profile to avoid bone and tissue impingement. In addition, the body 452 of the implant 450 may also have, for example, additional smoothing or rounded edges to accommodate a feature of a patient's anatomy while maintaining the necessary wall thickness in critical areas of the body 452 to maintain strength while reducing the incident of bone or tissue impingement.

As shown in FIGS. 66-72, the implant 450 may also contain a first channel or hole 462 and a second channel or hole 464. The first hole 462 may be, for example, angled at a first trajectory as the hole 462 extends from a top surface 454 to a bottom surface 456. The first hole 462 may be oriented, for example, on the caudal end for guiding a Jamshidi needle, k-wire, screw, or the like into the trajectory for placement in the pedicle. The second hole 464 may be, for example, angled at a second trajectory as the second hole 464 extends from a top surface 454 to a bottom surface 456. The second hole 464 may be oriented, for example, on the cephalad end for guiding a Jamshidi needle, k-wire, screw, or the like into the desired facet/pedicle trajectory. In one embodiment, for example, the facet/pedicle trajectory enters in the cephalad channel 464 and moves in a caudal direction and the pedicle trajectory enters in the caudal channel 462 and moves in a cephalad direction. The first and second trajectories may be positioned to extend past each other (non-intersecting) to allow for insertion of fasteners or screws (not shown) in a crossed, X-shaped or V-shaped arrangement.

The implant 450 may also contain a center channel or locking opening 466 positioned, for example, between the first hole 462 and the second hole 464, as shown in FIGS. 66, 67 and 70-72. The center channel 466 may be, for example, sized and shaped or configured to receive a fastener, for example, a set screw 480, 490, as shown in FIGS. 73 and 74. The fastener 480, 490 may be used to place pressure on the screws (not shown) inserted through the holes 462, 464 and into the facet/pedicle and pedicle, thereby securing or locking the bone fusion device. The center channel 466 may include, for example, threads 468. In addition, the implant 450 may include at least one lateral side indicator 470, as shown in FIGS. 67 and 69-71. The at least one lateral side indicator 470 may be, for example, at least one protrusion, extension or a like feature extending away from a side of the body 452 or alternatively, a slot, recess, machine marking or a like feature inset into the side of the body 452, to designate the lateral side of the implant 450. Further, the at least one lateral side indicator 470 may further designate whether the implant 450 is a left or right implant.

The implant 400, 450 may be a piece or part of a bone fusion device which may also include, for example, two cannulated fasteners, fixation screws or bone screws (not shown), and a central locking screw 480, 490, as shown in FIGS. 73-74. The two cannulated bone screws and central locking screw 480, 490 are configured or sized and shaped to provide a non-co-planar screw trajectory while allow for or achieving fusion. The implant 400, 450 may be sized and shaped or configured to assist with guiding the two fasteners or screws into a patient's vertebrae. For example, the implant 400, 450 may be used to guide the fixation screws (not shown) into divergent aspects of the vertebrae and to lock the two divergent fasteners or screws into place. Specifically, the implant 400, 450 may be used to guide a first fastener or screw into a patient's pedicle and a second fastener or screw into the patient's facet/pedicle of a vertebrae.

Referring now to FIG. 73, the first locking screw 480 is shown. The first locking screw 480 may include a threaded body 482. The first locking screw 480 may also include a drive opening 484 at a first end and an engagement protrusion 486 at a second end. The drive opening 484 may be, for example, hexagonal, square, Phillips or another multi-lobed configuration for coupling with an insertion instrument. The engagement protrusion 486 may have a pointed end 488 and a triangular cross section. The base of the protrusion 486 may have a larger diameter than the connector portion.

A second locking screw 490 is shown in FIG. 74. The second locking screw 490 may include a threaded body 492. The second locking screw 490 may also include a drive opening 494 at a first end and an engagement protrusion 496 at a second end. The drive opening 494 may be, for example, hexagonal, square, Phillips or another multi-lobed configuration for coupling with an insertion instrument. The engagement protrusion 496 may be tapered as the engagement protrusion 496 extends away from the threaded portion of the threaded body 492.

Referring now to FIGS. 75-81 and 84, a reduction tool 500 is shown. The reduction tool 500 may be used, for example, when a patient presents with spondylolisthesis or a displacement of a spinal vertebra in relation to an adjacent vertebra, to fix the spondylolisthesis prior to inserting stabilization devices, such as, fasteners, screws, connecting devices and the like. The reduction tool 500 may include a tower bolt or handle member 510, a base member or holder 520, coupling member 540, bone contacting member 550, and a ball lock, wing nut, or securement member 560. The base member 520 may be coupled to the tower bolt 510 by the securement member 560. In addition, the coupling member 540 may engage the base member 520 and may receive the bone contacting member 550. The bone contacting member 550 may engage a patient's bone during insertion of a connector device 160, 200, 250, 400, 450. Further, an end of the tower bolt 510 may be sized and shaped or configured to engage an implant 160, 200, 250, 400, 450. The handle member 510 may be used for directing the reduction tool 500 into the wound site. While the bone contacting member 550 may be used to apply pressure on the lamina once attached to the handle member 510 and inserted into the patient.

Figure 75:
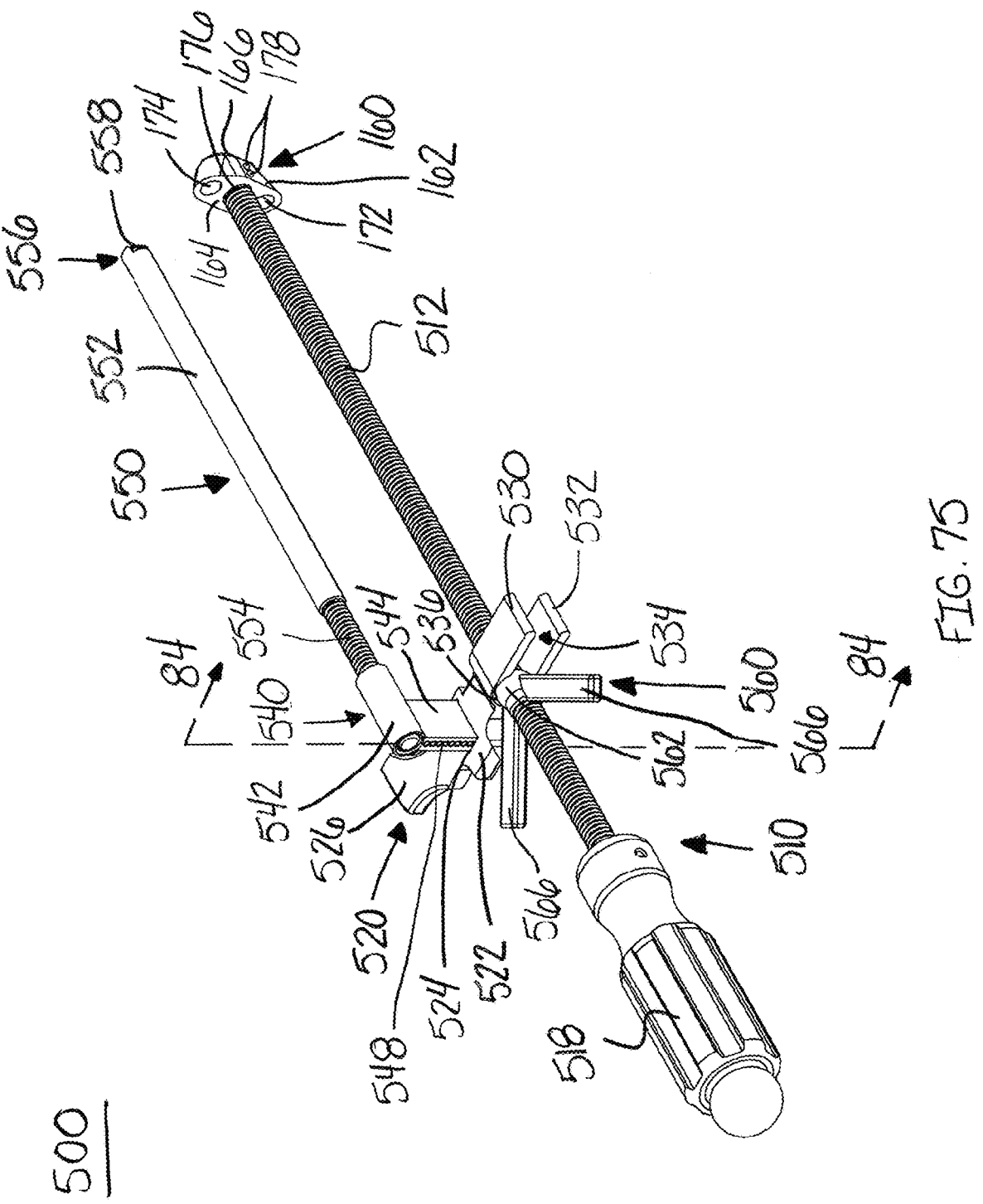
FIG. 75 is a first end, perspective view of a reduction tool, in accordance with an aspect of the present invention.
Figure 78:
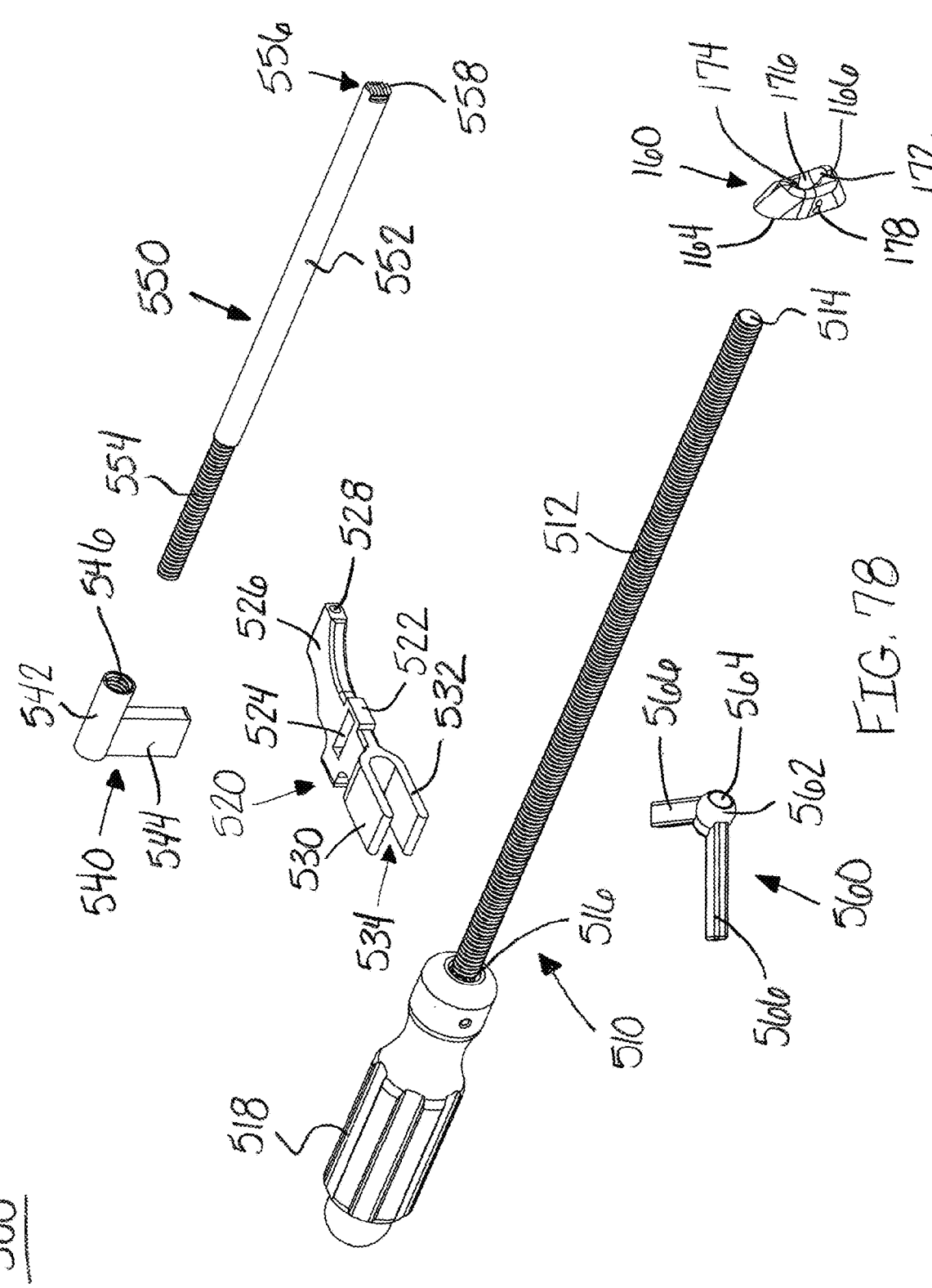
FIG. 78 is an exploded, second end perspective view of the reduction tool of FIG. 75, in accordance with an aspect of the present invention.
Figure 79:
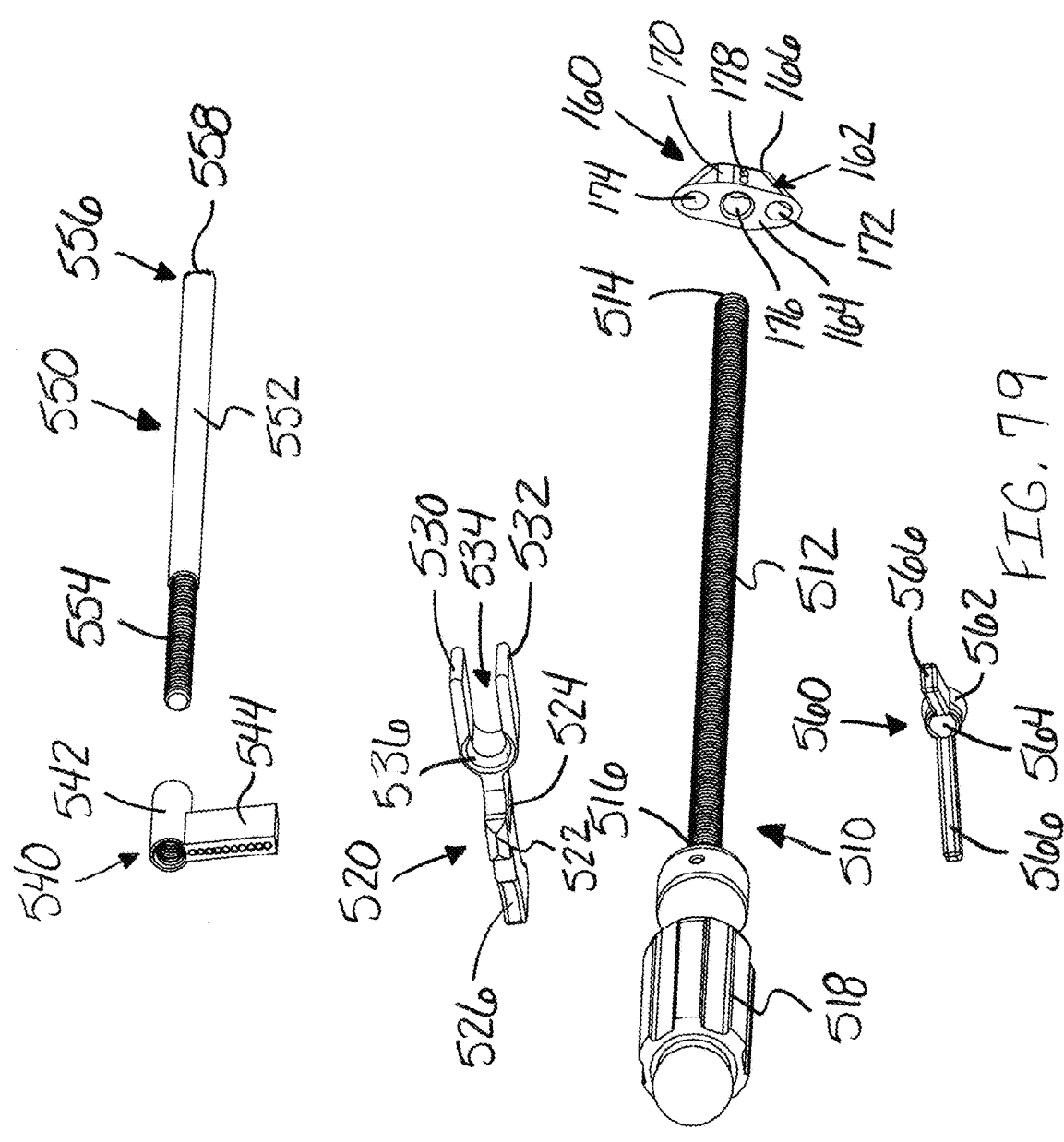
FIG. 79 is an exploded, first end perspective view of the reduction tool of FIG. 75, in accordance with an aspect of the present invention.
Figure 80:
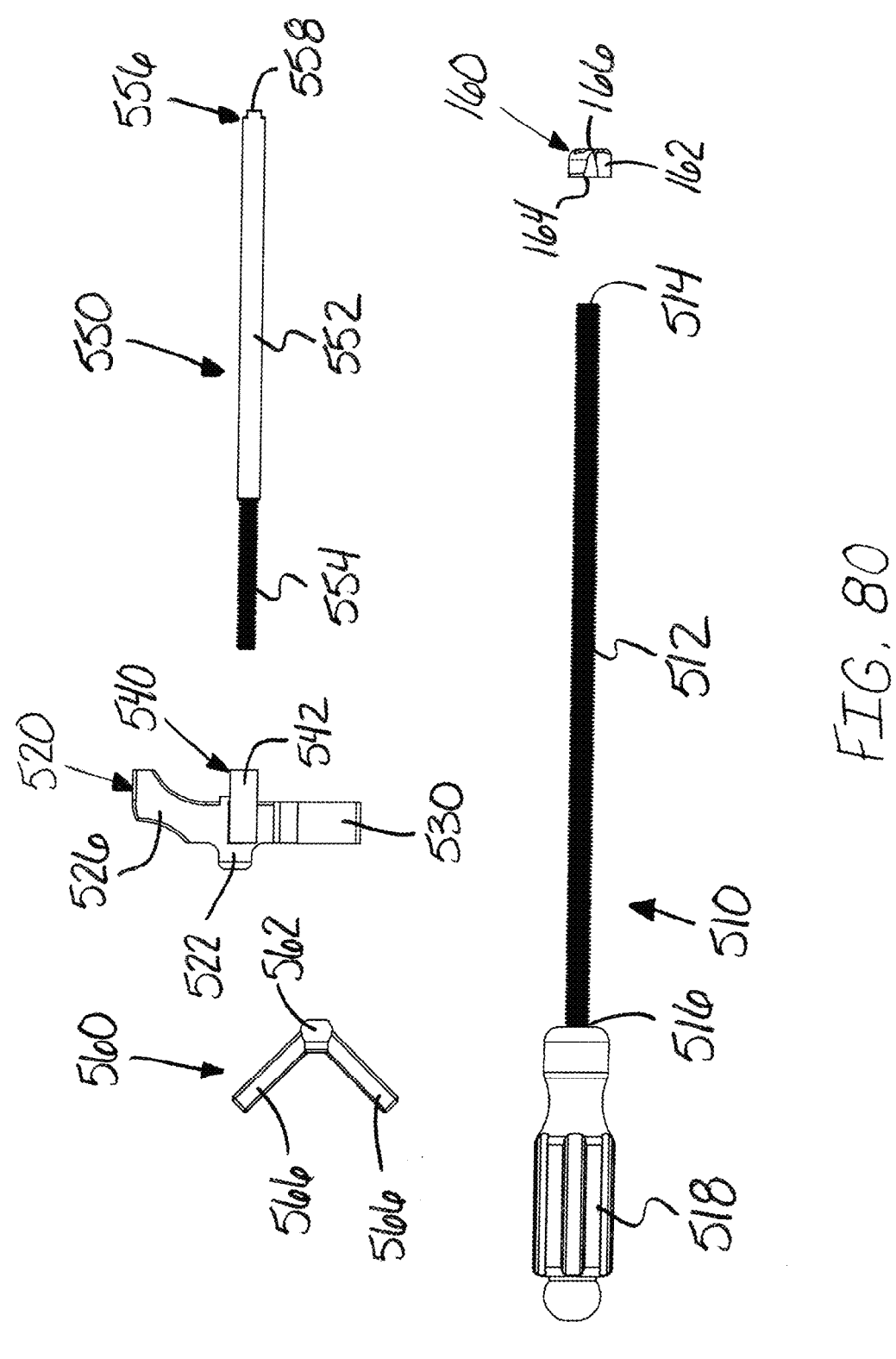
FIG. 80 is an exploded, first side view of the reduction tool of FIG. 75, in accordance with an aspect of the present invention.
Figure 81:
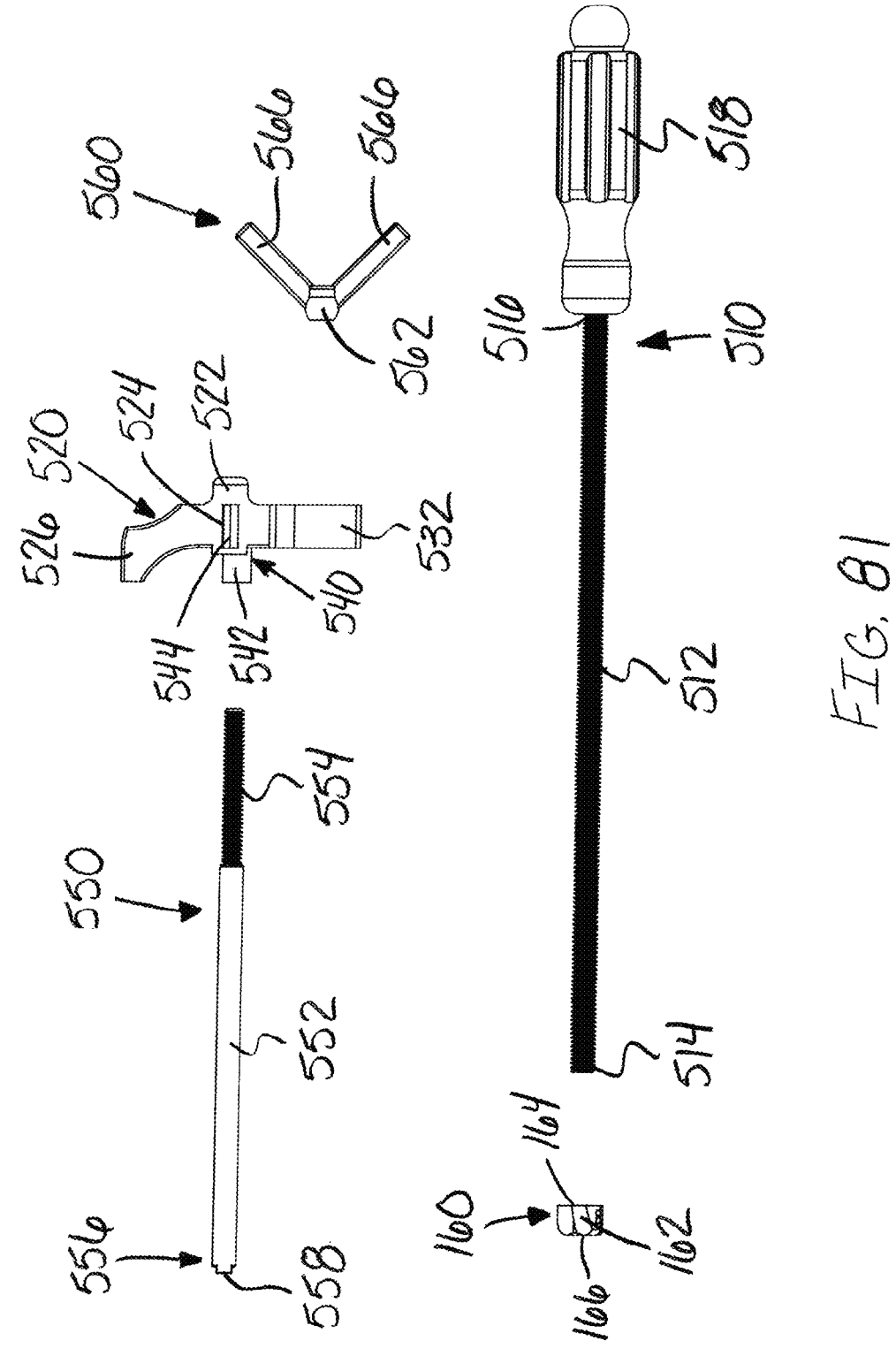
FIG. 81 is an exploded, second side view of the reduction tool of FIG. 75, in accordance with an aspect of the present invention.
Figure 84:
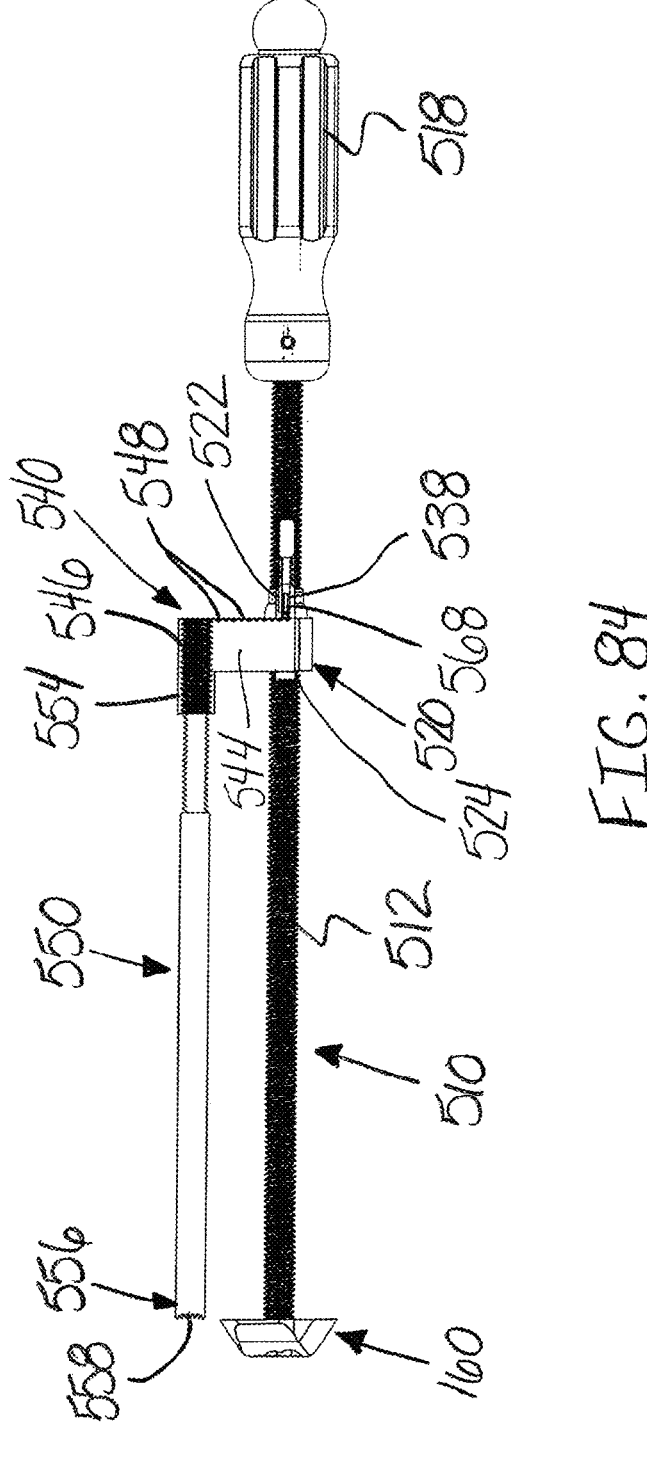
FIG. 84 is a cross sectional view of the reduction tool of FIG. 75 take along line 84-84 in FIG. 75, in accordance with an aspect of the present invention.
Figure 85:
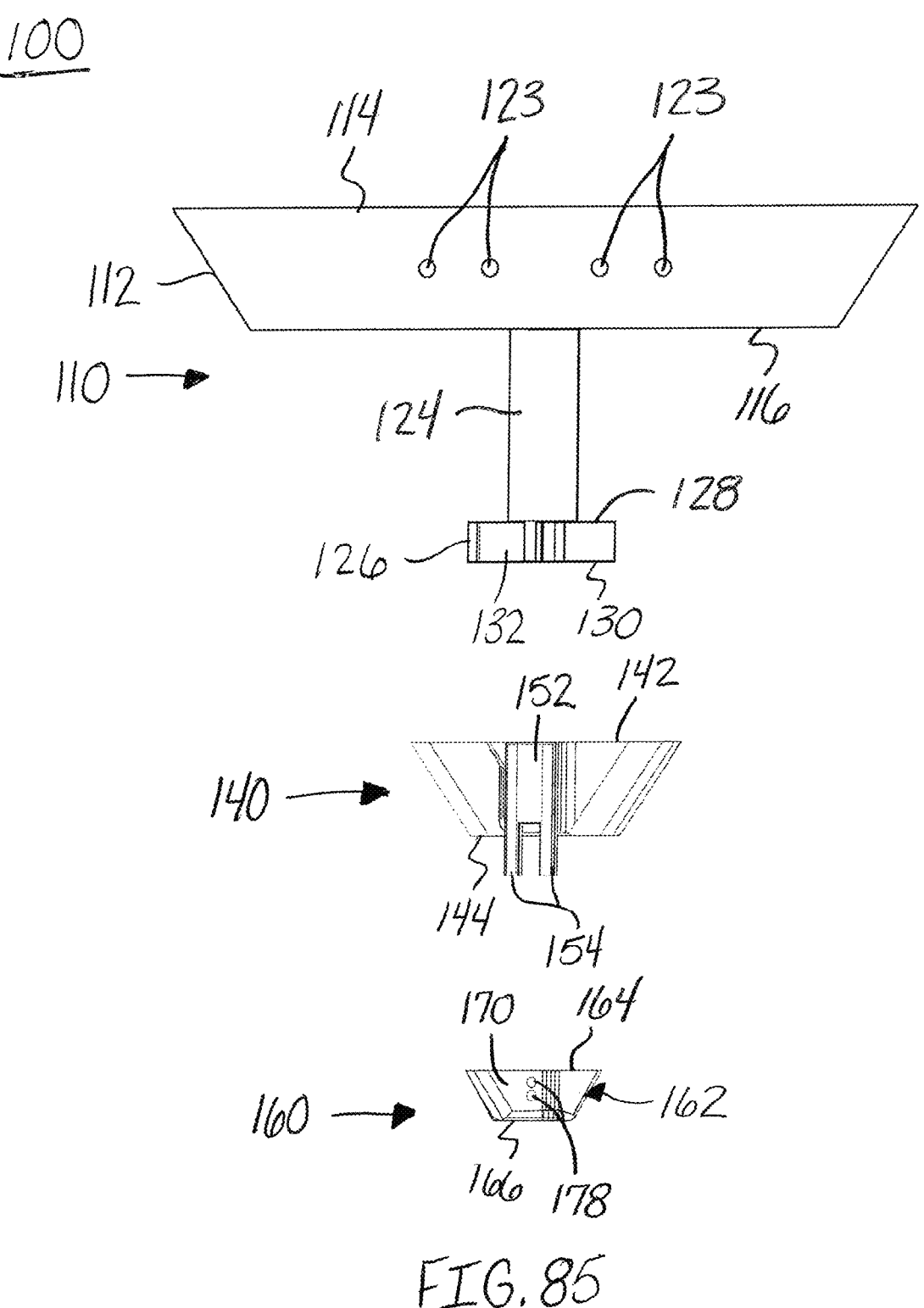
FIG. 85 is an exploded side view of the implant system of FIG. 1, in accordance with an aspect of the present invention.

As shown in FIGS. 78-81 and 84, the handle member 510 may include a rod or shaft 512 with a first end 514 and a second end 516. The first end 514 may be configured or sized and shaped to engage an implant 160, 200, 250, 400, 450. The second end 516 may be configured or sized and shaped to couple to a handle 518. The base member 520 may include a body 522 with a slot or opening 524 positioned near a middle of the base member 520. The opening 524 may also include a channel or cavity 538 extending from the opening 524 into the body 522, as shown in FIG. 84. The cavity 538 may be configured to receive a spring loaded mechanism or spring loaded ball 568, as shown in FIG. 84. The base member 520 may also include an arm 526 at a first end. The arm 526 may include a through hole 528 for receiving the bone contacting member 550. The through hole 528 may be, for example, threaded. The base member 520 may further include a first leg or first fork portion 530, a second leg or second fork portion 532 with a channel, recess or groove 534 extending between the first and second legs 530, 532. The channel 534 may be sized and shaped or configured to receive the shaft 512 of the handle member 510. As shown in FIGS. 75 and 79, the base member 520 may also include a recess 536 in a portion of the legs 530, 532 and a portion of the body 522 where the legs 530, 532 engage the body 522. The recess 536 is sized and shaped or configured to receive the body 562 of the securement member 560.

Figure 76:
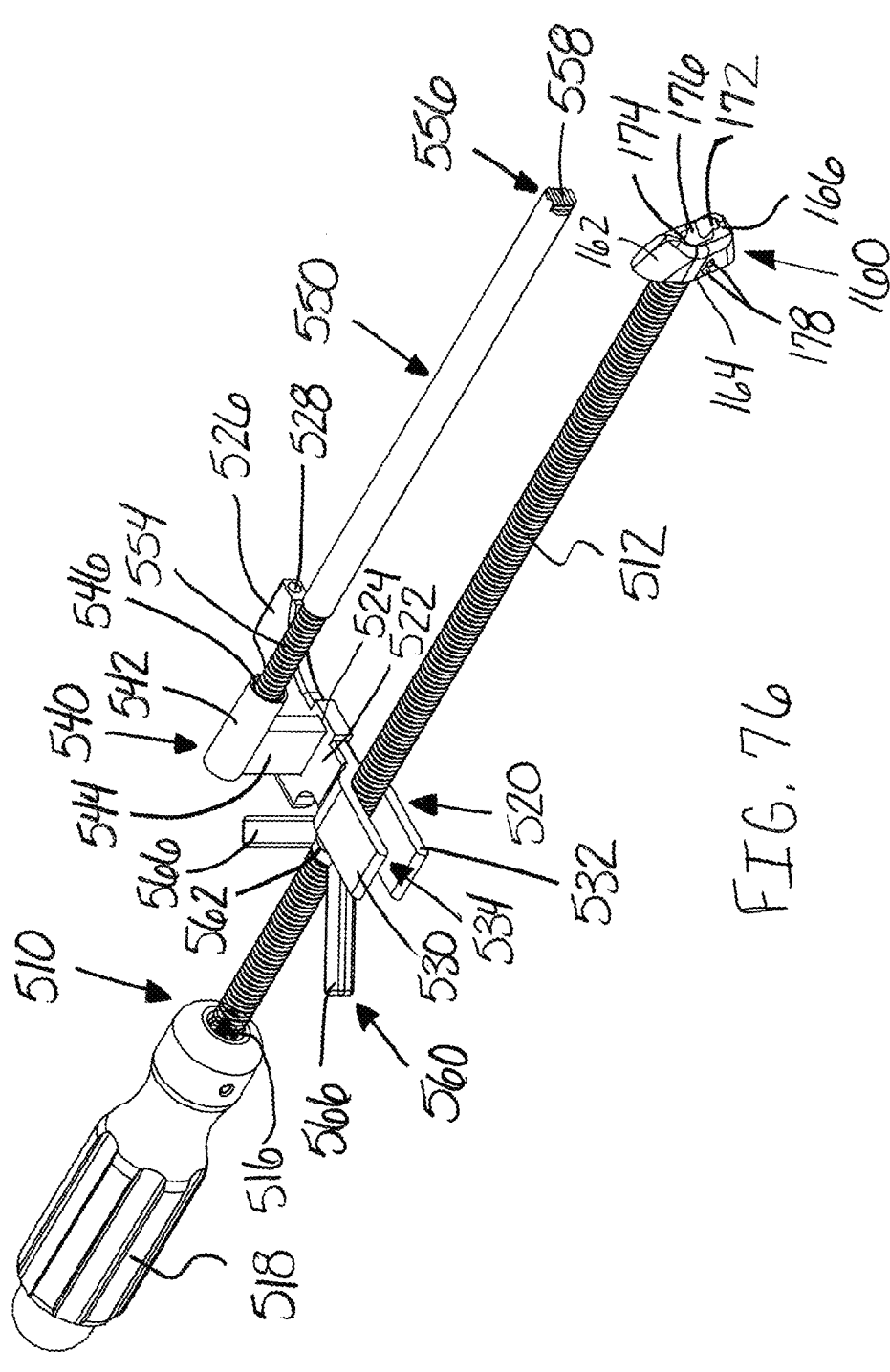
FIG. 76 is a second end, perspective view of the reduction tool of FIG. 75, in accordance with an aspect of the present invention.
Figure 77:
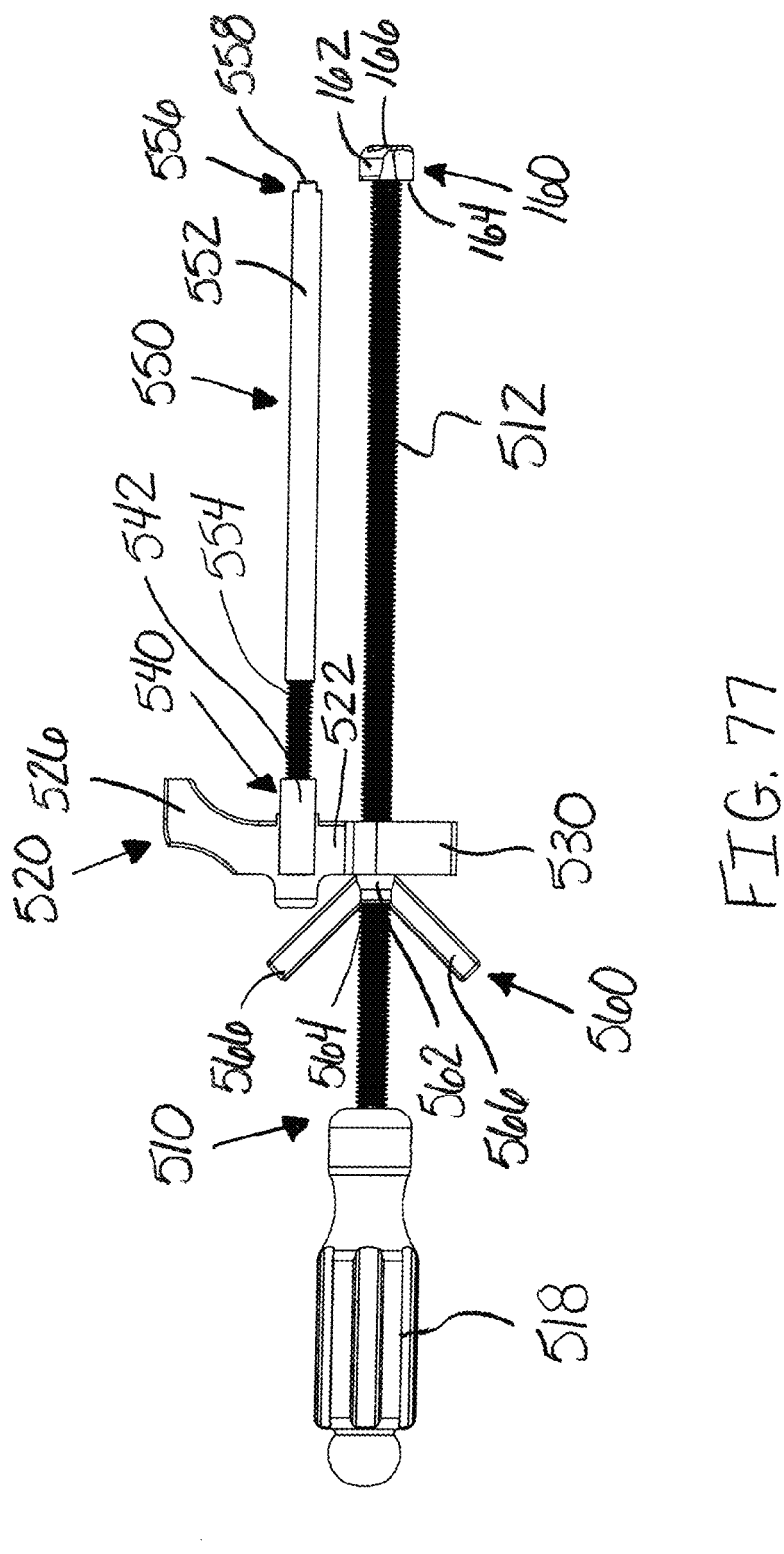
FIG. 77 is a side view of the reduction tool of FIG. 75, in accordance with an aspect of the present invention.

The coupling member 540 may include a body 542 and an engagement member 544 extending away from one side of the body 542. The body 542 may include a through hole 546, which may be, for example, threaded. The engagement member 544 may be inserted into the opening 524 to couple the coupling member 540 to the base member 520, as shown in FIGS. 75-77. The engagement member 544 may include a plurality of detents or grooves 548 positioned along the top surface of the engagement member 544, as shown in FIG. 84. The spring loaded ball 568 of the base member 520 may engage the detents 548 when the engagement member 544 is inserted into the slot 524, as shown in FIG. 84. As force is applied to the coupling member 540 to move the engagement member 544 within the slot 524 the spring loaded ball 568 may engage the detents 548 until a desired distance between the handle member 510 and the bone contact member 550 is achieved. Once the desired distance is selected, the spring loaded ball 568 will remain in the corresponding detent 548 at that distance to secure the bone contacting member 550 in the desired location for reducing the patient's vertebrae. The bone contacting member 550 may include a shaft 552 with a threaded end 554 at a first end and a foot 556 at a second end. The threaded end 554 is sized and shaped or configured to engage the through hole 546 of the coupling member 540. The foot 556 may include at least one spike, tooth, concavity, curvature or other surface texture 558.

The securement member 560 may have a body or coupling member 562 with a through hole 564 extending through the coupling member 562, as shown in FIGS. 78 and 79. The securement member 560 may also include at least one wing, arm, or member 566 extending away from the body 562 for rotating the securement member 560. The through hole 564 may be threaded onto the shaft 512 of the handle member 510, as shown in FIGS. 75-77. In addition, after the base member 520 is aligned in the desired position on the shaft 512, the securement member 560 may be rotated to engage the body 562 with the recess 536 of the base member 520 to secure the securement member 560 to the shaft 512.

Figures 82, 83:
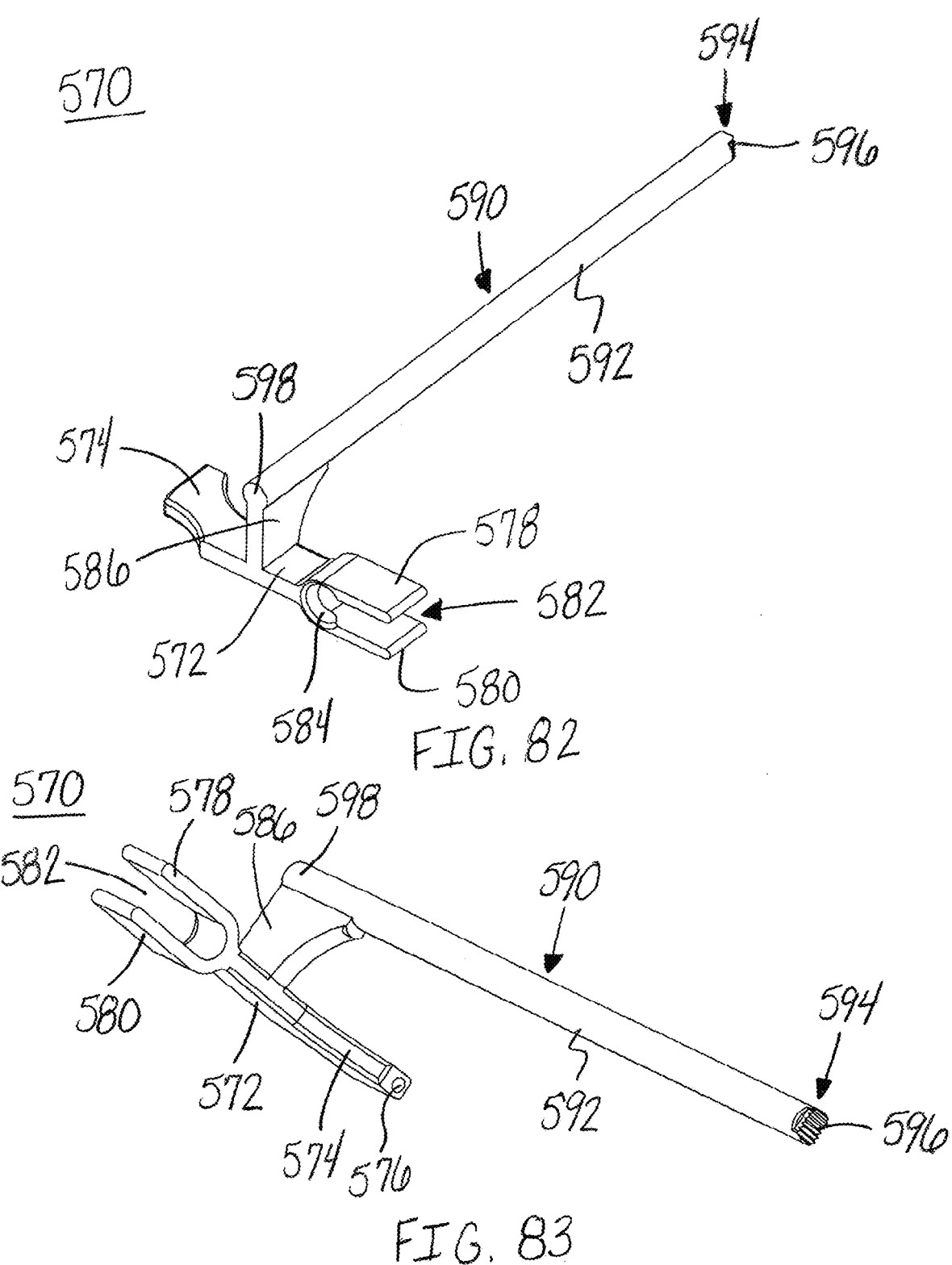
FIG. 82 is a first end perspective view of an alternative holder of the reduction tool of FIG. 75, in accordance with an aspect of the present invention.
FIG. 83 is a second end perspective view of the holder of FIG. 82, in accordance with an aspect of the present invention.

Referring now to FIGS. 82-83, a holder 570 is shown. The holder 570 may be, for example, a monolithic base member 520, a coupling member 540 and a bone contacting member 550. The holder 570 may include a base portion 572 with an arm 574 extending away from the base portion 572. As shown in FIG. 83, the arm 574 may include an opening or through hole 576. The base portion 572 may also include a first leg or fork portion 578 and a second leg or fork portion 580 with a channel, recess, or groove 582 extending between the legs 578, 580. The base portion 572 may also include a recess 584 inset into a portion of the base portion 572 and a portion of each of the legs 578, 580, as shown in FIG. 82. The holder 570 may also include a projection 586 with a first end of the projection 586 extending out from a middle portion of the holder 570. The holder 570 may further include a bone contacting portion 590 coupled to a second end of the projection 586. The bone contacting portion 590 may also include a shaft 592 with a distal end or foot 594 and a proximal end 598. The proximal end 598 may be coupled to the projection 586. The distal end or foot 594 may include at least one spike, tooth, concavity, curvature or other surface texture 596.

Figure 86:
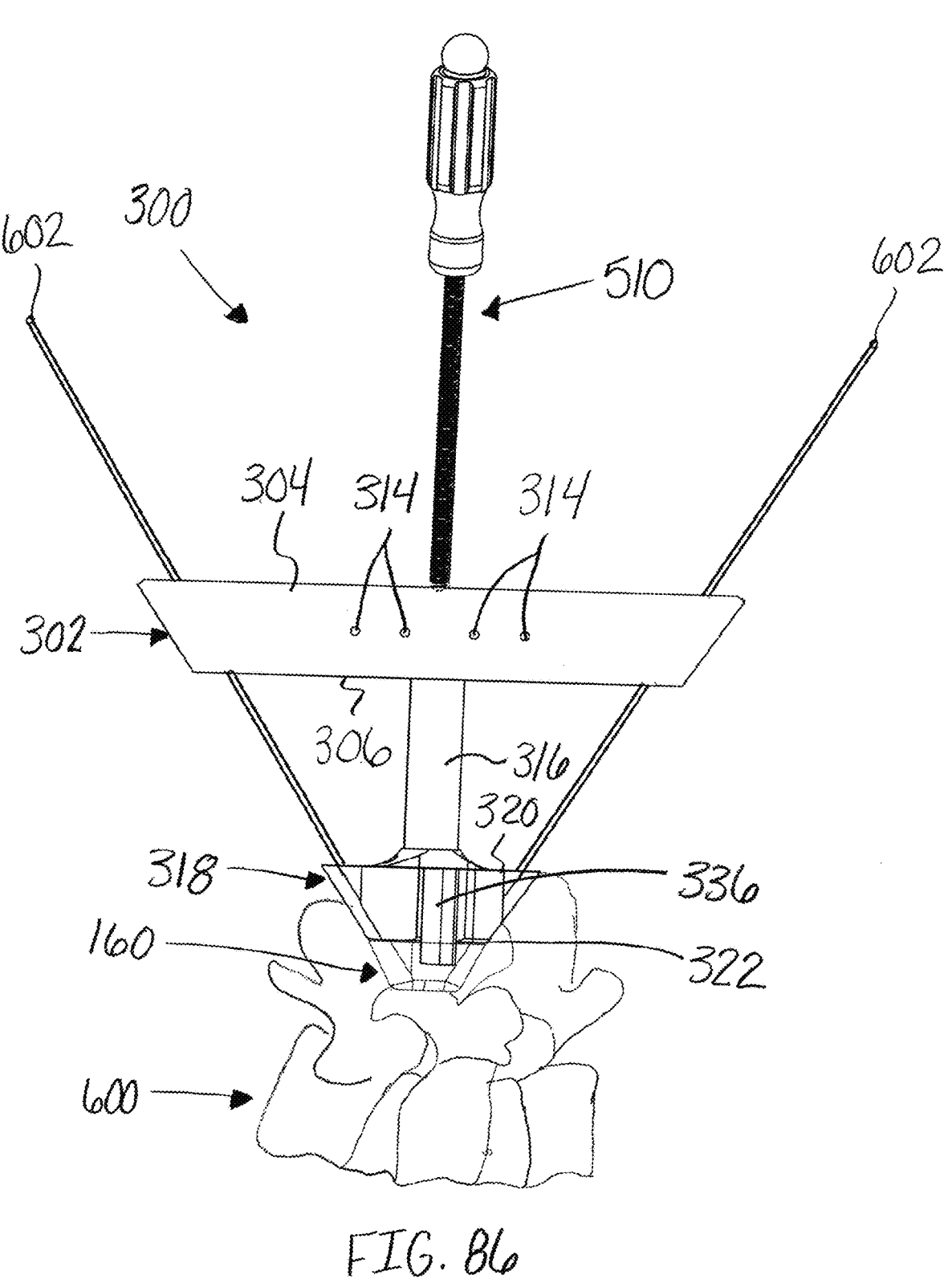
FIG. 86 is a side view of the implant system of FIG. 1 positioned on the vertebrae, in accordance with an aspect of the present invention.

One method of using a bone fusion system includes, for example, making a mid-line incision large enough for a tower instrument 110, 300 and pre-assembled connector implant 160, 200, 250, 400, 450 to fit as it is placed along the spinous process. Next, the method may include placing the coupled tower instrument 110, 300 and connector implant 160, 200, 250, 400, 450 through the incision and positioning the connector implant 160, 200, 250, 400, 450 on the appropriate side of the spinous process 600, as shown in FIG. 86. The method may also include inserting a first Jamshidi needle through a first slot or facet slot on the tower instrument 110, 300 and confirming the Jamshidi needle placement using fluoroscopy. The method may further include inserting a second Jamshidi needle through a second slot or pedicle slot on the tower instrument 110, 300 and confirming the Jamshidi needle placement using fluoroscopy. Next, the method may include confirming the trajectories of both Jamshidi needles with anteroposterior (AP) and lateral fluoroscopy. Then, the method may include removing the Jamshidi needle stylets when the correct position is achieved. The method may further include inserting k-wires 602 through the Jamshidi tubes and confirming the desired k-wire 602 placement with fluoroscopy. Next, the method may include removing the Jamshidi tubes and disengaging the tower instrument 110, 300 from the k-wires 602 and the connector implant 160, 200, 250, 400, 450. The method may further include removing the tower instrument 110, 300 leaving the connector implant 160, 200, 250, 400, 450 and k-wires 602 in place within the patient. Then, the method may include sliding a cannulated facet/pedicle screw over the facet/pedicle k-wire, driving the facet/pedicle screw into the bone, for example, the facet and pedicle, and confirming the placement with fluoroscopy. The method may also include sliding a cannulated screw over the k-wire, driving the pedicle screw into the pedicle, and confirming the placement with fluoroscopy. Next, the method may include removing the k-wires and inserting the center locking screw 480, 490 until the locking screw pushes the facet/pedicle and pedicle screws slightly. Finally, the method may include confirming the correct placement of the bone fusion device with fluoroscopy.

In an embodiment where the patient presents with a spondylolisthesis, after placing the two k-wires into the pedicle and the facet/pedicle, the guide tower 110, 300 may be removed. Next, a cannulated screw may be placed over the k-wire and secured in place. The reduction tool 500 may then be coupled to the implant 160, 200, 250, 400, 450 through the incision before the second screw is placed, for example, before a screw is placed in the facet/pedicle. The foot 558, 596 of the reduction tool 500 may be placed onto the inferior lamina and placement may be verified by fluoroscopy. The base member 520, coupling member 540 and bone contacting member 550 may be attached to the superior aspect of the handle member 510, then the securement member 560 may secure the base member 520 to the handle member 510. When the securement member 560 is attached to the handle member 510 and engages the base member 520, the securement member 560 pushes down on the bone contacting member 550, which places a force on the lamina and may bend the shaft 552. As the securement member 560 is rotated, the foot 556 contacts the lamina and the vertebrae is loaded to assist with realignment. Once the reduction tool 500 is assembled and bone contacting member 550 is firmly placed on the lamina, the coupled reduction tool 500 and implant 160, 200, 250, 400, 450 may be tilted caudally to use the reduction tool 500 as a lever to tilt the superior vertebra with the inserted screw into the pedicle. The length of the rod 512 may be selected to assist with the leverability during reduction. The reduction tool 500 is then used to change the relative position of the vertebrae and ultimately reducing the lysthesis. After reduction, the second screw, for example, the screw into the facet/pedicle can be placed over the second k-wire and fixed through the facet to complete the stabilization.

The anatomic fastener or screw insertion angle may be, for example, predetermined by the implant 160, 200, 250, 400, 450 and targets the fastener trajectory via fastener holes in the device. The fasteners are implanted in such a fashion as to accomplish a non co-planer, axial divergent fastener trajectory.

In an embodiment, the first screw will be guided by the device 160, 200, 250, 400, 450 and secured into bone through one of the through hole features or guide holes. The second screw is implanted at the opposite angle through one of the guide holes in the device 160, 200, 250, 400, 450 and may be offset by a distance such as to allow the screws to pass to their desired final position. The compound angle of the screw generally forms a "V" shape, where the screws are at opposing angles and where one screw may be medial or lateral to the opposite screw by a distance of the diameter of the screw. The compound angle may be, for example, approximately 50-85 degrees. The two screws that form the "V" shape are then securely locked into place by a locking screw that is driven down an axis approximately at the center of the "V" shape until contact is made with each screw, loading both screws in a manner that forces the screws apart by, for example, slightly deforming or displacing the screw axis, into the locking block thus locking the screws to prevent rotation and axial displacement to secure the entire rigid construct.

The device 160, 200, 250, 400, 450 is not fixed to bone, the device 160, 200, 250, 400, 450, two screws and locking screw will securely lock the bone screws to form a construct.

The device guide holes for fastener delivery are positioned at an optimum insertion based on anatomical and surgical data. The guide hole tolerances will provide several degrees of additional translation or angulation to address the variation in patient anatomy.

The medial aspect of the implant 160, 200, 250, 400, 450 is configured to enable insertion with respect to the anatomy of the spinous process and the radial transition into the lamina.

While the implants or devices 160, 200, 250, 400, 450 are described above for fixation using one facet and one pedicle location, this is an exemplary embodiment. The implants or devices 160, 200, 250, 400, 450 could also be used to fix or span different anatomic locations of bone fracture segments to facilitate a surgical correction, fracture healing or bone fusion. While the descriptions utilized are for screw fixation, the fixation elements could be, for example, smooth rods, splined or fluted rods, or a combination of the elements described above, as would be known by one of ordinary skill in the art.

As may be recognized by those of ordinary skill in the art based on the teachings herein, numerous changes and modifications may be made to the above-described and other embodiments of the present invention without departing from the scope of the invention. The implants, screws, reduction tool components and other components of the devices and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and systems may include more or fewer components or features than the embodiments as described and illustrated herein. For example, the components and features of FIGS. 10-17, FIGS. 37-47, FIGS. 48-55, FIGS. 60-65, and FIGS. 66-72 may all be used interchangeably and in alternative combinations as would be modified or altered by one of skill in the art. In addition, the components and features of, for example, FIGS. 1-9 and 18-25 and FIGS. 56-59 may all be used interchangeably and in alternative combinations as would be modified or altered by one of skill in the art. Accordingly, this detailed description of the currently-preferred embodiments is to be taken as illustrative, as opposed to limiting the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

We claim:

1. An implant, comprising:
   a body with a top surface and a bottom bone contacting surface, the body comprising:
   a first opening at a first end of the body, wherein the first opening is angled at a first trajectory as the first opening extends from the top surface to the bottom bone contacting surface;
   a second opening at a second end of the body, wherein the second opening is angled at a second trajectory as the second opening extends from the top surface to the bottom bone contacting surface; and
   a third opening positioned between the first opening and the second opening, wherein at least a portion of the first opening overlaps at least a portion of the third opening at the bottom bone contacting surface of the implant, and wherein at least a portion of the second opening overlaps at least a portion of the third opening at the bottom bone contacting surface of the implant;

wherein the first trajectory and the second trajectory are configured to not intersect;
   a first fastener for insertion into the first opening;
   a second fastener for insertion into the second opening; and
   a set screw with a first end and a second end, wherein the set screw is inserted into the third opening to position the second end of the set screw adjacent to the bottom bone contacting surface of the implant, wherein the second end of the set screw engages at least a portion of the first fastener between a first end and a second end of the first fastener while the first fastener extends beyond the bottom bone contacting surface and at least a portion of the second fastener between a first end and a second end of the second fastener while the second fastener extends beyond the bottom bone contacting surface;
   wherein the first fastener extends past the second fastener in at least one of a crossed and an X-shape in a medial-lateral view below the bottom bone contacting surface, and wherein the first fastener does not intersect with the second fastener.

2. The implant of claim 1, wherein the third opening is a locking opening.

3. The implant of claim 1, wherein the body further comprises:
   a first side; and
   a second side, wherein the first side is curved as the first side extends from the top surface to the bottom bone contacting surface.

4. The implant of claim 3, wherein the top surface is opposite and parallel to the bottom bone contacting surface.

5. The implant of claim 3, wherein the implant comprises a first end surface and a second end surface, wherein the first end surface and the second end surface extend from the top surface to the bottom bone contacting surface.

6. The implant of claim 5, wherein the first end surface and the second end surface are tapered between the top surface and the bottom bone contacting surface.

7. The implant of claim 6, wherein the first end surface and the second end surface are tapered at an angle and the angle is at least one of an acute angle and an obtuse angle relative to the top surface.

8. The implant of claim 5, wherein the first end surface and the second end surface are accurate in shape.

9. The implant of claim 3, wherein the second side further comprises a side indicator, and wherein the side indicator is configured as at least one of a protrusion and a side extension.

10. The implant of claim 3, wherein the second side further comprises a side indicator, and wherein the side indicator is configured as at least one of a slot, a recess and a surface marking.

11. The implant of claim 3, wherein the first opening, the second opening and the third opening extend from the top surface to and through the bottom bone contacting surface.

12. The implant of claim 1, further comprising:
   at least one alignment member.

13. The implant of claim 1, wherein the body has a polygonal shape.

14. The implant of claim 1, wherein the body is configured with a generally trapezoidal prism shape.

15. The implant of claim 1, wherein the third opening is threaded.

16. The implant of claim 1, wherein the first opening and the second opening are non-threaded.

17. The implant of claim 1, wherein the first opening extends through the body at a first angle between 65-85 degrees from the top surface of the body, and wherein the second opening extends through the body at a second angle between 65-85 degrees.

18. The implant of claim 1, wherein the first trajectory of the first opening of the body extends at an angle opposite a direction of the second trajectory of the second opening of the body.

19. The implant of claim 1, wherein the first opening extends from a first side of the body towards a second side of the body, wherein the second opening extends from the second side towards the first side.

20. An implant, comprising:

a body with a top surface and a bottom bone contacting surface, the body comprising:

a first opening at a first end of the body, wherein the first opening is angled at a first trajectory as the first opening extends from the top surface to the bottom bone contacting surface;

a second opening at a second end of the body, wherein the second opening is angled at a second trajectory as the second opening extends from the top surface to the bottom bone contacting surface; and a third opening positioned between the first opening and the second opening, wherein at least a portion of the first opening overlaps at least a portion of the third opening at the bottom bone contacting surface of the implant, and wherein at least a portion of the second opening overlaps at least a portion of the third opening at the bottom bone contacting surface of the implant;

wherein the first trajectory and the second trajectory are configured to not intersect;

a first fastener for insertion into the first opening;

a second fastener for insertion into the second opening; and a set screw with a first end and a second end, wherein the set screw is inserted into the third opening to position the second end of the set screw adjacent to the bottom bone contacting surface of the implant, wherein the second end of the set screw engages at least a portion of the first fastener between a first end and a second end of the first fastener while the first fastener extends beyond the bottom bone contacting surface and at least a portion of the second fastener between a first end and a second end of the second fastener while the second fastener extends beyond the bottom bone contacting surface;

wherein the first fastener extends past the second fastener in at least one of a crossed and an X-shape in a medial-lateral view below the bottom bone contacting surface, and wherein the first fastener does not intersect with the second fastener; and wherein the top surface comprises an overall length and the bottom bone contacting surface comprises an overall length, and wherein top surface overall length is longer than the bottom bone contacting surface overall length.

\* \* \* \* \*